(12) United States Patent
Mori et al.

(10) Patent No.: US 9,216,954 B2
(45) Date of Patent: Dec. 22, 2015

(54) SERINE RACEMASE INHIBITOR

(71) Applicant: National University Corporation University of Toyama, Toyama (JP)

(72) Inventors: Hisashi Mori, Toyama (JP); Naoki Toyooka, Toyama (JP); Mineyuki Mizuguchi, Toyama (JP); Takayuki Obita, Toyama (JP); Syuichi Hirono, Tokyo (JP); Hiroaki Goda, Kanagawa (JP)

(73) Assignee: NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 0 days.

(21) Appl. No.: 14/375,006

(22) PCT Filed: Jan. 24, 2013

(86) PCT No.: PCT/JP2013/051385
§ 371 (c)(1),
(2) Date: Jul. 28, 2014

(87) PCT Pub. No.: WO2013/111798
PCT Pub. Date: Aug. 1, 2013

(65) Prior Publication Data
US 2014/0371291 A1 Dec. 18, 2014

(30) Foreign Application Priority Data

| Jan. 27, 2012 | (JP) | 2012-015233 |
| Feb. 23, 2012 | (JP) | 2012-037977 |
| Mar. 7, 2012 | (JP) | 2012-049955 |
| Jun. 15, 2012 | (JP) | 2012-135591 |

(51) Int. Cl.
*C07C 337/06* (2006.01)
*C07D 333/24* (2006.01)
*C07D 333/38* (2006.01)
*C07C 311/13* (2006.01)
(Continued)

(52) U.S. Cl.
CPC ............ *C07C 337/06* (2013.01); *C07C 237/22* (2013.01); *C07C 311/13* (2013.01); *C07C 311/19* (2013.01); *C07C 311/21* (2013.01); *C07C 311/29* (2013.01); *C07C 311/58* (2013.01); *C07C 327/42* (2013.01); *C07C 335/08* (2013.01); *C07C 335/16* (2013.01); *C07C 335/18* (2013.01); *C07D 333/24* (2013.01); *C07D 333/38* (2013.01); *C07C 2101/14* (2013.01)

(58) Field of Classification Search
CPC ....................................................... C07C 337/06
USPC .......................................... 514/438; 564/18
See application file for complete search history.

(56) References Cited

U.S. PATENT DOCUMENTS

2009/0163545 A1* 6/2009 Goldfarb .................... 514/312

FOREIGN PATENT DOCUMENTS

| JP | 2008-096313 | 4/2008 |
| WO | WO2011-119798 | * 9/2011 |
| WO | WO-2011/139636 | 11/2011 |

OTHER PUBLICATIONS

Feng et al., Huaxue Shiji, (1994), vol. 16(4), pp. 211-214.*
(Continued)

*Primary Examiner* — Taofiq A Solola
(74) *Attorney, Agent, or Firm* — Mintz Levin Cohn Ferris Glovsky and Popeo, P.C.; David G. Conlin; Joohee Lee

(57) ABSTRACT

A novel serine racemase inhibitor exhibits sufficient activity and specificity. The serine racemase inhibitor includes one or more compounds selected from compounds respectively represented by the following general formulas [MM_1], [DR_1], [DR'_1], [LW_1], and [ED_1] as an active ingredient.

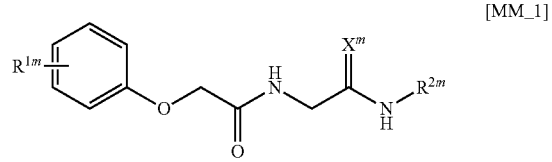

[MM_1]

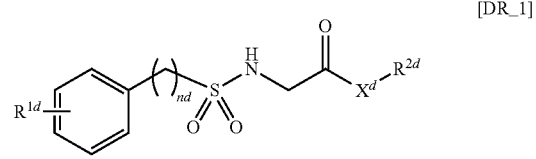

[DR_1]

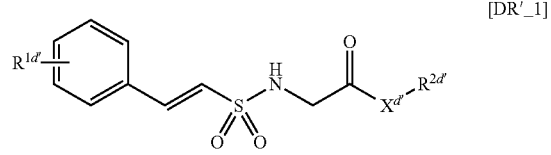

[DR'_1]

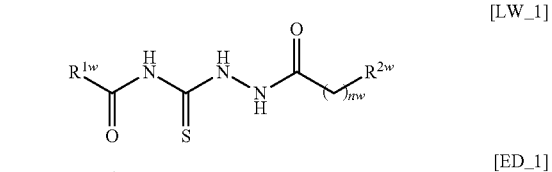

[LW_1]

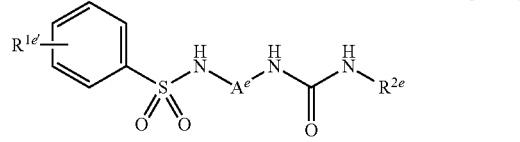

[ED_1]

7 Claims, No Drawings

(51) Int. Cl.
- *C07C 311/19* (2006.01)
- *C07C 311/29* (2006.01)
- *C07C 327/42* (2006.01)
- *C07C 335/08* (2006.01)
- *C07C 335/16* (2006.01)
- *C07C 335/18* (2006.01)
- *C07C 237/22* (2006.01)
- *C07C 311/21* (2006.01)
- *C07C 311/58* (2006.01)

(56) References Cited

OTHER PUBLICATIONS

Feng et al., Yingyong Huaxue, (1993), vol. 10(1), pp. 104-106.*
Feng et al., Gaedeng Xuexiao Huaxue Xuebao (1993), vol. 14(1), pp. 65-67.*
Feng et al., Org. Prepn. Proced. Int. (1992), vol. 24(4), pp. 492-496.*
Feng et al., Youji Huaxue (1992), vol. 12(4), pp. 392-396.*
Feng et al., Chem. Res. Chinese Univ. (1992), vol. 8(3), pp. 315-318.*
Feng et al., Yingyong Huaxue (1992), vol. 9(2), pp. 89-95.*
Feng et al., Gaedeng Xuexiao Huaxue Xuebao (1991), vol. 12(10), pp. 1326-1330.*
Zhang et al., Gaedeng Xuexiao Huaxue Xuebao (1989), vol. 10(5), pp. 471-476.*
Chen et al., Lanzhou Daxue Xuebao, Ziran Kexueban (1988), vol. 24(1), 49-52.*
Lipp et al., Chemische Berichte (1958), vol. 91, pp. 1660-1664.*
Takagi et al., Yakugaku Zasshi (1958), vol. 78, pp. 280-283.*
Hemdan et al., Chinese J. Chem. (2008), vol. 26(2), pp. 388-391.*
Yamato et al., "Ditopic receptors of hexaamide derivatives derived from hexahomotrioxacalix[3]arene triacetic acid", Can. J. Chem. 84: 58-64 (2006).
International Search Report and Written Opinion and the English Translation of International Search Report mailed Apr. 16, 2013, in corresponding PCT Application No. PCT/JP2013/051385.
Inoue et al., "NMDA—and β-Amyloid$_{1-42}$-Induced Neurotoxicity Is Attenuated in Serine Racemase Knock-Out Mice", The Journal of Neuroscience, 28(53):14486-14491 (2008).
Dixon et al., "Slow-Binding Human Serine Racemase Inhibitors from High-Throughput Screening of Combinatorial Libraries", J. Med. Chem. 49:2388-2397 (2006).
Inoue et al., "Pentylenetetrazole-induced seizure is attenuated in serine racemase knockout mice", Abstract, Society for Neuroscience's 40th annual meeting, 2010, P3-r18.

* cited by examiner

SERINE RACEMASE INHIBITOR

CROSS-REFERENCE TO RELATED APPLICATIONS

This application is the U.S. National Phase application pursuant to 35 U.S.C. §371 of PCT International Patent Application No. PCT/JP2013/051385, filed Jan. 24, 2013, which claims priority to Japanese Patent Application No. 2012-015233, filed Jan. 27, 2012, Japanese Patent Application No. 2012-037977, filed Feb. 23, 2012, Japanese Patent Application No. 2012-049955, filed Mar. 7, 2012, and Japanese Patent Application No. 2012-135591, filed Jun. 15, 2012. The contents of these applications are incorporated herein by reference in their entirety.

TECHNICAL FIELD

The present invention relates to a non-peptidic amide derivative having serine racemase inhibitory activity.

BACKGROUND ART

An N-methyl-D-aspartate (NMDA) receptor (hereinafter referred to as "NMDAR") is one type of glutamate receptor.

The NMDAR has been considered to be a receptor that is involved in memory and learning. Therefore, the NMDAR has been one of the targets of Alzheimer-type dementia therapeutic agents.

D-serine is present in the mammalian brain, and is involved in control of the functions of the NMDAR as an endogenous coagonist.

D-serine is synthesized from L-serine by serine racemase (SR).

It has been known that an SR knock-out (KO) mouse shows a reduction in NMDA-induced neurodegeneration (see Non-patent Document 1), and a reduction in PTZ-induced epileptic seizure, for example.

Therefore, SR has been considered to be a new drug target for pathological conditions due to excessive nervous excitement. A dipeptide and the like have been known as an SR inhibitor (see Non-patent Document 2).

RELATED-ART DOCUMENT

Non-Patent Document

Non-patent Document 1: J. Neurosci., 2008, 28(53), 14486-14491.
Non-patent Document 2: J. Med. Chem., 2006, 49, 2388-2397.

SUMMARY OF THE INVENTION

Technical Problem

A dipeptide has a narrow concentration range that shows the SR inhibition effect, may have cellular toxicity, and does not have high specificity.

An object of the invention is to develop a novel SR inhibitor that exhibits sufficient activity and specificity.

Another object of the invention is to develop a novel candidate for a therapeutic agent for treating neurodegenerative diseases and hyperexcitable brain conditions.

Solution to Problem

The inventors of the invention synthesized novel low-molecular-weight compounds from structural information about a lead compound candidate for an SR inhibitor found by in silico screening based on three-dimensional structural information about SR, and evaluated the effects thereof on SR to find novel compounds having SR inhibitory activity. This finding has led to the completion of the invention.

The invention is described in detail below.

The terms used herein have the following meanings unless otherwise specified.

The term "halogen atom" used herein refers to a fluorine atom, a chlorine atom, a bromine atom, and an iodine atom. The term "alkyl group" used herein refers to a linear or branched alkyl group having 1 to 12 carbon atoms, such as methyl, ethyl, propyl, isopropyl, butyl, isobutyl, tert-butyl, pentyl, and hexyl. The term "lower alkyl group" used herein refers to a linear or branched alkyl group having 1 to 6 carbon atoms, such as methyl, ethyl, propyl, isopropyl, butyl, isobutyl, tert-butyl, pentyl, and hexyl. The term "cycloalkyl group" used herein refers to a cycloalkyl group having 3 to 8 carbon atoms, such as cyclopropyl, cyclobutyl, cyclopentyl, and cyclohexyl. The term "aryl group" used herein refers to phenyl, naphthyl, indanyl, indenyl, and the like. The term "aralkyl group" used herein refers to an aryl-lower alkyl group such as benzyl, phenethyl, α-methylphenethyl, diphenylmethyl, and trityl. The term "alkoxy group" used herein refers to a linear or branched alkyloxy group having 1 to 12 carbon atoms, such as methoxy, ethoxy, propoxy, isopropoxy, butoxy, isobutoxy, tert-butoxy, pentyloxy, hexyloxy, heptyloxy, and octyloxy. The term "lower alkoxy group" used herein refers to a linear or branched alkyloxy group having 1 to 6 carbon atoms, such as methoxy, ethoxy, propoxy, isopropoxy, butoxy, isobutoxy, tert-butoxy, pentyloxy, and hexyloxy. The term "alkylene group" used herein refers to a linear or branched alkylene group having 1 to 6 carbon atoms, such as methylene, ethylene, and propylene.

A group that protects a hydroxyl group may be an arbitrary group that can normally be used as a protecting group for a hydroxyl group. Examples of such a group include an acyl group such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, and benzoyl; a lower alkyl group such as methyl, tert-butyl, 2,2,2-trichloroethyl, and 2-trimethylsilylethyl; a lower alkenyl group such as allyl; a lower aralkyl group such as benzyl, p-methoxybenzyl, 3,4-dimethoxybenzyl, diphenylmethyl, and trityl; an oxygen-containing/sulfur-containing heterocyclic group such as tetrahydrofuryl, tetrahydropyranyl, and tetrahydrothiopyranyl; a lower alkoxy/lower alkylthio-lower alkyl group such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, and 1-methyl-1-methoxyethyl; a lower alkyl/aryl-sulfonyl group such as methanesulfonyl and p-toluenesulfonyl; a substituted silyl group such as trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl; and the like.

According to one aspect of the invention, there is provided a serine racemase inhibitor comprising one or more non-peptidic amide derivatives as an active ingredient, the one or more compounds being selected from a phenoxy(N-substituted carbamoylmethyl)acetamide derivative represented by a general formula [MM_1], an N-(substituted)-2-(substituted sulfamoylamino)acetamide derivative represented by a general formula [DR_1], an N-(substituted)-2-(substituted sulfamoylamino)acetamide derivative represented by a general formula [DR'_1], an N-[(acyl)hydrazinocarbothioyl]acetamide derivative represented by a general formula [LW_1], and a benzenesulfonamide derivative represented by a general formula [ED_1],

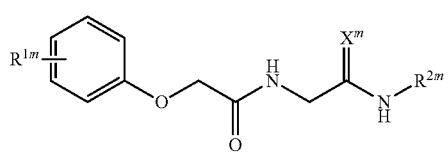

[MM_1]

wherein R$^{1m}$ is atoms or substituents selected from a hydrogen atom, a halogen atom, an alkyl group, an alkoxy group, and a hydroxyl group that is optionally protected, R$^{2m}$ is a substituted or unsubstituted aryl group, a substituted or unsubstituted aralkyl group, or a substituted or unsubstituted cycloalkyl group, and X$^m$ is an oxygen atom or a sulfur atom,

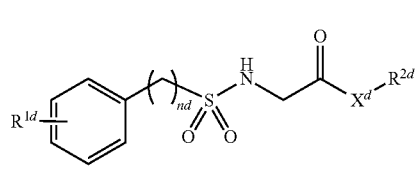

[DR_1]

wherein R$^{1d}$ is atoms or substituents selected from a hydrogen atom, a halogen atom, an alkyl group, an alkoxy group, and a hydroxyl group that is optionally protected, R$^{2d}$ is a substituted or unsubstituted aryl group, a substituted or unsubstituted aralkyl group, or a substituted or unsubstituted arylacetamide group, X$^d$ is an oxygen atom or an imino group, and nd is 0 or 1,

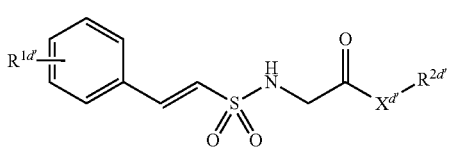

[DR'_1]

wherein R$^{1d'}$ is atoms or substituents selected from a hydrogen atom, a halogen atom, an alkyl group, an alkoxy group, and a hydroxyl group that is optionally protected, R$^{2d'}$ is a substituted or unsubstituted aryl group, a substituted or unsubstituted aralkyl group, or a substituted or unsubstituted arylacetamide group, and X$^{d'}$ is an oxygen atom or an imino group,

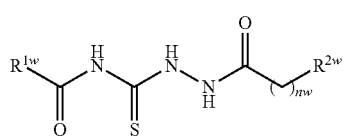

[LW_1]

wherein R$^{1w}$ is a substituted or unsubstituted styryl group, a substituted or unsubstituted benzyl group, or a substituted or unsubstituted cyclohexylmethyl group, R$^{2w}$ is a substituted or unsubstituted aryl group, or a substituted or unsubstituted heterocyclic group that includes an oxygen atom or a sulfur atom as a ring atom, and nw is 0, 1, or 2,

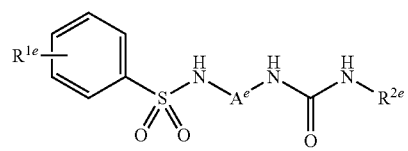

[ED_1]

wherein R$^{1e}$ is atoms or substituents selected from a hydrogen atom, a halogen atom, an alkyl group, and an alkoxy group, R$^{2e}$ is a substituted or unsubstituted phenyl group or a substituted or unsubstituted tolylsulfonyl group, and A$^e$ is an alkylene group or a phenylene group.

Another aspect of the invention provides novel non-peptidic amide derivatives having serine racemase inhibitory activity and respectively represented by the following general formulas.

A phenoxy(N-substituted carbamoylmethyl)acetamide derivative represented by the following general formula [MM_2].

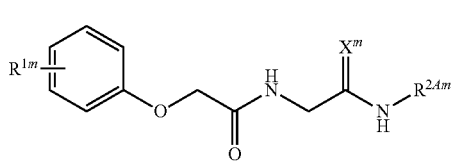

[MM_2]

wherein R$^{1m}$ is atoms or substituents selected from a hydrogen atom, a halogen atom, an alkyl group, an alkoxy group, and a hydroxyl group that is optionally protected, R$^{2Am}$ is an aryl group, an aralkyl group, or a cycloalkyl group that is optionally substituted with one or two atoms or substituents selected from a halogen atom, an alkyl group, an alkoxy group, a nitro group, and a hydroxyl group that is optionally protected, and X$^m$ is an oxygen atom or a sulfur atom.

An N-(substituted)-2-(substituted sulfamoylamino)acetamide derivative represented by the following general formula [DR_1a].

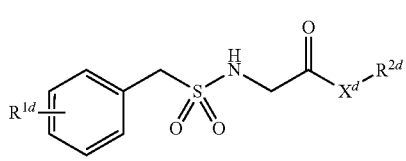

[DR_1a]

wherein R$^{1d}$ is atoms or substituents selected from a hydrogen atom, a halogen atom, an alkyl group, an alkoxy group, and a hydroxyl group that is optionally protected, R$^{2d}$ is a substituted or unsubstituted aryl group, a substituted or unsubstituted aralkyl group, or a substituted or unsubstituted arylacetamide group, and X$^d$ is an oxygen atom or an imino group.

An N-(substituted)-2-(substituted sulfamoylamino)acetamide derivative represented by the following general formula [DR_1b].

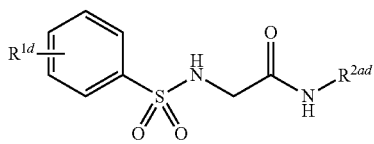

[DR_1b]

wherein $R^{1d}$ is atoms or substituents selected from a hydrogen atom, a halogen atom, an alkyl group, an alkoxy group, and a hydroxyl group that is optionally protected, and $R^{2ad}$ is a substituted or unsubstituted benzyl group or a substituted or unsubstituted arylacetamide group.

An N-(substituted)-2-(substituted sulfamoylamino)acetamide derivative represented by the following general formula [DR'_1].

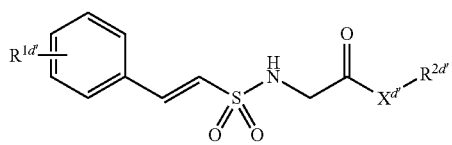

[DR'_1]

wherein $R^{1d'}$ is atoms or substituents selected from a hydrogen atom, a halogen atom, an alkyl group, an alkoxy group, and a hydroxyl group that is optionally protected, $R^{2d'}$ is a substituted or unsubstituted aryl group, a substituted or unsubstituted aralkyl group, or a substituted or unsubstituted arylacetamide group, and $X^{d'}$ is an oxygen atom or an imino group.

An N-[(acyl)hydrazinocarbothioyl]acetamide derivative represented by the following general formula [LW_1 d].

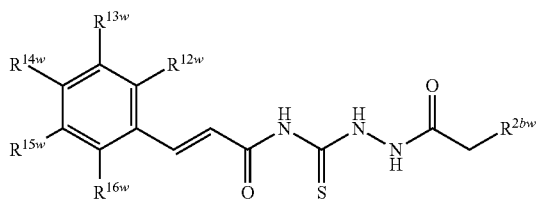

[LW_1d]

wherein $R^{13w}$ is a halogen atom, $R^{12w}$, $R^{14w}$, $R^{15w}$, and $R^{16w}$ are independently atoms or substituents selected from a hydrogen atom, a halogen atom, an alkyl group, an alkoxy group, and a nitro group, and $R^{2bw}$ is a substituted or unsubstituted aryl group, or a substituted or unsubstituted heterocyclic group that includes an oxygen atom or a sulfur atom as a ring atom.

An N-[(acyl)hydrazinocarbothioyl]acetamide derivative represented by the following general formula [LW_1e].

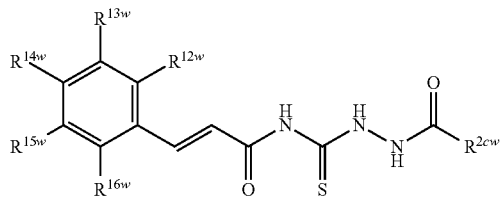

[LW_1e]

wherein $R^{2cw}$ is a substituted or unsubstituted heterocyclic group that includes an oxygen atom or a sulfur atom as a ring atom, and (1) $R^{12w}$, $R^{14w}$, and $R^{16w}$ are a hydrogen atom, and $R^{13w}$ and $R^{15w}$ are a halogen atom, or (2) $R^{13w}$, $R^{14w}$, and $R^{15w}$ are a hydrogen atom, and $R^{12w}$ and $R^{16w}$ are an alkoxy group.

An N-[(acyl)hydrazinocarbothioyl]acetamide derivative represented by the following general formula [LW_1g].

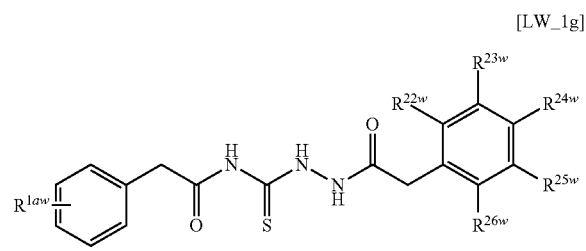

[LW_1g]

wherein $R^{1aw}$ is atoms or substituents selected from a halogen atom, an alkyl group, an alkoxy group, a nitro group, and a hydroxyl group that is optionally protected, and (1) $R^{24w}$ is a halogen atom, and $R^{22w}$, $R^{23w}$, $R^{25w}$, and $R^{26w}$ are a hydrogen atom, or (2) $R^{23w}$ is an alkyl group, and $R^{22w}$, $R^{24w}$, $R^{25w}$, and $R^{26w}$ are a hydrogen atom, or (3) $R^{22w}$ and $R^{26w}$ are a halogen atom, and $R^{23w}$, $R^{24w}$, and $R^{25w}$ are a hydrogen atom, or (4) $R^{23w}$ and $R^{25w}$ are a halogen atom, and $R^{22w}$, $R^{24w}$, and $R^{26w}$ are a hydrogen atom.

An N-[(acyl)hydrazinocarbothioyl]acetamide derivative represented by the following general formula [LW_1c].

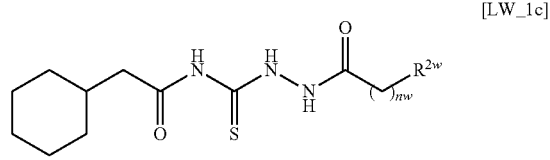

[LW_1c]

wherein $R^{2w}$ is a substituted or unsubstituted aryl group, or a substituted or unsubstituted heterocyclic group that includes an oxygen atom or a sulfur atom as a ring atom, and nw is 0, 1, or 2.

A benzenesulfonamide derivative represented by the following general formula [ED_1aa].

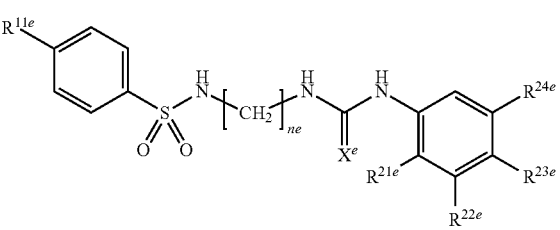

[ED_1aa]

wherein $R^{11e}$ is a hydrogen atom, an alkyl group, or an alkoxy group, $R^{21e}$ is a hydrogen atom, a halogen atom, or an alkyl group, $R^{22e}$ is a hydrogen atom or a halogen atom, $R^{23e}$ is a hydrogen atom or a halogen atom, $R^{24e}$ is a hydrogen atom, an alkyl group, or an alkoxy group, $X^e$ is an oxygen atom or a sulfur atom, and ne is 2 or 3, provided that a case where $R^{11e}$ is an alkyl group, $R^{21e}$ and $R^{23e}$ are a halogen atom, $R^{22e}$ and $R^{24e}$ are a hydrogen atom, $X^e$ is an oxygen atom, and ne is 2 is excluded.

A benzenesulfonamide derivative represented by the following general formula [ED_1ab].

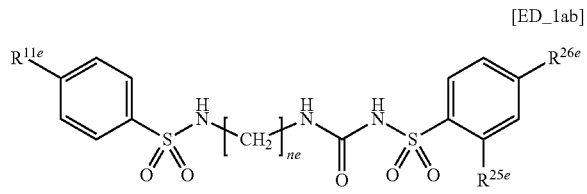

[ED_1ab]

wherein $R^{11e}$ is a hydrogen atom, an alkyl group, or an alkoxy group, $R^{25e}$ and $R^{26e}$ are independently a hydrogen atom or an alkyl group, and ne is 2 or 3.

A benzenesulfonamide derivative represented by the following general formula [ED_1ba].

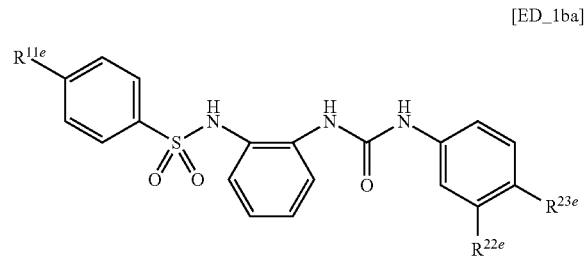

[ED_1ba]

wherein $R^{11e}$ is a hydrogen atom, an alkyl group, or an alkoxy group, and $R^{22e}$ and $R^{23e}$ are independently a hydrogen atom or an alkyl group.

The scope of the invention includes any isomers (e.g., optical isomer, geometric isomer, and tautomer) of the non-peptidic amide derivatives respectively represented by the above general formulas, and also includes hydrates, solvates, and any crystalline forms thereof.

The non-peptidic amide derivatives respectively represented by the above general formulas may form a salt. Examples of such a salt include salts formed via an imino group or a hydroxyl group.

Salts of the DR compound and the ED compound may be salts with an alkali metal (e.g., sodium and potassium).

Examples of a preferable salt include a pharmacologically acceptable salt.

Examples of a preferable compound having serine racemase inhibitory activity include the following compounds.

MM Compound

A phenoxy(N-substituted carbamoylmethyl)acetamide derivative represented by the following general formula.

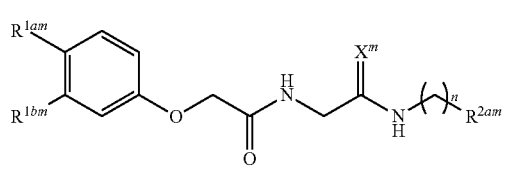

[MM_1a]

wherein $R^{1am}$ is a hydrogen atom, a halogen atom, an alkoxy group, or a hydroxyl group that is optionally protected, $R^{1bm}$ is a hydrogen atom or an alkyl group, $R^{2am}$ is a substituted or unsubstituted aryl group or a substituted or unsubstituted cycloalkyl group, $X^m$ is an oxygen atom or a sulfur atom, and nm is 0 or 1.

Examples of a more preferable compound include the following compound.

A phenoxy(N-substituted carbamoylmethyl)acetamide derivative represented by the following general formula.

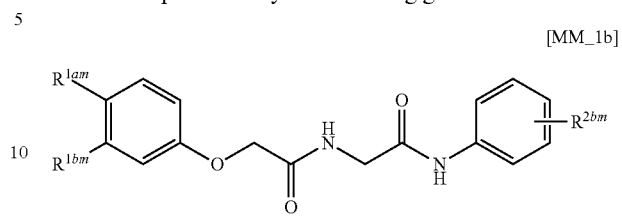

[MM_1b]

wherein $R^{1am}$ is a hydrogen atom, a halogen atom, an alkoxy group, or a hydroxyl group that is optionally protected, $R^{1bm}$ is a hydrogen atom or an alkyl group, and $R^{2bm}$ is atoms or substituents selected from a hydrogen atom, a halogen atom, an alkyl group, a nitro group, and a hydroxyl group.

DR Compound and DR' Compound

An N-(substituted)-2-(substituted sulfamoylamino)acetamide derivative represented by the following general formula.

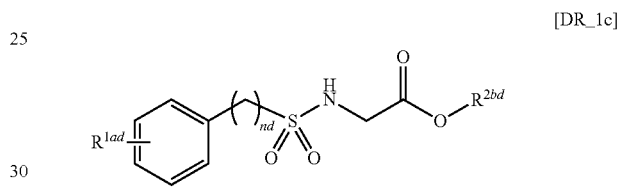

[DR_1c]

wherein $R^{1ad}$ is atoms or substituents selected from a hydrogen atom, a halogen atom, an alkyl group, and an alkoxy group, $R^{2bd}$ is a substituted or unsubstituted aralkyl group, and nd is 0 or 1.

An N-(substituted)-2-(substituted sulfamoylamino)acetamide derivative represented by the following general formula.

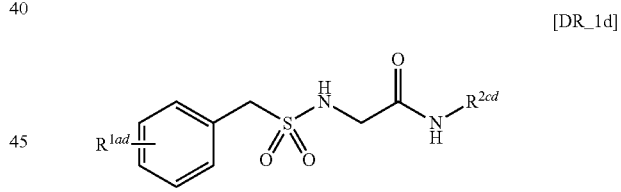

[DR_1d]

wherein $R^{1ad}$ is atoms or substituents selected from a hydrogen atom, a halogen atom, an alkyl group, and an alkoxy group, and $R^{2cd}$ is a substituted or unsubstituted aryl group or a substituted or unsubstituted aralkyl group.

An N-(substituted)-2-(substituted sulfamoylamino)acetamide derivative represented by the following general formula.

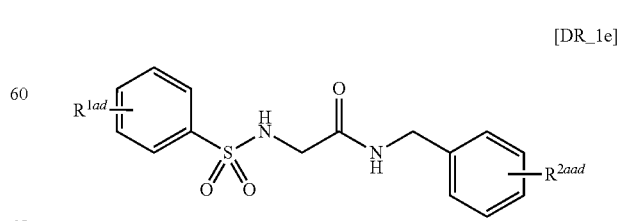

[DR_1e]

wherein $R^{1ad}$ is atoms or substituents selected from a hydrogen atom, a halogen atom, an alkyl group, and an alkoxy group, and $R^{2aad}$ is atoms or substituents selected from a hydrogen atom, a halogen atom, an alkyl group, an alkoxy group, and a hydroxyl group that is optionally protected.

[DR'_1]

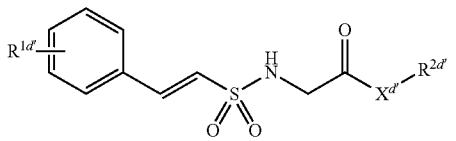

wherein $R^{1d'}$ is atoms or substituents selected from a hydrogen atom, a halogen atom, an alkyl group, an alkoxy group, and a hydroxyl group that is optionally protected, $R^{2d'}$ is a substituted or unsubstituted aryl group, a substituted or unsubstituted aralkyl group, or a substituted or unsubstituted arylacetamide group, and $X^{d'}$ is an oxygen atom or an imino group.

LW Compound

[LW_1a]

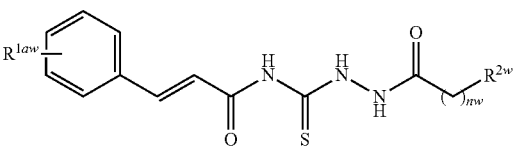

[LW_1b]

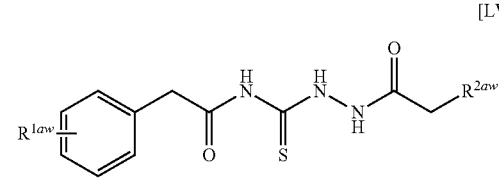

[LW_1c]

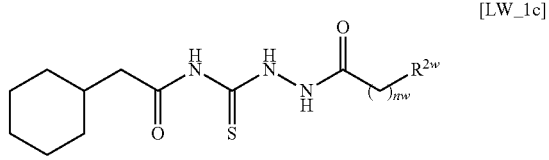

wherein $R^{1aw}$ is atoms or substituents selected from a halogen atom, an alkyl group, an alkoxy group, a nitro group, and a hydroxyl group that is optionally protected, $R^{2w}$ and $R^{2aw}$ are a substituted or unsubstituted aryl group, or a substituted or unsubstituted heterocyclic group that includes an oxygen atom or a sulfur atom as a ring atom, and nw is 0, 1, or 2.

Examples of a more preferable compound include the following compounds.

An N-[(acyl)hydrazinocarbothioyl]acetamide derivative represented by the following general formula.

[LW_1d]

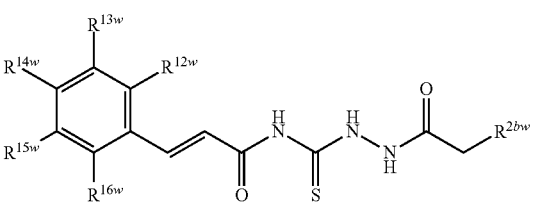

wherein $R^{13w}$ is a halogen atom, $R^{12w}$, $R^{14w}$, $R^{15w}$, and $R^{16w}$ are independently atoms or substituents selected from a hydrogen atom, a halogen atom, an alkyl group, an alkoxy group, and a nitro group, and $R^{21w}$ is a substituted or unsubstituted aryl group, or a substituted or unsubstituted heterocyclic group that includes an oxygen atom or a sulfur atom as a ring atom.

An N-[(acyl)hydrazinocarbothioyl]acetamide derivative represented by the following general formula.

[LW_1e]

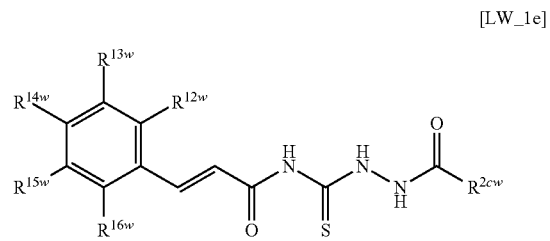

wherein $R^{2cw}$ is a substituted or unsubstituted heterocyclic group that includes an oxygen atom or a sulfur atom as a ring atom, and (1) $R^{12w}$, $R^{14w}$, and $R^{16w}$ are a hydrogen atom, and $R^{13w}$ and $R^{15w}$ are a halogen atom, or (2) $R^{13w}$, $R^{14w}$, and $R^{15w}$ are a hydrogen atom, and $R^{12w}$ and $R^{16w}$ are an alkoxy group.

An N-[(acyl)hydrazinocarbothioyl]acetamide derivative represented by the following general formula.

[LW_1f]

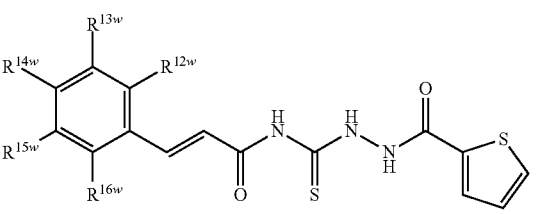

wherein (1) $R^{12w}$, $R^{14w}$, and $R^{16w}$ are a hydrogen atom, and $R^{13w}$ and $R^{15w}$ are a halogen atom, or (2) $R^{13w}$, $R^{14w}$, and $R^{15w}$ are a hydrogen atom, and $R^{12w}$ and $R^{16w}$ are an alkoxy group.

An N-[(acyl)hydrazinocarbothioyl]acetamide derivative represented by the following general formula.

[LW_1g]

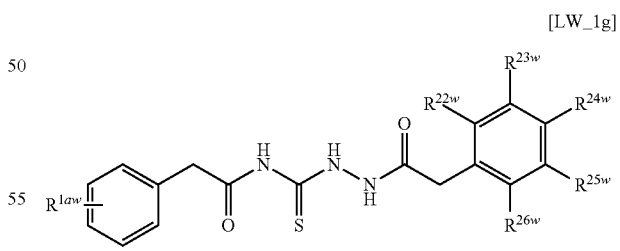

wherein $R^{1aw}$ is atoms or substituents selected from a halogen atom, an alkyl group, an alkoxy group, a nitro group, and a hydroxyl group that is optionally protected, and (1) $R^{24w}$ is a halogen atom, and $R^{22w}$, $R^{23w}$, $R^{25w}$, and $R^{26w}$ are a hydrogen atom, or (2) $R^{23w}$ is an alkyl group, and $R^{22w}$, $R^{24w}$, $R^{25w}$, and $R^{26w}$ are a hydrogen atom, or (3) $R^{22w}$ and $R^{26w}$ are a halogen atom, and $R^{23w}$, $R^{24w}$, and $R^{25w}$ are a hydrogen atom, or (4) $R^{23w}$ and $R^{25w}$ are a halogen atom, and $R^{22w}$, $R^{24w}$, and $R^{26w}$ are a hydrogen atom.

ED Compound

A benzenesulfonamide derivative represented by the following general formula.

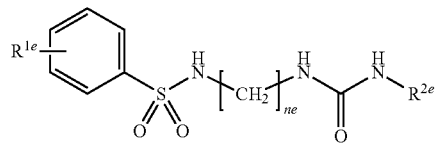

[ED_1a]

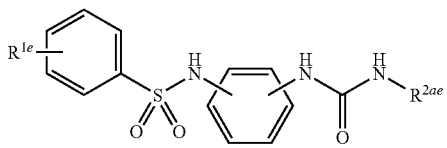

[ED_1b]

wherein $R^{1e}$ is atoms or substituents selected from a hydrogen atom, a halogen atom, an alkyl group, and an alkoxy group, $R^{2e}$ is a substituted or unsubstituted phenyl group or a substituted or unsubstituted tolylsulfonyl group, $R^{2ae}$ is a substituted or unsubstituted phenyl group, and ne is 2 or 3.

Examples of a more preferable compound include the following compounds.

A benzenesulfonamide derivative represented by the following general formula.

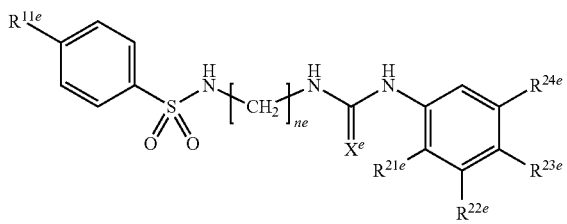

[ED_1aa]

wherein $R^{11e}$ is a hydrogen atom, an alkyl group, or an alkoxy group, $R^{21e}$ is a hydrogen atom, a halogen atom, or an alkyl group, $R^{22e}$ is a hydrogen atom or a halogen atom, $R^{23e}$ is a hydrogen atom or a halogen atom, $R^{24e}$ is a hydrogen atom, an alkyl group, or an alkoxy group, $X^e$ is an oxygen atom or a sulfur atom, and ne is 2 or 3, provided that a case where $R^{11e}$ is an alkyl group, $R^{21e}$ and $R^{23e}$ are a halogen atom, $R^{22e}$ and $R^{24e}$ are a hydrogen atom, $X^e$ is an oxygen atom, and ne is 2 is excluded.

A benzenesulfonamide derivative represented by the following general formula.

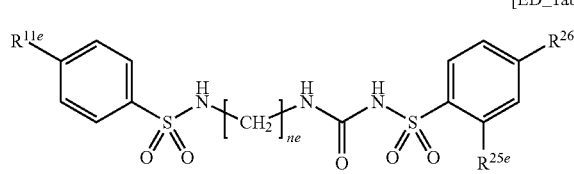

[ED_1ab]

wherein $R^{11e}$ is a hydrogen atom, an alkyl group, or an alkoxy group, $R^{25e}$ and $R^{26e}$ are independently a hydrogen atom or an alkyl group, and ne is 2 or 3.

A benzenesulfonamide derivative represented by the following general formula.

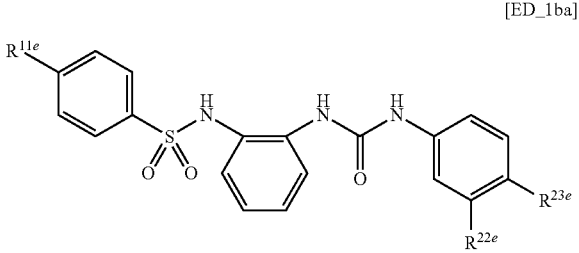

[ED_1ba]

wherein $R^{11e}$ is a hydrogen atom, an alkyl group, or an alkoxy group, and $R^{22e}$ and $R^{23e}$ are independently a hydrogen atom or a halogen atom.

The non-peptidic amide derivatives may be produced using the following methods, for example.

Production Method 1 (MM Compound)

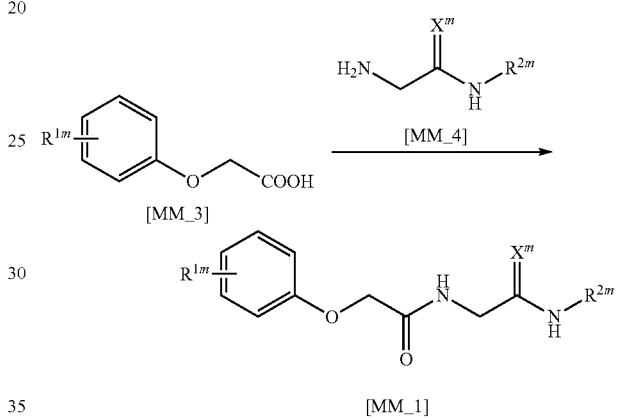

wherein $R^{1m}$ is atoms or substituents selected from a hydrogen atom, a halogen atom, an alkyl group, an alkoxy group, and a hydroxyl group that is optionally protected, $R^{2m}$ is a substituted or unsubstituted aryl group, a substituted or unsubstituted aralkyl group, or a substituted or unsubstituted cycloalkyl group, and $X^m$ is an oxygen atom or a sulfur atom.

The compound represented by the general formula [MM_1] can be produced by reacting the compound represented by the general formula [MM_4] with the compound represented by the general formula [MM_3] in the presence of a condensation agent.

A solvent used for the above reaction is not particularly limited as long as the solvent does not adversely affect the reaction. Examples of the solvent include halogenated hydrocarbons such as methylene chloride and chloroform; ethers such as tetrahydrofuran; and amides such as N,N-dimethylformamide.

Examples of the condensation agent used for the above reaction include carbonyldiimidazole, 1-ethyl-3-(3-dimethylaminopropyl)carbodiimide (EDC), and the like.

1-Hydroxybenzotriazole (HOBt) and 3,4-dihydro-3-hydroxy-4-oxo-1,2,3-benzotriazine (HOOBt) may be used in combination as additives.

The condensation agent is used in a molar ratio of 1 or more (preferably 1 to 10) with respect to the compound represented by the general formula [3].

The above reaction is normally carried out at 0 to 200° C. (preferably 10 to 150° C.) for 10 minutes to 24 hours.

The compound represented by the general formula [MM_3] can be produced using a known method (see the following documents, for example).

Synth. Commun 2004, 34, 377-382.
Lett. Org. Chem. 2011, 8, 234-241.
Org. Lett. 2010, 12, 4571-4575.
U.S. Pat. Appl. Publ., 20070141113, 21 Jun. 2007.
Faming Zhuanli Shenqing Gongkai Shuomingshu, 101314576, 3 Dec. 2008.
J. Am. Chem. Soc. 2007, 129, 3981-3929.

The compound represented by the general formula [MM_4] can be produced using a known method (see the following documents, for example).
Eur. J. Org. Chem. 2008, 23, 3976-3983.
Eur. J. Med. Chem. 1996, 31, 497-505.
PCT Int. Appl. (2000), WO 2000071507 A2 20001130.
J. Org. Chem. 2011, 76, 9278-9293.
J. Med. Chem. 2009, 52, 5005-5008.
Org. Lett. 2010, 12, 2718-2721.
PCT Int. Appl. (2010), WO 2010067067 A1 20100617.
PCT Int. Appl., 2007141473, 13 Dec. 2007.

It is possible to use an arbitrary isomer (e.g., optical isomer, geometric isomer, or tautomer) of the compound represented by the general formula [MM_3] and the compound represented by the general formula [MM_4]. A hydrate, a solvate, or an arbitrary crystalline form thereof may be used.

These compounds may be used directly for the subsequent reaction without performing an isolation operation.

The compound represented by the general formula [MM_1] thus obtained can be isolated and purified using a normal method such as extraction, crystallization, distillation, and column chromatography.

Production Method 2 (DR Compound and DR' Compound)

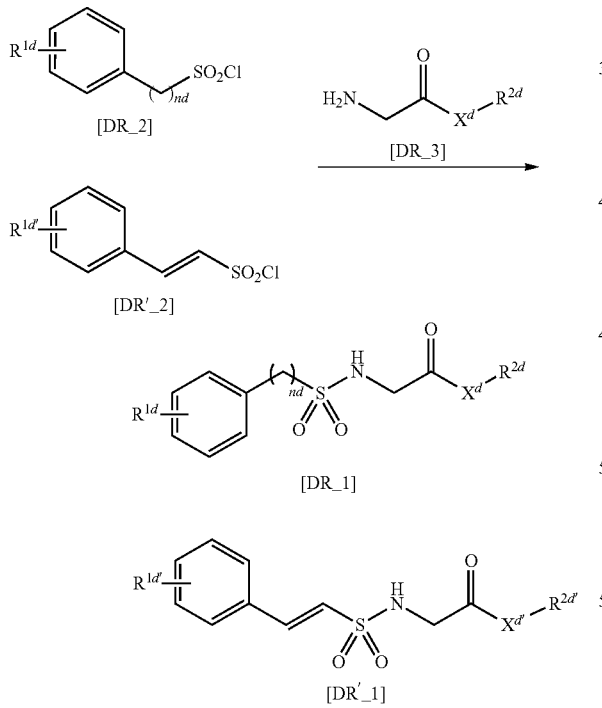

wherein $R^{1d}$ is atoms or substituents selected from a hydrogen atom, a halogen atom, an alkyl group, an alkoxy group, and a hydroxyl group that is optionally protected, $R^{2d}$ is a substituted or unsubstituted aryl group, a substituted or unsubstituted aralkyl group, or a substituted or unsubstituted arylacetamide group, $X^d$ is an oxygen atom or an imino group, and nd is 0 or 1.

The compound represented by the general formula [DR_1] or [DR'_1] can be produced by reacting the compound represented by the general formula [DR_3] with the compound represented by the general formula [DR_2] or [DR'_2] in the presence of a base.

A solvent used for the above reaction is not particularly limited as long as the solvent does not adversely affect the reaction. Examples of the solvent include halogenated hydrocarbons such as methylene chloride and chloroform; ethers such as tetrahydrofuran; and the like.

Examples of the base used for the above reaction include organic bases such as diethylamine, triethylamine, and N,N-dimethyl-4-aminopyridine.

The base is used in a molar ratio of 0.1 to 2 with respect to the compound represented by the general formula [DR_3].

The above reaction is normally carried out at 0 to 200° C. (preferably 10 to 150° C.) for 10 minutes to 24 hours.

The compound represented by the general formula [DR_2] or [DR'_2] can be produced using a known method (see the following documents, for example).
J. Med. Chem., 2011, 54, 2738-2744.
ACS Chem. Neurosci., 2010, 1, 155-164.
US2008/0269280 A1

The compound represented by the general formula [DR_3] can be produced using a known method (see the following document, for example).
Tetrahedron Lett., 2011, 52, 2579-2582.

It is possible to use an arbitrary isomer (e.g., optical isomer, geometric isomer, or tautomer) of the compound represented by the general formula [DR_2], the compound represented by the general formula [DR'_2], and the compound represented by the general formula [DR_3]. A hydrate, a solvate, or an arbitrary crystalline form thereof may be used.

These compounds may be used directly for the subsequent reaction without performing an isolation operation.

The compound represented by the general formula [DR_1] or [DR'_1] thus obtained can be isolated and purified using a normal method such as extraction, crystallization, distillation, and column chromatography.

Production Method 3 (LW Compound)

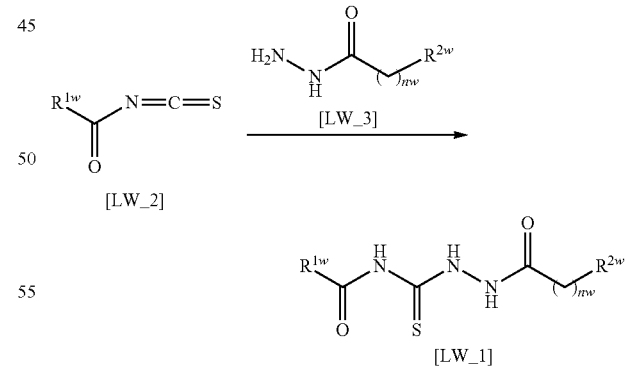

wherein $R^{1w}$ is a substituted or unsubstituted styryl group, a substituted or unsubstituted benzyl group, or a substituted or unsubstituted cyclohexylmethyl group, $R^{2w}$ is a substituted or unsubstituted aryl group, or a substituted or unsubstituted heterocyclic group that includes an oxygen atom or a sulfur atom as a ring atom, and nw is 0, 1, or 2.

The compound represented by the general formula [LW_1] can be produced by reacting the compound represented by the general formula [LW_2] with the compound represented by the general formula [LW_3].

A solvent used for the above reaction is not particularly limited as long as the solvent does not adversely affect the reaction. Examples of the solvent include halogenated hydrocarbons such as methylene chloride and chloroform; ethers such as tetrahydrofuran; and the like.

The above reaction is normally carried out at 0 to 200° C. (preferably 10 to 150° C.) for 10 minutes to 24 hours.

The compound represented by the general formula [LW_2] and the raw material compound can be produced using a known method (see the following documents, for example).
Tetrahedron, 2011, 67, 8120-8130.
Bioorg. Med. Chem., 2004, 13, 433-441.
Synthesis, 2008, 279-285.
J. Org. Chem., 2008, 73, 5766-5775.
Org. Biomol. Chem., 2009, 7, 4062-4066.
Chem. Eur. J., 2000, 6, 3386-3390.
Synth. Commun., 1980, 10, 37-42.
Synth. Commun., 2002, 32, 195-201.
J. Med. Chem., 1993, 36, 2381-9.
J. Org. Chem., 1995, 60, 1981-4.
J. Org. Chem., 1999, 64, 3975-3978.
WO 2004046122 A2
WO 2001092239 A1
Bioorg. Med. Chem. Lett., 2011, 21, 1102-1104.
Chem. Pep. Chem. Zvesti, 1974, 28, 693-6.
Chem. Pep. Chem. Zvesti, 1969, 23, 173-80.
J. Med. Chem., 2006, 49, 2186-2192.
Bioorg. Med. Chem. Lett., 2008, 18, 1945-1951.
WO 2009125597 A1
WO 2007054831 A2

The compound represented by the general formula [LW_3] can be produced using a known method. For example, the compound represented by the general formula [LW_3] can be produced by reacting hydrazine monohydrate with a carboxylic acid ester.

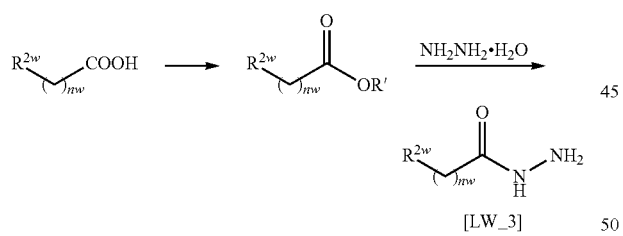

wherein $R^{2w}$ is a substituted or unsubstituted aryl group, or a substituted or unsubstituted heterocyclic group that includes an oxygen atom or a sulfur atom as a ring atom, R' is an alkyl group, and nw is 0, 1, or 2.

It is possible to use an arbitrary isomer (e.g., optical isomer, geometric isomer, or tautomer) of the compound represented by the general formula [LW_2] and the compound represented by the general formula [LW_3]. A hydrate, a solvate, or an arbitrary crystalline form thereof may be used.

These compounds may be used directly for the subsequent reaction without performing an isolation operation.

The compound represented by the general formula [LW_1] thus obtained can be isolated and purified using a normal method such as extraction, crystallization, distillation, and column chromatography.

Production Method 4 (ED Compound)

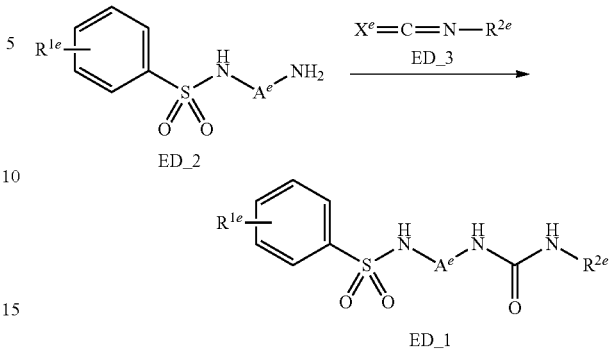

wherein $R^{1e}$ is atoms or substituents selected from a hydrogen atom, a halogen atom, an alkyl group, and an alkoxy group, $R^{2e}$ is a substituted or unsubstituted phenyl group or a substituted or unsubstituted tolylsulfonyl group, and $A^e$ is an alkylene group or a phenylene group.

The compound represented by the general formula [ED_1] can be produced by reacting the compound represented by the general formula [ED_2] with the compound represented by the general formula [ED_3].

A solvent used for the above reaction is not particularly limited as long as the solvent does not adversely affect the reaction. Examples of the solvent include halogenated hydrocarbons such as methylene chloride and chloroform; ethers such as tetrahydrofuran; and the like.

The above reaction is normally carried out at 0 to 200° C. (preferably 10 to 100° C.) for 10 minutes to 24 hours.

The compound represented by the general formula [ED_2] and the raw material compound can be produced using a known method. For example, the compound represented by the general formula [ED_2] and the raw material compound can be produced by reacting the benzenesulfonyl chloride represented by the general formula [ED_4] with the diamine represented by the general formula [ED_5] under known conditions.

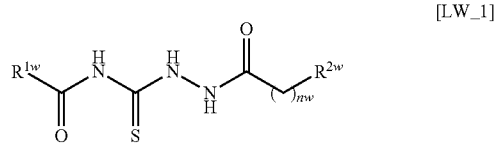

[LW_1]

wherein $R^{1e}$ is atoms or substituents selected from a hydrogen atom, a halogen atom, an alkyl group, and an alkoxy group, and $A^e$ is an alkylene group or a phenylene group.

It is possible to use an arbitrary isomer (e.g., optical isomer, geometric isomer, or tautomer) of the compound represented by the general formula [ED_2], the compound represented by the general formula [ED_3], the compound represented by the general formula [ED_4], and the compound represented by the general formula [ED_5]. A hydrate, a solvate, or an arbitrary crystalline form thereof may be used.

These compounds may be used directly for the subsequent reaction without performing an isolation operation.

The compound represented by the general formula [ED_1] thus obtained can be isolated and purified using a normal method such as extraction, crystallization, distillation, and column chromatography.

The compounds according to the invention may be mixed with various excipients and additives such as a solvent, an extender, a tonicity agent, a solubilizer, an emulsifier, a suspending agent, a thickener, an absorption promoter, a gelling/coagulation promoter, an optical stabilizer, a preservative, an emulsification/suspension/dispersion stabilizer, a coloring inhibitor, a defoamer, a soothing agent, a buffer, and a pH adjusting agent to prepare a drug preparation such as an injection or a suppository.

The preparation may be administered using an arbitrary method. The administration method is appropriately determined corresponding to the form of the preparation, the age, the sex, and other conditions of the patient, and the severity of the symptoms.

The dose of the effective component of the preparation is appropriately selected corresponding to the application, the age and the sex of the patient, the disease, and the like. The preparation is normally administered in an amount of 0.1 to 500 mg per day per adult at a time or several times a day.

The pharmacological action of the representative compounds according to the invention is described below.

Test Example 1

Enzyme Activity Measurement Method

The serine racemase (SR) activity inhibition effect of the compound was determined based on (1) the L-serine racemization reaction and (2) quantitative determination of D-serine produced (see below).

(1) L-Serine Racemization Reaction

Recombinant SR (3.7 μg) that had been expressed by *Escherichia coli* and purified was reacted at 37° C. for 8 hours or more in 125 μL of a reaction mixture including 100 mM HEPES (pH: 8.0), 1 mM $MgCl_2$, 10 μM PLP, 1 mM ATP, 20 mM L-serine, 5 mM DTT, and the compound (1 to 0.01 mM) dissolved in DMSO in accordance with the method proposed by Strisovsky et al. (Biochemistry, 44:13091-13100, 2005).

(2) Quantitative Determination of D-serine

D-serine was quantitatively determined in accordance with the method proposed by Ito et al. (Analytical Biochemistry, 371: 167-172, 2007).

A solution including 25 μL of 100 mM HEPES (pH: 8.0), 20 μM PLP, and 2 μg of recombinant D-serine dehydratase 1 (Dsd1) was added to 25 μL of the reaction mixture (see (1)), and the mixture was reacted at 30° C. for 30 minutes.

In order to measure pyruvic acid produced from D-serine by Dsd1 using a colorimetric reaction, 50 μL of 0.05% DNP/2M HCl was added to 50 μL of the reaction solution, and the mixture was reacted at 30° C. for 5 minutes. After the addition of 100 μL of ethanol and 125 μL of 10 M NaOH, the mixture was sufficiently mixed, and reacted at room temperature for 10 minutes, and the absorbance at a wavelength of 515 nm was measured using a spectrophotometer.

The results are shown in Tables 1 and 2.

Note that each numerical value in parentheses in Tables 1 to 8 is the value of malonic acid (control).

TABLE 1

| MM | structure | % human 1 mM | % human 0.1 mM |
|---|---|---|---|
| 1 | (phenyl-O-CH2-C(O)-NH-CH2-C(O)-NH-(2-Me-4-OMe-phenyl)) | 62 (63) | 87 (84) |
| 3 | (4-Br-phenyl-O-CH2-C(O)-NH-CH2-C(O)-NH-(2-Me-4-OMe-phenyl)) | 35 (63) | 69 (84) |
| 6 | (4-F-phenyl-O-CH2-C(O)-NH-CH2-C(O)-NH-(2-Me-4-OMe-phenyl)) | 48 (63) | 82 (84) |
| 7 | (4-F-phenyl-O-CH2-C(O)-NH-CH2-C(O)-NH-(4-I-phenyl)) | 55 (63) | 71 (84) |
| 10 | (4-F-phenyl-O-CH2-C(O)-NH-CH2-C(O)-NH-(4-Br-phenyl)) | 44 (57) | 80 (84) |

TABLE 1-continued

| MM | structure | % human 1 mM | % human 0.1 mM |
|---|---|---|---|
| 11 | 4-BrC6H4-O-CH2-C(O)-NH-CH2-C(O)-NH-C6H4-4-OMe | 55 (57) | 75 (84) |
| 13 | 4-BrC6H4-O-CH2-C(O)-NH-CH2-C(O)-NH-cyclohexyl | 53 (57) | 99 (110) |
| 15 | 4-BrC6H4-O-CH2-C(O)-NH-CH2-C(O)-NH-(2,6-F2-C6H3) | 49 (57) | 87 (110) |
| 16 | 4-BrC6H4-O-CH2-C(O)-NH-CH2-C(O)-NH-CH2-C6H5 | 55 (57) | 100 (110) |
| 19 | 3-MeO-C6H4-O-CH2-C(O)-NH-CH2-C(O)-NH-(2-Me-4-OMe-C6H3) | 56 (57) | 96 (110) |

TABLE 2

| MM | structure | % human 1 mM | % human 0.1 mM |
|---|---|---|---|
| 24 | 4-F-C6H4-O-CH2-C(O)-NH-CH2-C(O)-NH-(2,6-F2-C6H3) | 50 (54) | 93 (110) |
| 25 | 4-Br-C6H4-O-CH2-C(O)-NH-CH2-C(S)-NH-(2,6-F2-C6H3) | 81 (77) | 86 (110) |
| 26 | 4-MeO-C6H4-O-CH2-C(O)-NH-CH2-C(S)-NH-(2,6-F2-C6H3) | 97 (77) | 90 (110) |

TABLE 2-continued

| MM | structure | % human 1 mM | % human 0.1 mM |
|---|---|---|---|
| 27 | 4-bromophenoxy-CH2-C(O)-NH-CH2-C(O)-NH-CH2-(2-methylphenyl) | 68 (57) | 92 (110) |
| 28 | 4-bromophenoxy-CH2-C(O)-NH-CH2-C(O)-NH-CH2-(4-bromophenyl) | 80 (57) | 93 (110) |
| 29 | 4-bromophenoxy-CH2-C(O)-NH-CH2-C(O)-NH-CH2-(2-fluoro-4-bromophenyl) | 69 (57) | 85 (110) |
| 30 | 4-bromophenoxy-CH2-C(O)-NH-CH2-C(O)-NH-(3-bromophenyl) | — | 77 (87) |
| 31 | 4-methoxyphenoxy-CH2-C(O)-NH-CH2-C(O)-NH-(3-bromophenyl) | — | 84 (87) |
| 33 | 4-bromophenoxy-CH2-C(O)-NH-CH2-C(O)-NH-(3-nitrophenyl) | — | 83 (87) |
| 35 | 4-hydroxyphenoxy-CH2-C(O)-NH-CH2-C(O)-NH-(2,6-difluorophenyl) | — | 78 (62) |

TABLE 3

| DR | structure | % human (0.1 mM) |
|---|---|---|
| 1 | benzyl-SO2-NH-CH2-C(O)-NH-(2,6-difluorophenyl) | 77 (87) |
| 3 | benzyl-SO2-NH-CH2-C(O)-NH-CH(Me)-phenyl | 85 (87) |
| 4 | 4-Me-phenyl-SO2-NH-CH2-C(O)-NH-CH(Me)-phenyl | 86 (87) |
| 5 | benzyl-SO2-NH-CH2-C(O)-O-CH2-phenyl | 65 (87) |
| 6 | 4-Me-phenyl-SO2-NH-CH2-C(O)-O-CH2-phenyl | 84 (87) |
| 10 | 4-Me-phenyl-SO2-NH-CH2-C(O)-NH-CH2-(4-Br-phenyl) | 75 (87) |
| 11 | 4-Me-phenyl-SO2-NH-CH2-C(O)-NH-CH2-(2-F-4-Br-phenyl) | 67 (87) |
| 12 | benzyl-SO2-NH-CH2-C(O)-NH-(3-Br-phenyl) | 63 (87) |
| 13 | 4-Me-phenyl-SO2-NH-CH2-C(O)-NH-(3-Br-phenyl) | 52 (87) |

TABLE 3-continued

| DR | structure | % human (0.1 mM) |
|---|---|---|
| 18 | 4-Me-C6H4-SO2-NH-CH2-C(O)-NH-(3-NO2-C6H4) | 62 (87) |
| 19 | 4-Me-C6H4-SO2-NH-CH2-C(O)-NH-NH-C(O)-CH2-(4-F-C6H4) | 60 (87) |
| 20 | 4-Me-C6H4-SO2-NH-CH2-C(O)-NH-(4-OBn-C6H4) | 56 (62) |
| 24 | 4-MeO-C6H4-SO2-NH-CH2-C(O)-NH-(3-Br-C6H4) | 59 (62) |
| 29 | 4-Cl-C6H4-SO2-NH-CH2-C(O)-NH-(2-Br-C6H4) | 60 (71) |
| 35 | (E)-4-Me-C6H4-CH=CH-SO2-NH-CH2-C(O)-NH-(4-OBn-C6H4) | 63 (75) |

TABLE 4

R$^{1w}$-C(O)-NH-C(=S)-NH-NH-C(O)-(CH2)$_{nw}$-R$^{2w}$

| LW | R$^{1w}$ | nw | R$^{2w}$ | % human 1 mM |
|---|---|---|---|---|
| 1 | 4-Cl-C6H4-CH=CH-(propenyl) | 1 | 2-thienyl | 23 (64 MaI) |
| 2 | 2,4,6-triCl-C6H2-CH=CH-(propenyl) | 1 | 2-thienyl | 33 (64 MaI) |
| 3 | 4-O2N-C6H4-CH=CH-(propenyl) | 1 | 2-thienyl | 35 (64 MaI) |
| 4 | 4-Me-C6H4-CH=CH-(propenyl) | 1 | 2-thienyl | 24 (64 MaI) |

TABLE 4-continued

![structure: R^1w-C(=O)-NH-C(=S)-NH-NH-C(=O)-(CH2)nw-R^2w]

| LW | R^1w | nw | R^2w | % human 1 mM |
|---|---|---|---|---|
| 6 | 2,4-dimethoxy-(1-propenyl)phenyl | 1 | 2-methylthiophene | 27 (64 MaI) |
| 7 | 3,5-dibromo-(1-propenyl)phenyl | 1 | 2-methylthiophene | 28 (64 MaI) |
| 9 | 4-phenyl-(1-propenyl)phenyl | 1 | 2-methylthiophene | 55 (75 MaI) |
| 13 | 4-(trifluoromethyl)-(1-propenyl)phenyl | 1 | 2-methylthiophene | 44 (63 MaI) |
| 16 | 4-fluoro-(1-propenyl)phenyl | 0 | 2-methylthiophene | 46 (63 MaI) |
| 19 | 2,6-dimethoxy-(1-propenyl)phenyl | 0 | 2-methylthiophene | 31 (63 MaI) |
| 20 | 3,5-dibromo-(1-propenyl)phenyl | 0 | 2-methylthiophene | 52 (63 MaI) |

TABLE 5

![structure: R^1w-C(=O)-NH-C(=S)-NH-NH-C(=O)-(CH2)nw-R^2w]

| LW | R^1w | nw | R^2w | % human 1 mM |
|---|---|---|---|---|
| 12 | 4-fluoro-(1-propenyl)phenyl | 1 | phenyl | 45 (63 MaI) |
| 14 | 2,4,6-trifluoro-(1-propenyl)phenyl | 1 | phenyl | 33 (63 MaI) |
| 15 | 3,5-dibromo-(1-propenyl)phenyl | 1 | phenyl | 20 (63 MaI) |
| 17 | 2,6-dimethoxy-(1-propenyl)phenyl | 1 | phenyl | 24 (64 MaI) |
| 21 | 3,5-dibromo-(1-propenyl)phenyl | 1 | 4-fluorophenyl | 49 (57 MaI) |
| 23 | 3,5-dibromo-(1-propenyl)phenyl | 0 | phenyl | 31 (57 MaI) |
| 24 | 3,5-dibromo-(1-propenyl)phenyl | 1 | 3-methylphenyl | 24 (54 MaI) |
| 26 | 3,5-dibromo-(1-propenyl)phenyl | 1 | 3-methoxyphenyl | 31 (54 MaI) |
| 31 | 3,5-dibromo-(1-propenyl)phenyl | 2 | phenyl | 31 (57 MaI) |

TABLE 6
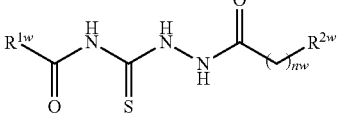
| LW | R$^{1w}$ | nw | R$^{2w}$ | % human 1 mM |
|---|---|---|---|---|
| 18 | 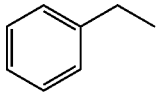 | 1 | 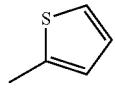 | 61 (63 MaI) |
| 22 | 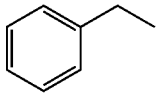 | 1 | 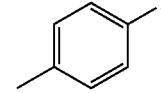 | 0 (57 MaI) |
| 25 | 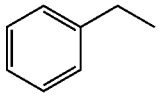 | 1 | 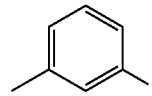 | 45 (54 MaI) |
| 27 | 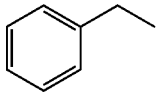 | 1 | 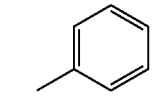 | 41 (54 MaI) |
| 28 | 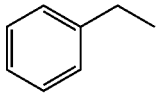 | 1 | 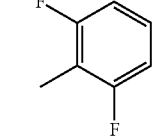 | 74 (77 MaI) |
TABLE 6-continued
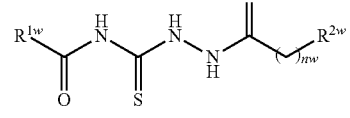
| LW | R$^{1w}$ | nw | R$^{2w}$ | % human 1 mM |
|---|---|---|---|---|
| 29 | 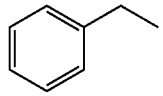 | 1 | 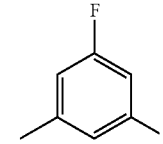 | 67 (77 MaI) |
| 30 | 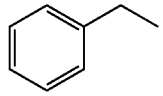 | 2 | 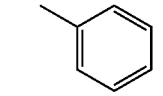 | 70 (57 MaI) |
| 32 | 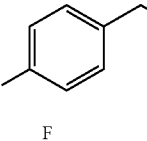 | 1 | 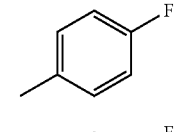 | *67 (*87 MaI) |
| 33 | 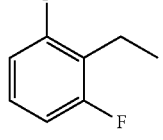 | 1 | 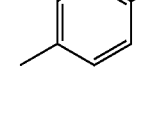 | *66 (*87 MaI) |
| 34 | 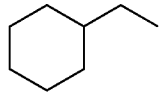 | 1 | 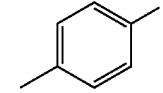 | *67 (*62 MaI) |
*% human 0.1 mM
TABLE 7
| ED | structure | % human (1 mM) |
|---|---|---|
| 1 | 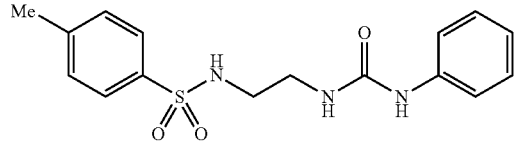 [SMILES: Cc1ccc(S(=O)(=O)NCCNC(=O)Nc2ccccc2)cc1] | 79 (85 MaI) |
| 3 | 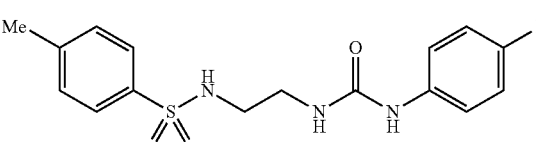 | 76 (85 MaI) |
| 4 | 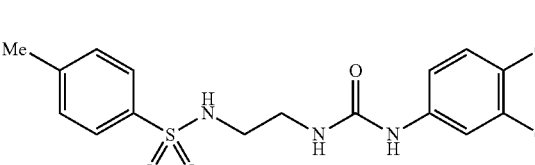 | 52 (85 MaI) |

TABLE 7-continued

| ED | structure | % human (1 mM) |
|---|---|---|
| 6 | 4-Me-C6H4-SO2-NH-CH2CH2-NH-C(=S)-NH-(2-MeO-C6H4) | 76 (85 MaI) |
| 7 | 4-Me-C6H4-SO2-NH-CH2CH2-NH-C(=O)-NH-(3-MeO-C6H4) | 64 (85 MaI) |
| 9 | 4-Me-C6H4-SO2-NH-CH2CH2-NH-C(=O)-NH-SO2-(2-Me-C6H4) | 62 (85 MaI) |
| 10 | 4-Me-C6H4-SO2-NH-CH2CH2-NH-C(=O)-NH-(2,4-diCl-C6H3) | 59 (85 MaI) |
| 12 | 4-Me-C6H4-SO2-NH-CH2CH2-NH-C(=S)-NH-(2-Me-C6H4) | 58 (85 MaI) |
| 13 | 4-Me-C6H4-SO2-NH-CH2CH2-NH-C(=S)-NH-(5-Me-2-MeO-C6H3) | 63 (85 MaI) |
| 14 | 4-Me-C6H4-SO2-NH-CH2CH2-NH-C(=S)-NH-CH2CH2CH2-OMe | 86 (78 MaI) |
| 15 | 4-Me-C6H4-SO2-NH-CH2CH2-NH-C(=S)-NH-(2-Cl-C6H4) | 69 (78 MaI) |
| 16 | 4-MeO-C6H4-SO2-NH-CH2CH2-NH-C(=O)-NH-(3,4-diCl-C6H3) | 61 (78 MaI) |

TABLE 7-continued

| ED | structure | % human (1 mM) |
|----|-----------|----------------|
| 17 | 4-Br-C6H4-SO2-NH-CH2CH2-NH-C(O)-NH-(3,4-diCl-C6H3) | 49 (78 MaI) |
| 20 | 4-Me-C6H4-SO2-NH-CH2CH2-NH-C(O)-NH-(2-Cl-4-Br-C6H3) | 57 (78 MaI) |
| 22 | 4-Br-C6H4-SO2-NH-CH2CH2CH2-NH-C(O)-NH-(3,4-diCl-C6H3) | 55 (78 MaI) |
| 24 | 4-MeO-C6H4-SO2-NH-CH2CH2CH2-NH-C(O)-NH-(3,4-diCl-C6H3) | 55 (78 MaI) |

TABLE 8

| ED | structure | % human (1 mM) |
|----|-----------|----------------|
| 25 | 4-Me-C6H4-SO2-NH-(2-NH-C(O)-NH-(3,4-diCl-C6H3))-C6H4 | 49 (78 MaI) |
| 26 | 4-Me-C6H4-SO2-NH-(2-NH-C(O)-NH-(4-F-C6H4))-C6H4 | 54 (78 MaI) |
| 27 | 4-Br-C6H4-SO2-NH-(2-NH-C(O)-NH-(3,4-diCl-C6H3))-C6H4 | 48 (51 MaI) ‡ |
| 31 | 4-MeO-C6H4-SO2-NH-(2-NH-C(O)-NH-(3,4-diCl-C6H3))-C6H4 | 58 (51 MaI) ‡ |

TABLE 8-continued

| ED | structure | % human (1 mM) |
|---|---|---|
| 36 | 4-Cl-C6H4-SO2-NH-C6H4-NH-C(O)-NH-(2,4-diCl-C6H3) | 46 (51 MaI) ‡ |
| 37 | 4-Me-C6H4-CH=CH-SO2-NH-C6H4-NH-C(O)-NH-(3,4-diCl-C6H3) | 48 (51 MaI) ‡ |

‡: % human (0.3 mM)

Advantageous Effects of the Invention

The non-peptidic amide derivatives have serine racemase inhibitory activity. Therefore, the non-peptidic amide derivatives make it possible to adjust the activity of the NMDAR, and may be used as a novel therapeutic agent for treating neurodegenerative diseases and hyperexcitable brain conditions.

DESCRIPTION OF EMBODIMENTS

The invention is further described below by way of reference examples and examples.

Note that the invention is not limited to the following examples.

The abbreviations in the chemical structural formulas have the following meanings.

Me: methyl, Ph: phenyl, Bn: benzyl, Boc: butoxycarbonyl

Reference Example 1

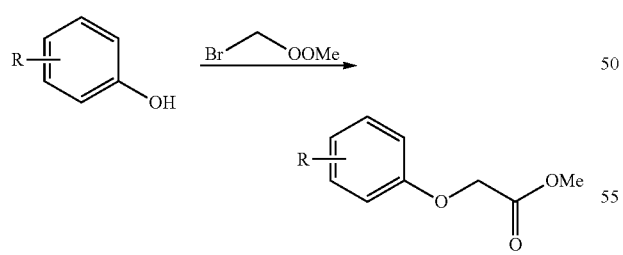

Methyl bromoacetate (0.10 mL, 1 mmol) and potassium carbonate (207 mg, 1.5 mmol) were sequentially added to a dimethylformamide (3 mL) solution of a phenol compound (1.0 mmol) in an argon atmosphere, and the mixture was stirred at 80° C. overnight.

The reaction mixture was diluted with ethyl acetate (10 mL), and filtered through celite, and the solvent was evaporated.

The residue was purified by silica gel column chromatography (15 g, hexane:acetone=50:1 to 40:1) to obtain a methyl ester compound.

(4-Bromophenoxy)acetic acid methyl ester

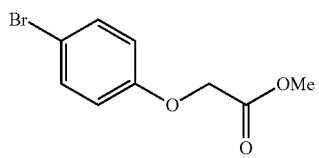

(4-Bromo-phenoxy)-acetic acid methyl ester

Yield: 100%
Reference: Synth. Commun., 2004, 34, 377-382.

(4-Chlorophenoxy)acetic acid methyl ester

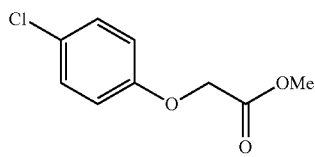 [SMILES: COC(=O)COc1ccc(Cl)cc1]

(4-Chloro-phenoxy)-acetic acid methyl ester

Yield: 90%
Reference: Synth. Commun., 2004, 34, 377-382.

(4-Fluorophenoxy)acetic acid methyl ester

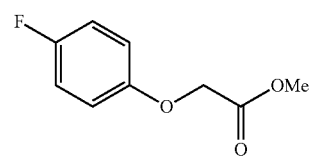 [SMILES: COC(=O)COc1ccc(F)cc1]

(4-Fluoro-phenoxy)-acetic acid methyl ester

Yield: 84%
Reference: Lett. Org. Chem., 2011, 8, 234-241.

(4-Methoxyphenoxy)acetic acid methyl ester

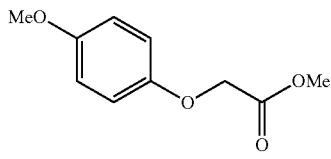 [SMILES: COC(=O)COc1ccc(OC)cc1]

(4-Methoxy-phenoxy)-acetic acid methyl ester

Yield: 97%
Reference: Org. Lett., 2010, 12, 4571-4575.

(4-Benzyloxyphenoxy)acetic acid methyl ester

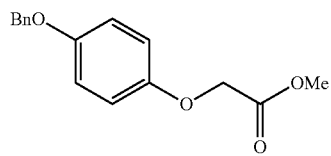 [SMILES: COC(=O)COc1ccc(Oc2ccccc2)cc1]

(4-Benzyloxy-phenoxy)-acetic acid methyl ester

Yield: 89%
Reference: US20070141113

(4-Phenoxyphenoxy)acetic acid methyl ester

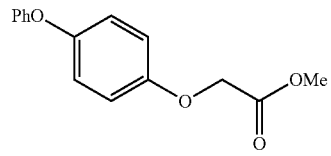

(4-Phenoxy-phenoxy)-acetic acid methyl ester

Yield: 97%
Reference: Faming Zhuanli Shenqing Gongkai Shuomingshu, 101314576, 3 Dec. 2008.

(3-Methoxyphenoxy)acetic acid methyl ester

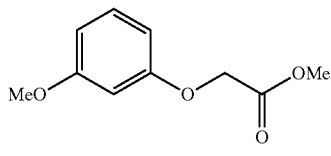 [SMILES: COC(=O)COc1cccc(OC)c1]

(3-Methoxy-phenoxy)-acetic acid methyl ester

Yield: 92%
Reference: J. Am. Chem. Soc., 2007, 129, 3981-3929.

m-Tolyloxyacetic acid methyl ester

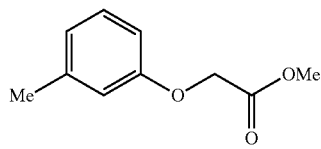 [SMILES: COC(=O)COc1cccc(C)c1]

m-Tolyloxy-acetic acid methyl ester

Yield: 89%
Reference: J. Am. Chem. Soc., 2007, 129, 3981-3929.

Phenoxyacetic acid methyl ester

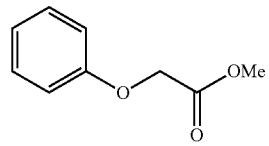 [SMILES: COC(=O)COc1ccccc1]

Phenoxy-acetic acid methyl ester

Yield: 85%
Reference: Lett. Org. Chem., 2011, 8, 234-241.

Reference Example 2

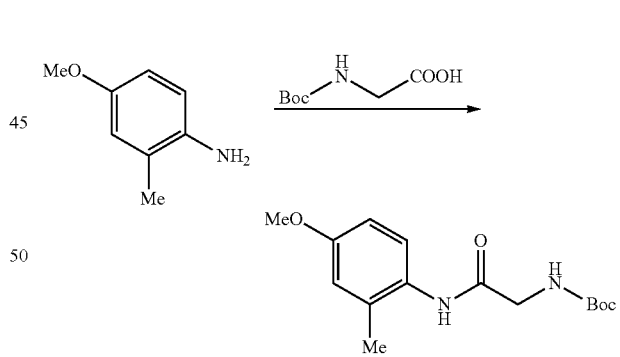

Triethylamine (0.21 mL, 1.5 mmol), N-(tert-butoxycarbonyl)glycine (175 mg, 1.0 mmol), EDC (192 mg, 1.0 mmol), and DMAP (12 mg, 0.1 mmol) were sequentially added to a methylene chloride (5 mL) solution of 2-methyl-4-methoxyaniline (0.13 mL, 1.0 mmol) in an argon atmosphere, and the mixture was stirred at room temperature for 5 hours.

After evaporating the solvent, the residue was purified by silica gel column chromatography (20 g, hexane:acetone=30:1 to 2:1) to obtain [(4-methoxy-2-methylphenylcarbamoyl)methyl]carbamic acid tert-butyl ester (290 mg) as a colorless oily substance.

¹H-NMR (400 MHz, CDCl₃): δ 1.48 (9H, s), 2.22 (3H, s), 3.78 (3H, s), 3.93 (2H, d, J=6.1 Hz), 5.21 (1H, br), 6.73-6.75 (2H, m), 7.59 (1H, d, J=9.3 Hz), 7.79 (1H, br)

¹³C-NMR (100 MHz, CDCl₃): δ 17.85, 28.21, 45.09, 55.23, 80.32, 111.34, 115.82, 125.26, 128.09, 132.42, 156.44, 157.17, 168.34

IR (neat): 1680, 3290 cm⁻¹

MS (EI): m/z 294 (M⁺)

Yield: 99%

The following compounds were obtained via a similar reaction.

[(4-Iodophenylcarbamoyl)methyl]carbamic acid tert-butyl ester

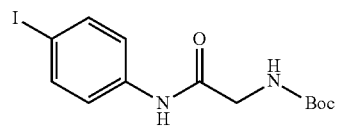 [SMILES: CC(C)(C)OC(=O)NCC(=O)Nc1ccc(I)cc1]

[(4-Iodo-phenylcarbamoyl)-methyl]carbamic acid tert-butyl ester

Yield: 98%
Reference: Eur. J. Org. Chem., 2008, 23, 3976-3983.

[(4-Fluorophenylcarbamoyl)methyl]carbamic acid tert-butyl ester

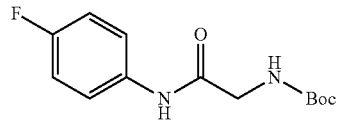

[(4-Fluoro-phenylcarbamoyl)-methyl]-carbamic acid tert-butyl ester

Yield: 100%
Reference: Eur. J. Med. Chem., 1996, 31, 497-505.

[(4-Bromophenylcarbamoyl)methyl]carbamic acid tert-butyl ester

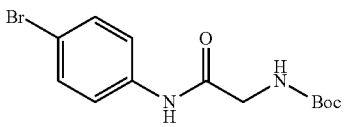

[(4-Bromo-phenylcarbamoyl)-methyl]-carbamic acid tert-butyl ester

Yield: 97%
Reference: WO2000/071507

[(4-Methoxyphenylcarbamoyl)methyl]carbamic acid tert-butyl ester

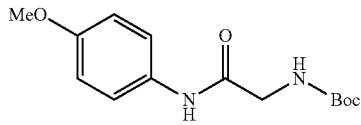 [SMILES: COc1ccc(NC(=O)CNC(=O)OC(C)(C)C)cc1]

[(4-Methoxy-phenylcarbamoyl)-methyl]-carbamic acid tert-butyl ester

Yield: 68%
Reference: J. Org. Chem., 2011, 76, 9278-9293.

Cyclohexylcarbamoylmethylcarbamic acid tert-butyl ester

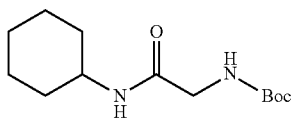 [SMILES: CC(C)(C)OC(=O)NCC(=O)NC1CCCCC1]

Cyclohexylcarbamoylmethyl-carbamic acid tert-butyl ester

Yield: 81%
Reference: J. Med. Chem., 2009, 52, 5005-5008.

(Benzylcarbamoylmethyl)carbamic acid tert-butyl ester

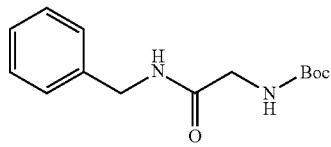 [SMILES: CC(C)(C)OC(=O)NCC(=O)NCc1ccccc1]

(Benzylcarbamoyl-methyl)-carbamic acid tert-butyl ester

Yield: 86%
Reference: Org. Lett., 2010, 12, 2718-2721.

Reference Example 3

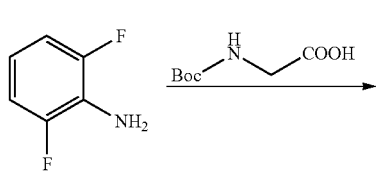

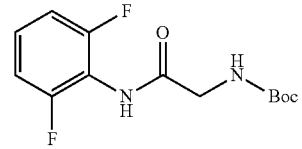

1,1-Carbonylimidazole (1.38 g, 8.51 mmol) was added to a methylene chloride (10 mL) solution of N-(tert-butoxycarbonyl)glycine (1.36 g, 7.74 mmol) in an argon atmosphere, and the mixture was stirred at room temperature for 1 hour. After the addition of 2,6-difluoroaniline (0.78 mL, 7.74 mmol), the mixture was stirred at room temperature overnight.

After evaporating the solvent, the residue was purified by silica gel column chromatography (15 g, hexane:acetone=6:1 to 3:1) to obtain [(2,6-difluorophenylcarbamoyl)methyl]carbamic acid tert-butyl ester (1.73 g) as a colorless crystalline substance.

Yield: 78%

$^1$H-NMR (400 MHz, CDCl$_3$): δ 1.47 (9H, s), 4.00 (2H, d, J=4.6 Hz), 5.22 (1H, br), 6.96, (2H, t, J=8.1 Hz), 7.18-7.27 (1H, m), 7.74 (1H, br)

IR (KBr): 1684, 3281 cm$^{-1}$

MS (EI): m/z 286 (M$^+$)

Melting point: 119 to 120° C.

The following compounds were obtained via a similar reaction.

[(2-Methylbenzylcarbamoyl)methyl]carbamic acid tert-butyl ester

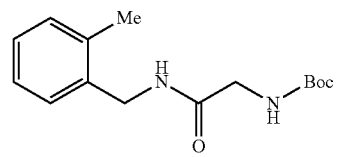 [SMILES: Cc1ccccc1CNC(=O)CNC(=O)OC(C)(C)C]

[(2-Methyl-benzylcarbamoyl)-methyl]carbamic acid tert-butyl ester

Yield: 98%

$^1$H-NMR (400 MHz, CDCl$_3$): δ 1.43 (9H, s), 2.31 (3H, s), 3.82 (2H, d, J=6.1 Hz), 4.46 (2H, d, J=5.6 Hz), 5.10 (1H, br), 6.22 (1H, br), 7.18-7.20 (4H, m)

[(4-Bromobenzylcarbamoyl)methyl]carbamic acid tert-butyl ester

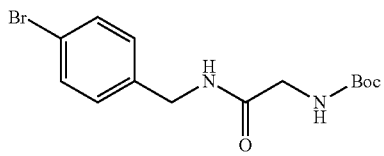 [SMILES: CC(C)(C)OC(=O)NCC(=O)NCc1ccc(Br)cc1]

[(4-Bromo-benzylcarbamoyl)-methyl]-carbamic acid tert-butyl ester

Yield: 85%

$^1$H-NMR (400 MHz, CDCl$_3$): δ 1.43 (9H, s), 3.82 (2H, d, J=6.1 Hz), 4.41 (2H, d, J=5.9 Hz), 5.12 (1H, br), 6.50 (1H, br), 7.15 (2H, d, J=8.4 Hz), 7.45 (2H, d, J=8.4 Hz)

[(4-Bromo-2-fluorobenzylcarbamoyl)methyl]carbamic acid tert-butyl ester

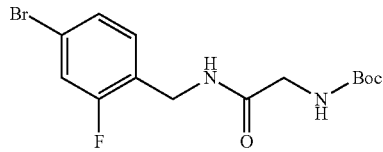 [SMILES: CC(C)(C)OC(=O)NCC(=O)NCc1ccc(Br)cc1F]

[(4-Bromo-2-fluoro-benzylcarbamoyl)-methyl]carbamic acid tert-butyl ester

Yield: 93%

$^1$H-NMR (400 MHz, CDCl$_3$): δ 1.44 (9H, s), 3.80 (2H, d, J=6.1 Hz), 4.45 (2H, d, J=6.1 Hz), 5.07 (1H, br), 6.51 (1H, br), 7.20-7.29 (3H, m)

[(3-Bromophenylcarbamoyl)methyl]carbamic acid tert-butyl ester

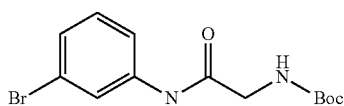

[(3-Bromo-phenylcarbamoyl)-methyl]-carbamic acid tert-butyl ester

Yield: 89%

$^1$H-NMR (400 MHz, CDCl$_3$): δ 1.47 (9H, s), 3.90 (2H, d, J=6.1 Hz), 5.20 (1H, br), 7.16 (1H, t, J=8.1 Hz), 7.22-7.25 (1H, m), 7.39 (1H, d, J=8.1 Hz), 7.75 (1H, s), 8.25 (1H, br)

[(3-Nitrophenylcarbamoyl)methyl]carbamic acid tert-butyl ester

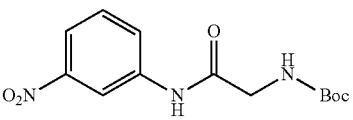 [SMILES: CC(C)(C)OC(=O)NCC(=O)Nc1cccc([N+](=O)[O-])c1]

[(3-Nitro-phenylcarbamoyl)-methyl]-carbamic acid tert-butyl ester

Yield: 92%

$^1$H-NMR (400 MHz, CDCl$_3$): δ 1.48 (9H, s), 3.94 (2H, d, J=5.9 Hz), 5.25 (1H, br), 7.47 (1H, t, J=7.9 Hz), 7.88 (1H, d, J=7.9 Hz), 7.94 (1H, d, J=7.9 Hz), 8.37 (1H, s), 8.67 (1H, br)

[(3-Chlorophenylcarbamoyl)methyl]carbamic acid tert-butyl ester

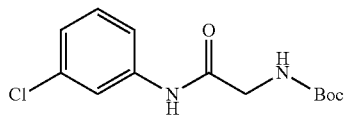 [SMILES: CC(C)(C)OC(=O)NCC(=O)Nc1cccc(Cl)c1]

[(3-Chloro-phenylcarbamoyl)-methyl]carbamic acid tert-butyl ester

Yield: 71%
Reference: WO2010/067067

[(4-Benzyloxyphenylcarbamoyl)methyl]carbamic acid tert-butyl ester

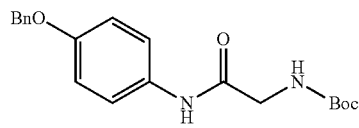 [SMILES: CC(C)(C)OC(=O)NCC(=O)Nc1ccc(OCc2ccccc2)cc1]

[(4-Benzyloxy-phenylcarbamoyl)-methyl]-carbamic acid tert-butyl ester

Yield: 68%
Reference: WO2007/141473

Reference Example 4

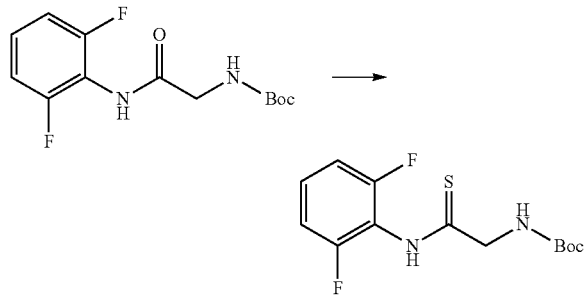

A Lawesson's reagent (50 mg, 0.12 mmol) was added to a THF (2 mL) solution of [(2,6-difluorophenylcarbamoyl)methyl]carbamic acid tert-butyl ester (52 mg, 0.18 mmol) in an argon atmosphere, and the mixture was refluxed with heating overnight. After evaporating the solvent, the residue was purified by silica gel column chromatography (13 g, hexane:acetone=10:1 to 8:1) to obtain [(2,6-difluorophenylthiocarbamoyl)methyl]carbamic acid tert-butyl ester (23 mg) as a colorless crystalline substance.

Yield: 42%

$^1$H-NMR (400 MHz, CDCl$_3$): δ 1.55 (9H, s), 4.34 (2H, d, J=6.1 Hz), 5.40 (1H, br), 6.98 (2H, t, J=8.2 Hz), 7.30 (1H, t, J=8.2 Hz), 9.59 (1H, br)

Reference Example 5

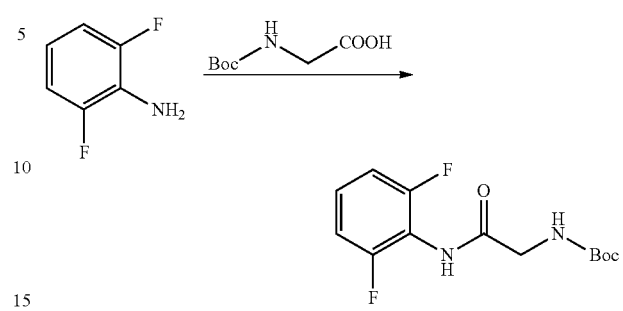

1,1-Carbonylimidazole (1.38 g, 8.51 mmol) was added to a methylene chloride (10 mL) solution of N-(tert-butoxycarbonyl)glycine (1.36 g, 7.74 mmol) in an argon atmosphere, and the mixture was stirred at room temperature for 1 hour. After the addition of 2,6-difluoroaniline (0.78 mL, 7.74 mmol), the mixture was stirred at room temperature overnight.

After evaporating the solvent, the residue was purified by silica gel column chromatography (15 g, hexane:acetone=6:1 to 3:1) to obtain [(2,6-difluorophenylcarbamoyl)methyl]carbamic acid tert-butyl ester (1.73 g) as a colorless crystalline substance.

Yield: 78%
Melting point: 119 to 120° C.

$^1$H-NMR (400 MHz, CDCl$_3$): δ 1.47 (9H, s), 4.00 (2H, d, J=4.6 Hz), 5.22 (1H, br), 6.96, (2H, t, J=8.1 Hz), 7.18-7.27 (1H, m), 7.74 (1H, br)

The following compounds were obtained via a similar reaction.

[(1-Phenylethylcarbamoyl)methyl]carbamic acid tert-butyl ester

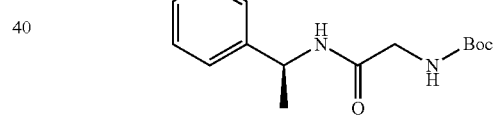

[(1-Phenyl-ethylcarbamoyl)-methyl]-carbamic acid tert-butyl ester

Yield: 96%
Reference: J. Med. Chem., 2011, 54, 2738-2744.

[(4-Methylbenzylcarbamoyl)methyl]carbamic acid tert-butyl ester

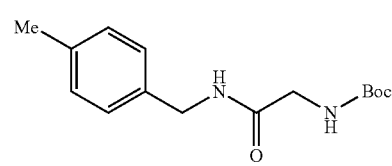 [SMILES: Cc1ccc(CNC(=O)CNC(=O)OC(C)(C)C)cc1]

[(4-Methyl-benzylcarbamoyl)-methyl]-carbamic acid tert-butyl ester

Yield: 100%
Reference: ACS Chem. Neurosci., 2010, 1, 155-164.

[(4-Chlorophenylcarbamoyl)methyl]carbamic acid tert-butyl ester

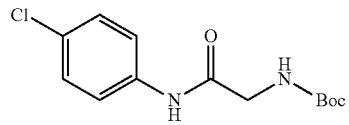 [SMILES: CC(C)(C)OC(=O)NCC(=O)Nc1ccc(Cl)cc1]

[(4-Chloro-phenylcarbamoyl)-methyl]-carbamic acid tert-butyl ester

Yield: 89%
Reference: US2008-0269280

[(2-Bromophenylcarbamoyl)methyl]carbamic acid tert-butyl ester

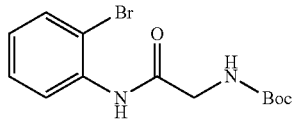 [SMILES: CC(C)(C)OC(=O)NCC(=O)Nc1ccccc1Br]

[(2-Bromo-phenylcarbamoyl)-methyl]-carbamic acid tert-butyl ester

Yield: 68%
Melting point: 118 to 119° C.
$^1$H-NMR (400 MHz, CDCl$_3$): δ 1.49 (9H, s), 3.98 (2H, d, J=5.6 Hz), 5.18 (1H, br), 6.99 (1H, td, J=8.1, 1.3 Hz), 7.32 (1H, td, J=8.1, 1.3 Hz), 7.54 (1H, dd, J=8.1, 1.3 Hz), 8.37 (1H, dd, J=8.1, 1.3 Hz), 8.47 (1H, br)
$^{13}$C-NMR (100 MHz, CDCl$_3$): δ 28.26, 45.49, 80.67, 113.38, 121.62, 125.33, 128.31, 132.23, 135.16, 156.04, 167.92

Reference Example 6

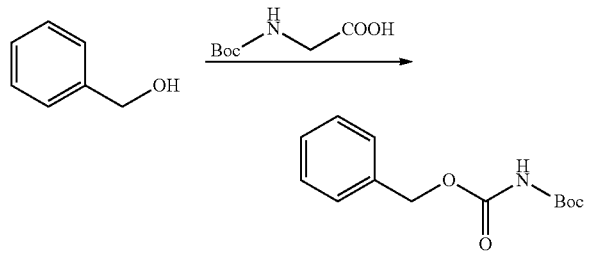

1,1-Carbonyldiimidazole (357 mg, 2.2 mmol) was added to a methylene chloride (5 mL) solution of N-(tert-butoxycarbonyl)glycine (350 mg, 2.0 mmol) in an argon atmosphere, and the mixture was stirred at room temperature for 1 hour. After the addition of benzyl alcohol (0.21 mL, 2.0 mmol), the mixture was stirred at room temperature overnight.
After evaporating the solvent, the residue was purified by silica gel column chromatography (20 g, hexane:acetone=10:1) to obtain tert-butoxycarbonylaminoacetatic acid benzyl ester as a colorless oily substance (360 mg, 68%).

Reference Example 7

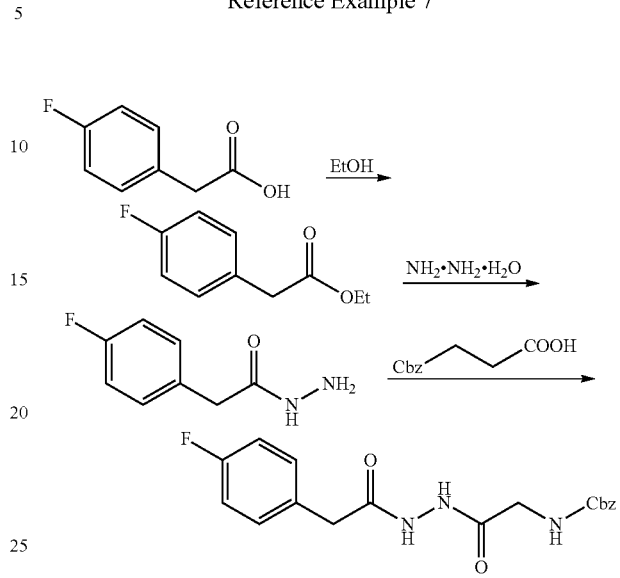

Several drops of concentrated hydrochloric acid were added to an ethanol (15 mL) solution of phenylacetic acid (770 mg, 5.00 mmol), and the mixture was refluxed with heating overnight.
A saturated sodium bicarbonate solution was added to the reaction mixture at 0° C. until the aqueous layer became neutral.
After evaporating ethanol, the organic layer was extracted with methylene chloride, dried over sodium sulfate, and filtered, and the solvent was evaporated to obtain an ethyl ester compound (colorless crystals) (910 mg, 100%).
Hydrazine monohydrate (0.13 mL, 2.74 mmol) was added to an ethanol (2.0 mL) solution of the ethyl ester compound (500 mg, 2.74 mmol), and the mixture was refluxed with heating overnight.
The solvent was evaporated to obtain a hydrazide compound (colorless crystals).
1,1-Carbodiimidazole (488 mg, 3.01 mmol) was added to a methylene chloride (7 mL) solution of N-carbobenzoxyglycine (573 mg, 2.74 mmol) in an argon atmosphere, and the mixture was stirred at room temperature for 1 hour. After the addition of a methylene chloride (3 mL) solution of the hydrazide compound using a cannula, the mixture was stirred at room temperature overnight.
After evaporating the solvent, the residue was purified by silica gel column chromatography (20 g, methylene chloride:methanol=80:1 to 30:1) to obtain [N'-[2-(4-fluorophenyl)acetyl]hydrazinocarbamoylmethyl]carbamic acid butyl ester (colorless crystals) (840 mg).

Yield: 85%
Melting point: 185 to 186° C.
$^1$H-NMR (400 MHz, CDCl$_3$): δ 3.45 (2H, s), 3.65 (2H, d, J=5.9 Hz), 5.01 (2H, s), 7.12 (2H, t, J=8.7 Hz), 7.31 (2H, dd, J=8.7, 5.7 Hz), 7.33-7.34 (5H, m), 7.51 (1H, br), 9.92 (1H, br), 10.08 (1H, br)

Reference Example 8

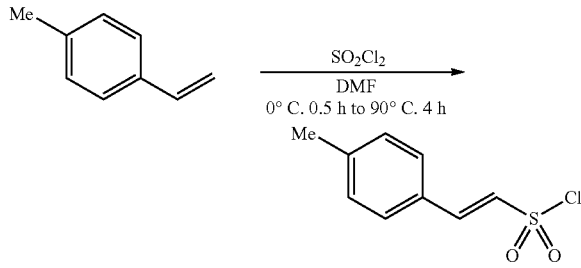

Sulfuryl chloride (1.38 mL, 17.0 mmol) was added to dimethylformamide (1.55 mL, 20.0 mmol) at 0° C. in an argon atmosphere, and the mixture was stirred for 30 minutes.

After the addition of 4-methylstyrene (1.31 mL, 10.0 mmol), the mixture was stirred at 90° C. for 4 hours.

After returning the mixture to room temperature, ice water (25 mL) was added to the mixture.

The reaction mixture was filtered under suction, and washed with water to obtain 2-p-tolylethanesulfonyl chloride (1.134 g, 52%).

Reference Example 9

Methyl iodide (0.76 mL, 12.27 mmol) and potassium carbonate (2.26 g, 16.36 mmol) were sequentially added to an acetone (5 mL) solution of 4-hydroxybenzaldehyde (500 mg, 4.09 mmol) in an argon atmosphere, and the mixture was refluxed with heating overnight.

The reaction mixture was diluted with methylene chloride (10 mL), and filtered through celite, and the solvent was evaporated.

The residue was purified by silica gel column chromatography (20 g, hexane:acetone=50:1 to 30:1) to obtain 4-methoxybenzaldehyde (439 mg, yield: 79%).
Reference: Tetrahedron, 2011, 67, 8120-8130

The following compound was obtained via a similar reaction.

2,4-Dimethoxybenzaldehyde

Yield: 84%
Reference: Bioorg. Med. Chem., 2004, 13, 433-441.

Reference Example 10 n-Butyllithium (2.45 mL, 4.00 mmol) was added to a tetrahydrofuran (10 mL) solution of 1,3,5-trichlorobenzene (724 mg, 4.00 mmol) at −78° C. in an argon atmosphere, and the mixture was stirred for 45 minutes.

After the addition of dimethylformamide (0.31 mL, 4.00 mmol) at −78° C., the mixture was stirred for 45 minutes.

After increasing the temperature of the mixture to −20° C., a saturated ammonium chloride solution (5 mL) was added to the mixture, followed by stirring for 5 minutes.

The organic layer was extracted with ethyl acetate, dried over sodium sulfate, and filtered, and the solvent was evaporated.

The residue was purified by silica gel column chromatography (15 g, hexane:acetone=50:1 to 40:1) to obtain a 2,4,6-trichlorobenzaldehyde compound (colorless crystals) (633 mg, 76%).
Reference: Synthesis, 2008, 279-285.

Reference Example 11

Malonic acid (156 mg, 1.50 mmol), pyridine (0.12 mL, 1.54 mmol), and aniline (0.01 mL, 0.12 mmol) were sequentially added to a toluene (5 mL) solution of 4-chlorobenzaldehyde (141 mg, 1.00 mmol), and the mixture was refluxed with heating overnight.

A 10% hydrochloric acid aqueous solution was added to the mixture until the aqueous layer became acidic. The organic layer was extracted with ethyl acetate, dried over sodium sulfate, and filtered, and the solvent was evaporated.

The residue was purified by silica gel column chromatography (20 g, methylene chloride:methanol=100:1 to 40:1) to obtain 3-(4-chlorophenyl)acrylic acid (colorless crystals) (162 mg, 89%).
Reference: J. Org. Chem., 2008, 73, 5766-5775.

The following compounds were obtained via a similar reaction.

3-(4-Nitrophenyl)acrylic acid

Yield: 100%
Reference: Org. Biomol. Chem., 2009, 7, 4062-4066.

3-(4-Fluorophenyl)acrylic acid

Yield: 86%
Reference: Chem. Eur. J., 2000, 6, 3386-3390.

3-(2,4-Dimethoxyphenyl)acrylic acid

Yield: 95%
Reference: Synth. Commun., 1980, 10, 37-42.

3-(4-Isopropylphenyl)acrylic acid

Yield: 90%
Reference: Synth. Commun., 2002, 32, 195-201.

3-(Biphenyl-4-yl)acrylic acid

Yield: 60%
Reference: J. Med. Chem., 1993, 36, 2381-2389.

3-(2,6-Dimethoxyphenyl)acrylic acid

Yield: 100%
Reference: J. Org. Chem., 1995, 60, 1981-1984.

3-(4-Trifluoromethylphenyl)acrylic acid

Yield: 100%
Reference: J. Org. Chem., 1999, 64, 3975-3978.

Reference Example 12

(1) Triethyl phosphonoacetate (0.66 mL, 3.32 mmol) was added to a tetrahydrofuran (5 mL) solution of sodium hydride (133 mg, 3.32 mmol) in an argon atmosphere, and the mixture was stirred for 30 minutes. After the addition of a tetrahydrofuran (5 mL) solution of 2,4,6-trichlorobenzaldehyde (580 mg, 2.77 mmol) using a cannula, the mixture was stirred at room temperature overnight.

After evaporating the solvent, water (10 mL) was added to the mixture. The organic layer was extracted with methylene chloride, dried over sodium sulfate, and filtered, and the solvent was evaporated.

The residue was purified by silica gel column chromatography (15 g, hexane:acetone=90:1 to 80:1) to obtain 3-(2,4,6-trichlorophenyl)acrylic acid ethyl ester (colorless oil) (751 mg, 97%).

(2) Lithium hydroxide monohydrate (226 mg, 5.38 mmol) was added to a methanol-water (3:1) solution (20 mL) of 3-(2,4,6-trichlorophenyl)acrylic acid ethyl ester (751 mg, 2.69 mmol) in an argon atmosphere, and the mixture was refluxed with heating for 2 hours.

After evaporating the solvent, a 10% hydrochloric acid aqueous solution was added to the mixture until the aqueous layer became acidic. The organic layer was extracted with ethyl acetate, dried over sodium sulfate, and filtered, and the solvent was evaporated to obtain 3-(2,4,6-trichlorophenyl)acrylic acid (colorless crystals) (654 mg, 97%).

$^1$H-NMR (400 MHz, CDCl$_3$): δ 6.64 (1H, d, J=16.2 Hz), 7.41 (2H, s), 7.82 (1H, d, J=16.2 Hz)

The following compounds were obtained via a similar reaction.

3-(3,5-Dibromophenyl)acrylic acid

Yield: 100%
Reference: WO2004/046122

3-(2,4,6-trifluorophenyl)acrylic acid

Yield: 99%
Reference: WO2001/092239

Reference Example 13

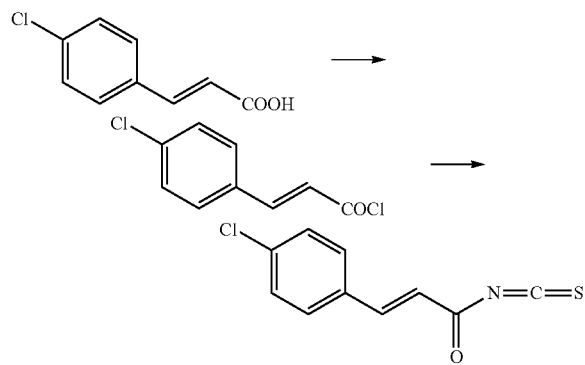

Thionyl chloride (0.05 mL, 0.66 mmol) was added to a methylene chloride (3 mL) solution of 3-(4-chlorophenyl)acrylic acid (100 mg, 0.55 mmol) in an argon atmosphere, and the mixture was stirred at room temperature overnight.

After evaporating the solvent, methylene chloride (3 mL) was added to the mixture. After the sequential addition of ammonium thiocyanate (63 mg, 0.82 mmol) and PEG-400 (one drop), the mixture was stirred at room temperature for 2 hours.

After evaporating the solvent, the residue was purified by silica gel column chromatography (15 g, hexane:acetone=50:1 to 40:1) to obtain 3-(4-chlorophenyl)acryloyl isothiocyanate (colorless crystals) (105 mg, 85%).

$^1$H-NMR (400 MHz, CDCl$_3$): δ 6.48 (1H, d, J=16.1 Hz), 7.41 (2H, d, J=8.7 Hz), 7.50 (2H, d, J=8.7 Hz), 7.72 (1H, d, J=15.6 Hz); Yield: 85%.

The following compounds were obtained via a similar reaction.

3-(2,4,6-Trichlorophenyl)acryloyl isothiocyanate

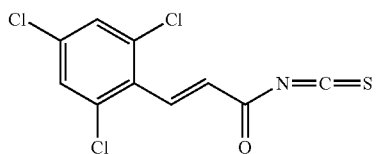 [SMILES: O=C(/C=C/c1c(Cl)cc(Cl)cc1Cl)N=C=S]

3-(2,4,6-Trichloro-phenyl)-acryloyl isothiocyanate $^1$H-NMR (400 MHz, CDCl$_3$) δ: 6.74 (1H, d, J=16.1 Hz), 7.43 (2H, s), 7.85 (1H, d, J=16.1 Hz)

Yield: 80%

3-(4-Fluorophenyl)acryloyl isothiocyanate

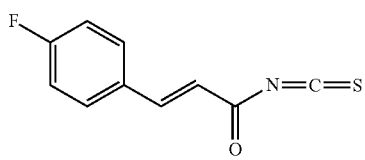 [SMILES: O=C(/C=C/c1ccc(F)cc1)N=C=S]

3-(4-Fluoro-phenyl)-acryloyl isothiocyanate $^1$H-NMR (400 MHz, CDCl$_3$) δ: 6.43 (1H, d, J=15.8 Hz), 7.13 (2H, t, J=8.6 Hz), 7.57 (2H, dd, J=8.6, 5.3 Hz), 7.73 (1H, d, J=15.8 Hz)

Yield: 88%

3-(2,4-Dimethoxyphenyl)acryloyl isothiocyanate

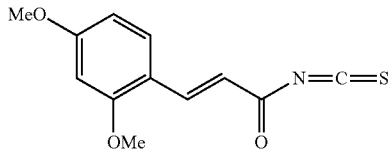 [SMILES: COc1ccc(/C=C/C(=O)N=C=S)c(OC)c1]

3-(2,4-Dimethoxy-phenyl)-acryloyl isothiocyanate $^1$H-NMR (400 MHz, CDCl$_3$) δ: 3.84 (3H, s), 3.88 (3H, s), 6.42-6.53 (3H, m), 7.46 (1H, d, J=16.1 Hz), 8.00 (1H, d, J=16.1 Hz)

Yield: 73%

3-(2,4-Dibromodiphenyl)acryloyl isothiocyanate

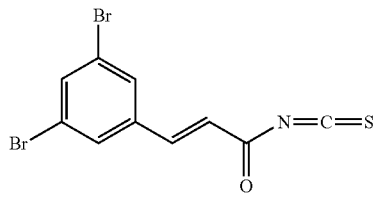 [SMILES: O=C(/C=C/c1cc(Br)cc(Br)c1)N=C=S]

3-(3,5-Dibromo-phenyl)-acryloyl isothiocyanate

¹H-NMR (400 MHz, CDCl₃) δ: 6.45 (1H, d, J=15.8 Hz), 7.58-7.62 (3H, m), 7.74 (1H, s)
Yield: 63%

3-(4-Isopropylphenyl)acryloyl isothiocyanate

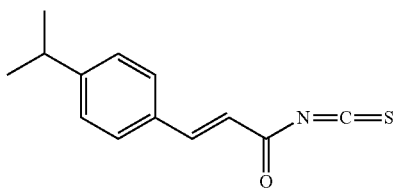 [SMILES: CC(C)c1ccc(/C=C/C(=O)N=C=S)cc1]

3-(4-Isopropyl-phenyl)-acryloyl isothiocyanate

¹H-NMR (400 MHz, CDCl₃) δ: 1.25 (6H, d, J=7.1 Hz), 2.93 (1H, sept, J=7.1 Hz), 6.45 (1H, d, J=15.7 Hz), 7.27 (2H, d, J=8.2 Hz), 7.48 (2H, d, J=8.2 Hz), 7.73 (1H, d, J=15.7 Hz)
Yield: 79%

3-(Biphenyl-4-yl)acryloyl isothiocyanate

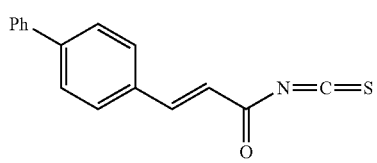 [SMILES: O=C(/C=C/c1ccc(-c2ccccc2)cc1)N=C=S]

3-Biphenyl-4-yl-acryloyl isothiocyanate

¹H-NMR (400 MHz, CDCl₃): δ 6.47 (1H, d, J=15.6 Hz), 7.33 (1H, t, J=7.4 Hz), 7.41 (2H, t, J=7.4 Hz), 7.55-7.61 (6H, m), 7.74 (1H, d, J=15.6 Hz)
Yield: 83%

3-(2,6-Dimethoxyphenyl)acryloyl isothiocyanate

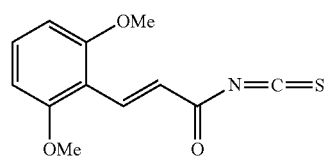

3-(2,6-Dimethoxy-phenyl)-acryloyl isothiocyanate

¹H-NMR (400 MHz, CDCl₃) δ: 3.89 (6H, s), 6.55 (2H, d, J=8.5 Hz), 6.99 (1H, d, J=15.9 Hz), 7.32 (1H, t, J=8.5 Hz), 8.23 (1H, d, J=15.9 Hz)
Yield: 27%

3-(2,4,6-Trifluorophenyl)acryloyl isothiocyanate

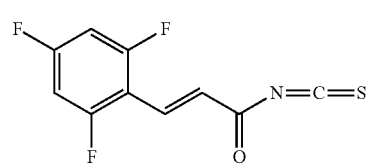 [SMILES: O=C(/C=C/c1c(F)cc(F)cc1F)N=C=S]

3-(2,4,6-Trifluoro-phenyl)-acryloyl isothiocyanate

¹H-NMR (400 MHz, CDCl₃): δ 6.74-6.79 (3H, m), 7.78 (1H, d, J=16.1 Hz)
Yield: 67%

3-(4-Trifluoromethylphenyl)acryloyl isothiocyanate

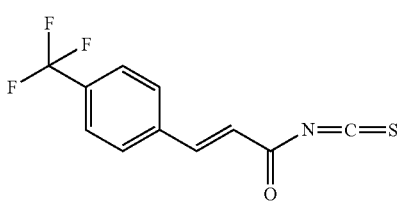 [SMILES: O=C(/C=C/c1ccc(C(F)(F)F)cc1)N=C=S]

3-(4-Trifluoromethyl-phenyl)-acryloyl isothiocyanate

¹H-NMR (400 MHz, CDCl₃) δ: 6.57 (1H, d, J=15.9 Hz), 7.66-7.71 (4H, m), 7.78 (1H, d, J=15.9 Hz)
Yield: 85%

3-(4-Nitrophenyl)acryloyl isothiocyanate

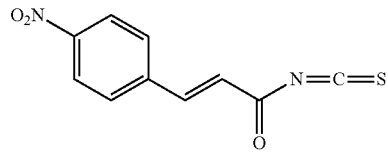 [SMILES: O=C(/C=C/c1ccc([N+](=O)[O-])cc1)N=C=S]

3-(4-Nitro-phenyl)-acryloyl isothiocyanate

Yield: 85%
Reference: Chem. Pep. Chem. Zvesti, 1974, 28, 693-696.

3-(4-Methylphenyl)acryloyl isothiocyanate

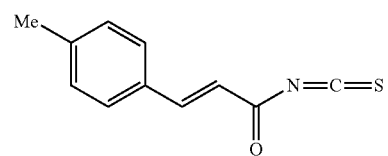 [SMILES: Cc1ccc(/C=C/C(=O)N=C=S)cc1]

3-p-Tolyl-acryloyl isothiocyanate

Yield: 60%
Reference: Chem. Pep. Chem. Zvesti, 1969, 23, 173-180.

Reference Example 14

Phenylacetyl isothiocyanate

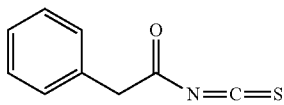

Phenyl-acetyl isothiocyanate

Ammonium thiocyanate (114 mg, 1.50 mmol) and PEG-400 (three drops) were sequentially added to a methylene chloride (5 mL) solution of acetyl chloride (155 mg, 1 mmol) in an argon atmosphere, and the mixture was stirred at room temperature for 2 hours.

After evaporating the solvent, the residue was purified by silica gel column chromatography (15 g, hexane:acetone=50:1 to 40:1) to obtain phenylacetyl isothiocyanate (colorless crystals) (132 mg, 75%).

The following compounds were obtained via a similar reaction.

(4-Fluorophenyl)acetyl isothiocyanate

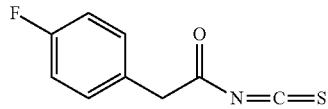 [SMILES: O=C(Cc1ccc(F)cc1)N=C=S]

(4-Fluoro-phenyl)-acetyl isothiocyanate

Yield: 48%
Reference: Bioorg. Med. Chem. Lett., 2008, 18, 1945-1951.

3-Phenylpropionyl isothiocyanate

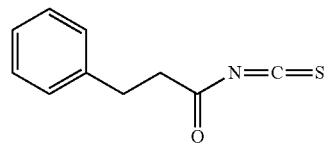 [SMILES: O=C(CCc1ccccc1)N=C=S]

3-Phenyl-propionyl isothiocyanate

Yield: 28%
Reference: J. Org. Chem., 2008, 73, 2096-2104.

Reference Example 15

(2,6-Difluorophenyl)acetyl isothiocyanate

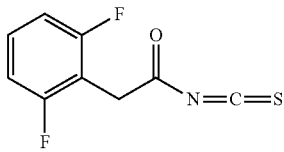 [SMILES: O=C(Cc1c(F)cccc1F)N=C=S]

(2,6-Difluoro-phenyl)-acetyl isothiocyanate

Thionyl chloride (0.15 mL, 2.00 mmol) was added to a benzene (5 mL) solution of (2,6-difluorophenyl)acetic acid (172 mg, 1.00 mmol) in an argon atmosphere, and the mixture was refluxed with heating overnight.

After evaporating the solvent, methylene chloride (5 mL) was added to the mixture. After the sequential addition of ammonium thiocyanate (114 mg, 1.50 mmol) and PEG-400 (four drops), the mixture was stirred at room temperature overnight.

After evaporating the solvent, the residue was purified by silica gel column chromatography (15 g, hexane:acetone=50:1 to 40:1) to obtain (2,6-difluorophenyl)acetyl isothiocyanate (colorless crystals) (105 mg, 49%).
Reference: WO2009/125597

Reference Example 16

(Cyclohexyl)acetyl isothiocyanate

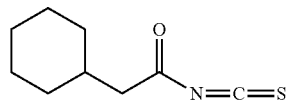 [SMILES: O=C(CC1CCCCC1)N=C=S]

Cyclohexyl-acetyl isothiocyanate

Thionyl chloride (0.15 mL, 2.00 mmol) was added to a benzene (5 mL) solution of cyclohexylacetic acid (142 mg, 1.00 mmol) in an argon atmosphere, and the mixture was refluxed with heating overnight.

After evaporating the solvent, methylene chloride (5 mL) was added to the mixture. After the sequential addition of ammonium thiocyanate (114 mg, 1.50 mmol) and PEG-400 (four drops), the mixture was stirred at room temperature overnight.

After evaporating the solvent, the residue was purified by silica gel column chromatography (15 g, hexane:acetone=80:1 to 70:1) to obtain (cyclohexyl)acetyl isothiocyanate (colorless crystals) (120 mg, 66%).
Reference: WO2007/054831

Reference Example 17

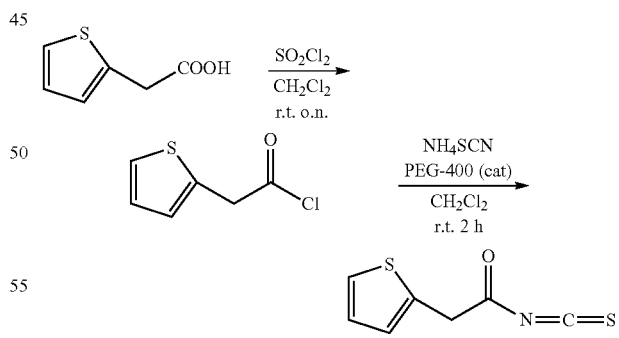

Thionyl chloride (0.29 mL, 4.00 mmol) was added to a methylene chloride (5 mL) solution of 2-thiopheneacetic acid (284 mg, 2.00 mmol) in an argon atmosphere, and the mixture was refluxed with heating overnight.

After evaporating the solvent, methylene chloride (5 mL) was added to the mixture. After the sequential addition of thioammonium cyanide (228 mg, 3.00 mmol) and polyethylene glycol (PEG-400, six drops), the mixture was stirred at room temperature overnight.

After evaporating the solvent, the residue was purified by silica gel column chromatography (15 g, hexane:acetone=100:1) to obtain thiophen-2-ylacetyl chloride (colorless crystals) (133 mg, 36%).

Reference Example 18

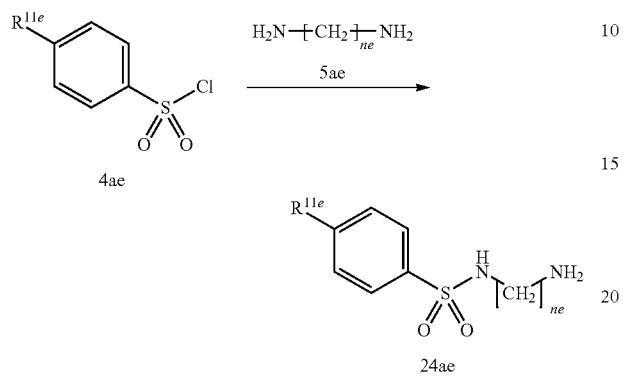

2 mL of a methylene chloride solution of the sulfonyl chloride compound 4a (1.0 mmol) was added to 5 mL of a methylene chloride solution of the diamine compound 5a (5.0 mmol) at 0° C. in an argon atmosphere using a cannula, and the mixture was stirred at room temperature for 3 hours.

10 mL of water was added to the mixture.

The organic layer was extracted with methylene chloride, dried over sodium sulfate, dried, and filtered.

The solvent was evaporated to obtain the amine compound 2a.

The following compound was obtained via a similar reaction.

N-(2-Aminoethyl)-4-methylbenzenesulfonamide

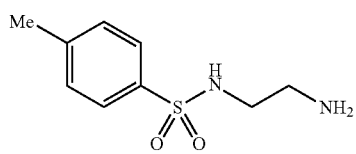 [SMILES: Cc1ccc(S(=O)(=O)NCCN)cc1]

N-(2-Amino-ethyl)-4-methyl-benzenesulfonamide

Yield: 69%
Reference: Tetrahedron, 2011, 67, 6206-6213.

N-(2-Aminoethyl)-4-methoxybenzenesulfonamide

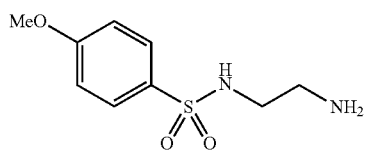 [SMILES: COc1ccc(S(=O)(=O)NCCN)cc1]

N-(2-Amino-ethyl)-4-methoxy-benzenesulfonamide

Yield: 39%
Reference: Zh. Obshch. Khim., 1962, 32, 887-892.

N-(2-Aminoethyl)-4-bromobenzenesulfonamide

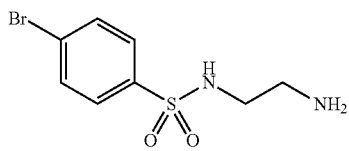 [SMILES: NCCNS(=O)(=O)c1ccc(Br)cc1]

N-(2-Amino-ethyl)-4-bromo-benzenesulfonamide

Yield: 35%
Reference: Zh. Obshch. Khim., 1962, 32, 887-892.

N-(2-Aminoethyl)-4-chlorobenzenesulfonamide

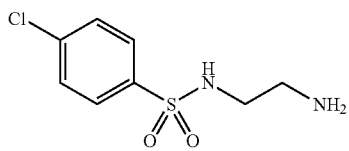 [SMILES: NCCNS(=O)(=O)c1ccc(Cl)cc1]

N-(2-Amino-ethyl)-4-chloro-benzenesulfonamide

Yield: 51%
Reference: J. Med. Chem., 1982, 25, 1286-1292.

N-(2-Aminoethyl)-4-fluorobenzenesulfonamide

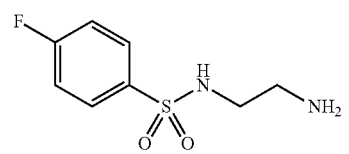 [SMILES: NCCNS(=O)(=O)c1ccc(F)cc1]

N-(2-Amino-ethyl)-4-fluoro-benzenesulfonamide

Yield: 39%
Reference: Chin. J. Chem., 2011, 29, 2081-2085.

N-(3-Aminopropyl)-4-methylbenzenesulfonamide

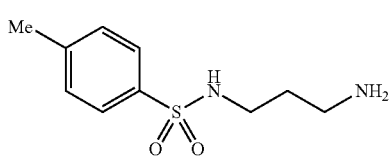 [SMILES: Cc1ccc(S(=O)(=O)NCCCN)cc1]

N-(3-Amino-propyl)-4-methyl-benzenesulfonamide

Yield: 46%
Reference: J. Med. Chem., 2012, 55, 4457-4478.

N-(3-Aminopropyl)-4-methoxybenzenesulfonamide

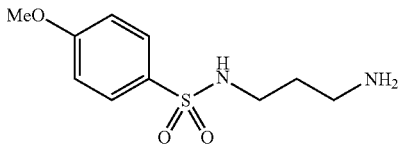 [SMILES: COc1ccc(S(=O)(=O)NCCCN)cc1]

N-(3-Amino-propyl)-4-methoxy-benzenesulfonamide

Yield: 58%
Reference: WO98/08822
Commercially Available Products

N-(3-Aminopropyl)-4-bromobenzenesulfonamide

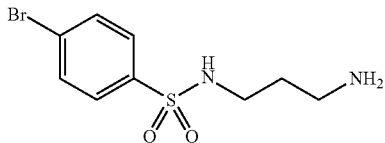 [SMILES: NCCCNS(=O)(=O)c1ccc(Br)cc1]

N-(3-Amino-propyl)-4-bromo-benzenesulfonamide

N-(3-Aminopropyl)-4-fluorobenzenesulfonamide

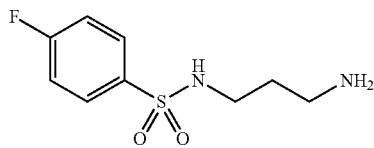 [SMILES: NCCCNS(=O)(=O)c1ccc(F)cc1]

N-(3-Amino-propyl)-4-fluoro-benzenesulfonamide

Reference Example 19

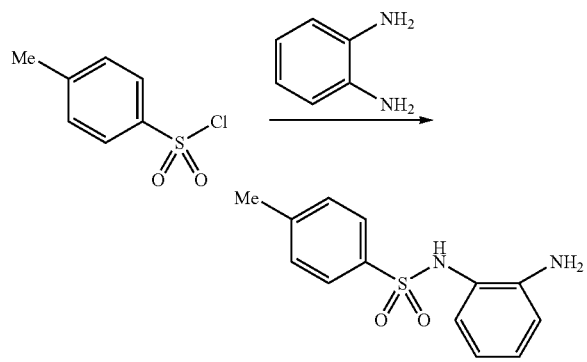

Pyridine (0.149 mL, 1.85 mmol) was added to 3 mL of a tetrahydrofuran solution of o-phenylenediamine (500 mg, 4.62 mmol) in an argon atmosphere. After the addition of 2 mL of a tetrahydrofuran solution of toluenesulfonyl chloride (294 mg, 1.54 mmol) at 0° C. using a cannula, the mixture was stirred at room temperature for 4 hours.

5 mL of water was added to the mixture.
The organic layer was extracted with methylene chloride, washed with 5 mL of a saturated sodium chloride solution, dried over sodium sulfate, and filtered.
After evaporating the solvent, the residue was purified by silica gel column chromatography (15 g, hexane:acetone=10:1) to obtain N-(2-aminophenyl)-4-methylbenzenesulfonamide (colorless crystals) (218 mg, 54%).
Reference: Angew. Chem. Int. Ed., 2007, 46, 7247-7250.

Reference Example 20

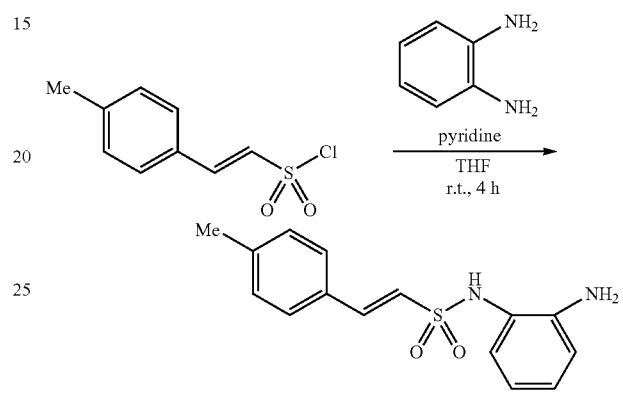

Pyridine (0.1 mL, 1.80 mmol) was added to a tetrahydrofuran (3 mL) solution of phenylenediamine (487 mg, 4.50 mmol) in an argon atmosphere. After the addition of a tetrahydrofuran (2 mL) solution of 4-chlorobenzenesulfonyl chloride (317 mg, 1.50 mmol) at 0° C. using a cannula, the mixture was stirred at room temperature for 4 hours.

After evaporating the solvent, water (5 mL) was added to the mixture. The organic layer was extracted with methylene chloride, washed with a saturated sodium chloride solution (5 mL), dried over sodium sulfate, and filtered, and the solvent was evaporated.

The residue was recrystallized from ethanol-water to obtain 2-p-tolylethanesulfonyl acid(2-aminophenyl)amide (384 mg, 91%) as a colorless crystalline substance.

$^1$H-NMR (400 MHz, CDCl$_3$): δ 2.36 (3H, s), 4.15 (2H, br), 5.95 (1H, br), 6.65 (td, J=8.1, 1.5 Hz), 6.76 (1H, dd, J=8.1, 1.5 Hz), 6.79 (1H, d, J=15.4 Hz), 6.99 (1H, dd, J=8.1, 1.5 Hz), 7.07 (1H, td, J=8.1, 1.5 Hz), 7.18 (2H, d, J=8.2 Hz), 7.32 (2H, d, J=8.2 Hz), 7.38 (1H, d, J=15.4 Hz)

The following compound was obtained via a similar reaction.

N-(2-Aminophenyl)-4-fluorobenzenesulfonamide

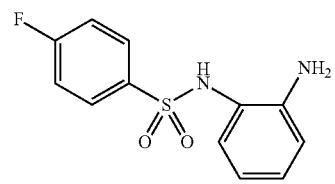 [SMILES: Nc1ccccc1NS(=O)(=O)c1ccc(F)cc1]

N-(2-Amino-phenyl)-4-fluoro-benzenesulfonamide

Yield: 61%
Reference: WO98/54131

N-(2-Aminophenyl)-4-methoxybenzenesulfonamide

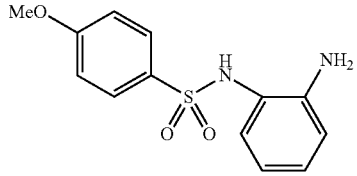 [SMILES: COc1ccc(S(=O)(=O)Nc2ccccc2N)cc1]

N-(2-Amino-phenyl)-4-methoxy-benzenesulfonamide

Yield: 52%
Reference: WO98/54131

N-(2-Aminophenyl)-4-bromobenzenesulfonamide

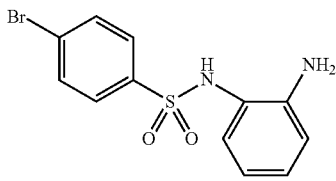 [SMILES: Nc1ccccc1NS(=O)(=O)c1ccc(Br)cc1]

N-(2-Amino-phenyl)-4-bromo-benzenesulfonamide

Yield: 50%

Example 1

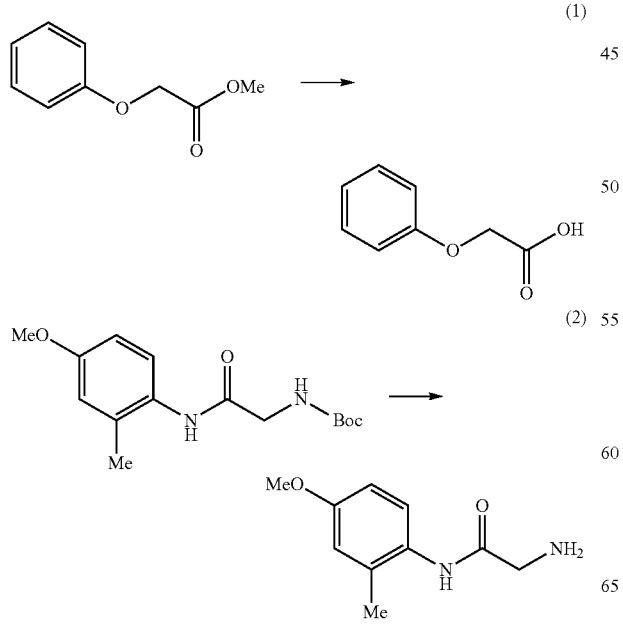

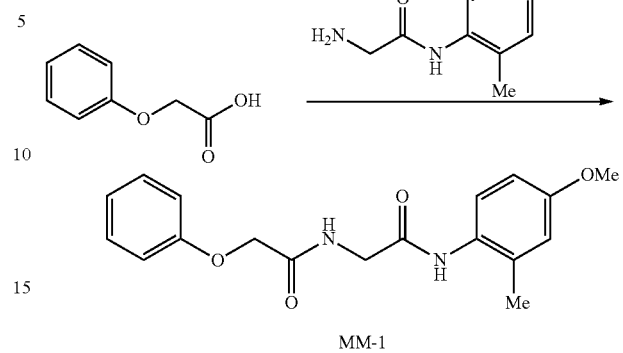

(1) Lithium hydroxide monohydrate (52 mg, 1.23 mmol) was added to a methanol-water (3:1) solution (4 mL) of phenoxyacetic acid methyl ester (102 mg, 0.61 mmol), and the mixture was refluxed with heating for 2 hours.

After evaporating the solvent, a 10% hydrochloric acid aqueous solution was added to the mixture until the aqueous layer became acidic, followed by extraction with ethyl acetate.

The organic layer was dried over sodium sulfate, and filtered, and the solvent was evaporated to obtain phenoxyacetic acid (92 mg) as a colorless crystalline substance.

(2) Trifluoroacetic acid (0.6 mL, 8.08 mmol) was added to a methylene chloride (3.5 mL) solution of [(4-methoxy-2-methylphenylcarbamoyl)methyl]carbamic acid tert-butyl ester (236 mg, 0.80 mmol) in an argon atmosphere, and the mixture was stirred at room temperature overnight.

A saturated sodium bicarbonate solution was added to the reaction mixture at 0° C. until the aqueous layer became basic, followed by extraction with methylene chloride.

The organic layer was dried over potassium carbonate, and filtered, and the solvent was evaporated to obtain 2-amino-N-(4-methoxy-2-methylphenyl)acetamide (146 mg) as a colorless crystalline substance.

(3) 1,1-Carbonyldiimidazole (92 mg, 0.57 mmol) was added to a methylene chloride (5 mL) solution of phenoxyacetic acid (78 mg, 0.52 mmol) in an argon atmosphere, and the mixture was stirred at room temperature for 1 hour. After the addition of a methylene chloride (2 mL) solution of 2-amino-N-(4-methoxy-2-methylphenyl)acetamide (100 mg, 0.52 mmol) using a cannula, the mixture was stirred at room temperature overnight.

After evaporating the solvent, the residue was purified by silica gel column chromatography (15 g, hexane:acetone=5:1 to 3:1) to obtain N-[(4-methoxy-2-methylphenylcarbamoyl)methyl]-2-phenoxyacetamide (113 mg) as a colorless crystalline substance.

MM-1

Yield: 67%
Melting point: 165 to 166° C. (recrystallization solvent: acetone)
$^1$H-NMR (400 MHz, CDCl$_3$): δ 2.19 (3H, s), 3.76 (3H, s), 4.16 (2H, d, J=5.9 Hz), 4.57 (2H, s), 6.72 (2H, m), 6.92 (2H, d, J=7.6 Hz), 7.01 (1H, t, J=7.6 Hz), 7.30 (2H, t, J=7.6 Hz), 7.38 (1H, br), 7.52 (1H, d, J=9.5 Hz), 7.62 (1H, br)
$^{13}$C-NMR (100 MHz, DMSO-d$_6$): δ 17.95, 42.06, 55.09, 66.86, 111.15, 114.74, 115.32, 121.20, 126.67, 128.81, 129.50, 134.03, 156.83, 157.68, 167.49, 168.21
IR (KBr): 1668, 3258 cm$^{-1}$
MS (EI): m/z 328 (M$^+$)

Example 2

The following compounds were obtained in the same manner as in Example 1.

2-(4-Chlorophenoxy)-N-[(4-methoxy-2-methylphenylcarbamoyl)methyl]acetamide

MM-2

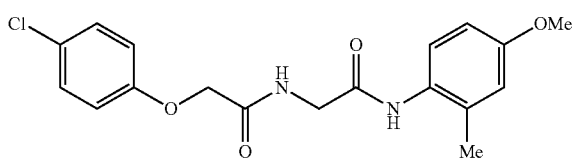 [SMILES: COc1ccc(NC(=O)CNC(=O)COc2ccc(Cl)cc2)c(C)c1]

2-(4-Chloro-phenoxy)-N-[(4-methoxy-2-methyl-phenylcarbamoyl)-methyl]-acetamide

Yield: 80%
Melting point: 170 to 171° C. (recrystallization solvent: acetone)
$^1$H-NMR (400 MHz, CDCl$_3$): δ 2.20 (3H, s), 3.76 (3H, s), 4.16 (2H, d, J=5.6 Hz), 4.53 (2H, s), 6.71-6.73 (2H, m), 6.85 (2H, d, J=9.0 Hz), 7.24-7.27 (2H, m), 7.35 (1H, br), 7.50 (1H, d, J=9.5 Hz), 7.56 (1H, br)
$^{13}$C-NMR (100 MHz, DMSO-d$_6$): δ 17.95, 42.03, 55.09, 67.10, 111.15, 115.32, 116.55, 124.91, 126.68, 128.80, 129.23, 134.05, 156.57, 156.83, 167.45, 167.91
IR (KBr): 1666, 3267 cm$^{-1}$
MS (EI): m/z 362 (M$^+$)

2-(4-Bromophenoxy)-N-[(4-methoxy-2-methylphenylcarbamoyl)methyl]acetamide

MM-3

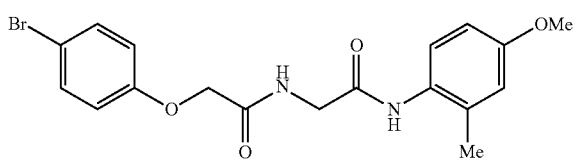 [SMILES: COc1ccc(NC(=O)CNC(=O)COc2ccc(Br)cc2)c(C)c1]

2-(4-Bromo-phenoxy)-N-[(4-methoxy-2-methyl-phenylcarbamoyl)-methyl]-acetamide

Yield: 69%
Melting point: 159 to 160° C. (recrystallization solvent: acetone)
$^1$H-NMR (400 MHz, CDCl$_3$): 2.19 (3H, s), 3.76 (3H, s), 4.16 (2H, d, J=5.6 Hz), 4.52 (2H, s), 6.71-6.73 (2H, m), 6.81 (2H, d, J=8.8 Hz), 7.36 (1H, br), 7.40 (2H, d, J=8.8 Hz), 7.50 (1H, d, J=9.5 Hz), 7.59 (1H, br)
$^{13}$C-NMR (100 MHz, DMSO-d$_6$): δ 17.95, 55.10, 67.03, 100.08, 111.16, 112.63, 115.32, 117.07, 126.69, 128.79, 132.12, 134.05, 156.83, 157.02, 167.44, 167.88
IR (KBr): 1663, 3273 cm$^{-1}$
MS (EI): m/z 406 (M$^+$)

2-(4-Chlorophenoxy)-N-[(4-iodophenylcarbamoyl)methyl]acetamide

MM-4

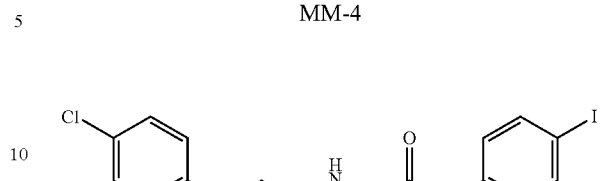

2-(4-Chloro-phenoxy)-N-[(4-iodo-phenylcarbamoyl)-methyl]-acetamide

Yield: 78%
Melting point: 205 to 206° C. (recrystallization solvent: acetone)
$^1$H-NMR (400 MHz, CDCl$_3$): δ 4.13 (2H, d, J=5.6 Hz), 4.54 (2H, s), 6.86 (2H, d, J=9.0 Hz), 7.24-7.28 (3H, m), 7.27 (2H, d, J=9.0 Hz), 7.61 (2H, d, J=8.8 Hz), 7.98 (1H, br)
$^{13}$C-NMR (100 MHz, DMSO-d$_6$): δ 42.42, 67.05, 86.74, 116.56, 121.33, 124.95, 129.23, 137.39, 138.62, 156.52, 167.52, 167.94
IR (KBr): 1663, 3294 cm$^{-1}$
MS (EI): m/z 444 (M$^+$)

2-(4-Bromophenoxy)-N-[(4-iodophenylcarbamoyl)methyl]acetamide

MM-5

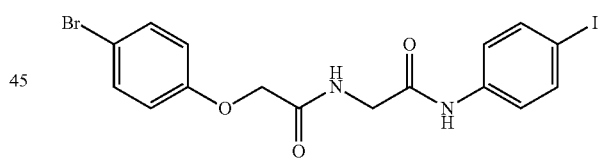

2-(4-Bromo-phenoxy)-N-[(4-iodo-phenylcarbamoyl)-methyl]acetamide

Yield: 91%
Melting point: 211 to 212° C. (recrystallization solvent: acetone)
$^1$H-NMR (400 MHz, CDCl$_3$): δ 4.13 (2H, d, J=5.6 Hz), 4.53 (2H, s), 6.81 (2H, d, J=8.8 Hz), 7.24-7.30 (3H, m), 7.41 (2H, d, J=8.8 Hz), 7.61 (2H, d, J=8.8 Hz), 7.98 (1H, br)
$^{13}$C-NMR (100 MHz, DMSO-d$_6$): δ 42.43, 66.99, 86.75, 112.69, 117.08, 121.34, 132.14, 137.40, 138.63, 156.98, 167.53, 167.93
IR (KBr): 1661, 3290 cm$^{-1}$
MS (EI): m/z 488 (M$^+$)

2-(4-Fluorophenoxy)-N-[(4-methoxy-2-methylphenylcarbamoyl)methyl]acetamide

MM-6

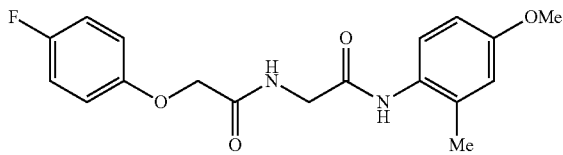 [SMILES: COc1ccc(NC(=O)CNC(=O)COc2ccc(F)cc2)c(C)c1]

2-(4-Fluoro-phenoxy)-N-[(4-methoxy-2-methyl-phenylcarbamoyl)-methyl]-acetamide

Yield: 82%

Melting point: 169 to 170° C. (recrystallization solvent: acetone)

$^1$H-NMR (400 MHz, CDCl$_3$): δ 2.22 (3H, s), 3.78 (3H, s), 4.18 (2H, d, J=5.6 Hz), 4.54 (2H, s), 6.74-6.75 (2H, m), 6.89 (2H, dd, J=8.9, 4.1 Hz), 7.01 (2H, t, J=8.9 Hz), 7.38 (1H, br), 7.54 (1H, d, J=9.8 Hz), 7.59 (1H, br)

$^{13}$C-NMR (100 MHz, DMSO-d$_6$): δ 17.93, 42.03, 55.08, 67.48, 111.14, 115.31, 115.82 (d, J=22.3 Hz), 116.12 (d, J=8.3 Hz), 126.67, 128.81, 134.03, 154.05 (d, J=2.5 Hz), 156.82, 156.84 (d, J=236.5 Hz), 167.47, 168.09

IR (KBr): 3260, 1666 cm$^{-1}$

MS (EI): m/z 346 (M$^+$)

2-(4-Fluorophenoxy)-N-[(4-iodophenylcarbamoyl)methyl]acetamide

MM-7

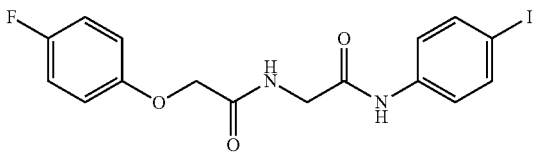 [SMILES: O=C(COc1ccc(F)cc1)NCC(=O)Nc1ccc(I)cc1]

2-(4-Fluoro-phenoxy)-N-[(4-iodo-phenylcarbamoyl)-methyl]-acetamide

Yield: 96%

Melting point: 190 to 191° C. (recrystallization solvent: acetone)

$^1$H-NMR (400 MHz, CDCl$_3$): δ 4.17 (2H, d, J=4.9 Hz), 4.55 (2H, s), 6.90 (2H, dd, J=8.8, 4.0 Hz), 7.02 (2H, t, J=8.8 Hz), 7.12 (1H, br), 7.29 (2H, d, J=8.5 Hz), 7.38 (1H, br), 7.63 (2H, d, J=8.5 Hz)

$^{13}$C-NMR (100 MHz, DMSO-d$_6$): δ 42.41, 67.44, 86.73, 115.85 (d, J=23.2 Hz), 116.14 (d, J=8.3 Hz), 121.34, 137.39, 138.64, 154.02 (d, J=2.5 Hz), 156.87 (d, J=236.6 Hz), 167.55, 168.13

IR (KBr): 3312, 1672 cm$^{-1}$

MS (EI): m/z 428 (M$^+$)

2-(4-Bromophenoxy)-N-[(4-fluorophenylcarbamoyl)methyl]acetamide

MM-8

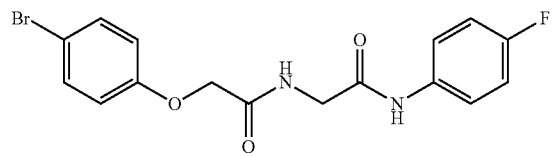 [SMILES: O=C(COc1ccc(Br)cc1)NCC(=O)Nc1ccc(F)cc1]

2-(4-Bromo-phenoxy)-N-[(4-fluoro-phenylcarbamoyl)-methyl]-acetamide

Yield: 97%

Melting point: 213 to 214° C. (recrystallization solvent: acetone)

$^1$H-NMR (400 MHz, CDCl$_3$): δ 4.13 (2H, d, J=5.9 Hz), 4.53 (2H, s), 6.82 (2H, d, J=8.9 Hz), 7.00 (2H, d, J=8.5 Hz), 7.31 (1H, br), 7.40-7.44 (2H, m), 7.41 (2H, d, J=8.9 Hz), 7.95 (1H, br)

$^{13}$C-NMR (100 MHz, DMSO-d$_6$): δ 42.28, 66.98, 112.65, 115.28 (d, J=22.3 Hz), 117.07, 120.90 (d, J=7.4 Hz), 132.11, 135.18 (d, J=2.5 Hz), 156.99, 157.96 (d, J=239.8 Hz), 167.24, 167.88

IR (KBr): 3389, 1657 cm$^{-1}$

MS (EI): m/z 380 (M$^+$)

2-(4-Fluorophenoxy)-N-[(4-fluorophenylcarbamoyl)methyl]acetamide

MM-9

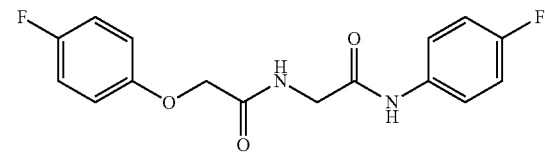 [SMILES: O=C(COc1ccc(F)cc1)NCC(=O)Nc1ccc(F)cc1]

2-(4-Fluoro-phenoxy)-N-[(4-fluoro-phenylcarbamoyl)-methyl]-acetamide

Yield: 96%

Melting point: 202 to 203° C. (recrystallization solvent: acetone)

$^1$H-NMR (400 MHz, CDCl$_3$): δ 4.14 (2H, d, J=5.9 Hz), 4.53 (2H, s), 6.88 (2H, dd, J=9.3, 4.1 Hz), 6.98-7.02 (4H, m), 7.34 (1H, br), 7.43 (2H, dd, J=9.0, 4.6 Hz), 7.99 (1H, br)

$^{13}$C-NMR (100 MHz, DMSO-d$_6$): δ 42.30, 67.44, 115.33 (d, J=22.3 Hz), 115.87 (d, J=23.2 Hz), 116.14 (d, J=8.3 Hz), 120.92 (d, J=7.4 Hz), 135.22 (d, J=1.7 Hz), 154.04 (d, J=1.7 Hz), 156.88 (d, J=236.5 Hz), 158.00 (d, J=239.0 Hz), 167.32, 168.16

IR (KBr): 3296, 1672 cm$^{-1}$

MS (EI): m/z 320 (M$^+$)

N-[(4-Bromophenylcarbamoyl)methyl]-2-(4-fluorophenoxy)acetamide

MM-10

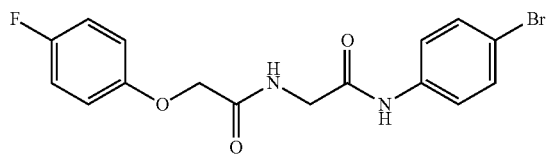 [SMILES: O=C(COc1ccc(F)cc1)NCC(=O)Nc1ccc(Br)cc1]

N-[(4-Bromo-phenylcarbamoyl)-methyl]-2-(4-fluoro-phenoxy)-acetamide

Yield: 92%

Melting point: 192 to 193° C. (recrystallization solvent: acetone)

$^1$H-NMR (400 MHz, CDCl$_3$): δ 4.15 (2H, d, J=5.6 Hz), 4.53 (2H. s), 6.88 (2H, dd, J=8.9, 4.3 Hz), 7.00 (2H, t, J=8.9 Hz), 7.38 (2H, d, J=9.1 Hz), 7.39 (1H, br), 7.42 (2H, d, J=9.1 Hz), 8.22 (1H, br)

$^{13}$C-NMR (100 MHz, DMSO-d$_6$): δ 42.40, 67.40, 114.83, 115.85 (d, J=23.2 Hz), 116.12 (d, J=8.3 Hz), 121.05, 131.56, 138.20, 154.01 (d, J=2.5 Hz), 156.85 (d, J=236.6 Hz), 167.59, 168.16

IR (KBr): 1686, 3256 cm$^{-1}$

MS (EI): m/z 380 (M$^+$)

2-(4-Bromophenoxy)-N-[(4-methoxyphenylcarbamoyl)methyl]acetamide

MM-11

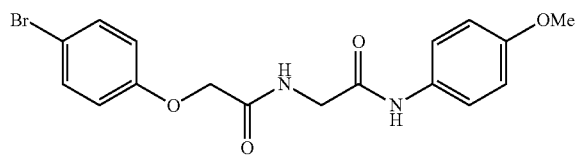 [SMILES: COc1ccc(NC(=O)CNC(=O)COc2ccc(Br)cc2)cc1]

2-(4-Bromo-phenoxy)-N-[(4-methoxy-phenylcarbamoyl)-methyl]acetamide

Yield: 79%

Melting point: 190 to 191° C. (recrystallization solvent: acetone)

$^1$H-NMR (400 MHz, CDCl$_3$): δ 3.79 (3H, s), 4.15 (2H, d, J=5.6 Hz), 4.55 (2H, s), 6.84 (2H, d, J=9.0 Hz), 6.86 (2H, d, J=8.9 Hz), 7.34 (1H, br), 7.38 (2H, d, J=9.0 Hz), 7.43 (2H, d, J=8.9 Hz), 7.78 (1H, br)

$^{13}$C-NMR (100 MHz, DMSO-d$_6$): δ 42.22, 55.12, 66.98, 112.66, 113.85, 117.07, 120.73, 131.91, 132.14, 155.21, 156.99, 166.80, 167.84

IR (KBr): 1655, 3261 cm$^{-1}$

MS (EI): m/z 392 (M$^+$)

2-(4-Fluorophenoxy)-N-[(4-methoxyphenylcarbamoyl)methyl]acetamide

MM-12

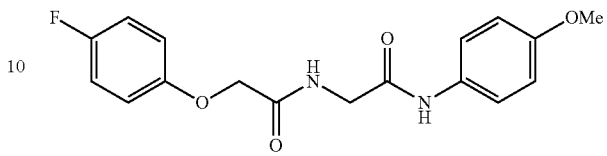

2-(4-Fluoro-phenoxy)-N-[(4-methoxy-phenylcarbamoyl)-methyl]-acetamide

Yield: 84%

Melting point: 185 to 186° C. (recrystallization solvent: acetone)

$^1$H-NMR (400 MHz, CDCl$_3$): δ 3.80 (3H, s), 4.16 (2H, d, J=5.6 Hz), 4.55 (2H, s), 6.86-6.92 (2H, m), 6.87 (2H, d, J=8.9 Hz), 7.02 (2H, t, J=8.5 Hz), 7.38 (1H, br), 7.39 (2H, d, J=8.9 Hz), 7.80 (1H, br)

$^{13}$C-NMR (100 MHz, DMSO-d$_6$): δ 42.24, 55.14, 67.45, 113.87, 115.88 (d, J=23.2 Hz), 116.15 (d, J=7.4 Hz), 120.76, 131.96, 154.05 (d, J=1.7 Hz), 155.24, 156.88 (d, J=236.5 Hz) 166.86, 168.10

IR (KBr): 1659, 3279 cm$^{-1}$

MS (EI): m/z 332 (M$^+$)

2-(4-Bromophenoxy)-N-(4-cyclohexylcarbamoylmethyl)acetamide

MM-13

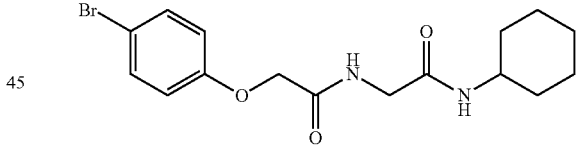

2-(4-Bromo-phenoxy)-N-cyclohexylcarbamoylmethyl-acetamide

Yield: 78%

Melting point: 210 to 211° C. (recrystallization solvent: acetone)

$^1$H-NMR (400 MHz, CDCl$_3$): δ 1.12-1.19 (3H, m), 1.31-1.38 (3H, m), 1.53-1.61 (1H, m), 1.67-1.75 (2H, m), 1.88-1.93 (2H, m), 3.76 (1H, br), 3.96 (2H, d, J=5.4 Hz), 4.51 (2H, s), 5.64 (1H, br), 6.83 (2H, d, J=9.1 Hz), 7.42 (2H, d, J=9.1 Hz)

$^{13}$C-NMR (100 MHz, DMSO-d$_6$): δ 24.53, 25.17, 32.37, 41.59, 47.53, 66.94, 112.63, 117.03, 132.14, 156.97, 167.19, 167.56

IR (KBr): 1653, 3290 cm$^{-1}$

MS (EI): m/z 370 (M$^+$)

N-(Cyclohexylcarbamoylmethyl)-2-(4-fluorophenoxy)acetamide

MM-14

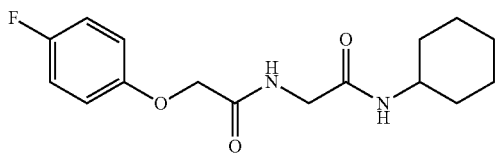 [SMILES: O=C(COc1ccc(F)cc1)NCC(=O)NC1CCCCC1]

N-Cyclohexylcarbamoylmethyl-2-(4-fluoro-phenoxy)-acetamide

Yield: 91%

Melting point: 184 to 185° C. (recrystallization solvent: acetone)

$^1$H-NMR (400 MHz, CDCl$_3$): δ 1.12-1.18 (3H, m), 1.31-1.40 (3H, m), 1.53-1.64 (1H, m), 1.67-1.75 (2H, m), 1.85-1.95 (2H, m), 3.78 (1H, br), 3.96 (2H, d, J=5.4 Hz), 4.50 (2H, s), 5.68 (1H, br), 6.89 (2H, dd, J=8.8, 4.3 Hz), 7.01 (2H, t, J=8.8 Hz)

$^{13}$C-NMR (100 MHz, DMSO-d$_6$): δ 24.56, 25.20, 32.40, 41.61, 47.59, 67.42, 115.88 (d, J=23.2 Hz), 116.11 (d, J=8.3 Hz), 154.03 (d, J=1.7 Hz), 156.88 (d, J=236.5 Hz), 167.27, 167.83

IR (KBr): 1653, 3292 cm$^{-1}$

MS (EI): m/z 308 (M$^+$)

2-(4-Bromophenoxy)-N-[(2,6-difluorophenylcarbamoyl)methyl]acetamide

MM-15

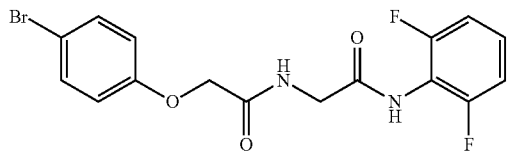

2-(4-Bromo-phenoxy)-N-[(2,6-difluoro-phenylcarbamoyl)-methyl]-acetamide

Yield: 100%

Melting point: 173 to 174° C.

$^1$H-NMR (400 MHz, CDCl$_3$): δ 4.22 (2H, d, J=1.5 Hz), 4.53 (2H, s), 6.81 (2H, d, J=9.0 Hz), 6.95 (2H, t, J=8.4 Hz), 7.04 (1H, br), 7.21-7.24 (1H, m), 7.40 (2H, d, J=9.0 Hz), 7.50 (1H, br)

IR (KBr): 1661, 3261 cm$^{-1}$

N-(Benzylcarbamoylmethyl)-2-(4-bromophenoxy)acetamide

MM-16

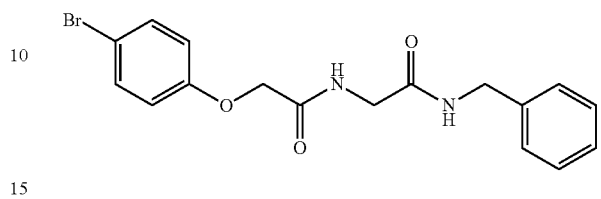

N-(Benzylcarbamoyl-methyl)-2-(4-bromo-phenoxy)-acetamide

Yield: 98%

Melting point: 195 to 196° C. (recrystallization solvent: acetone)

$^1$H-NMR (400 MHz, CDCl$_3$): δ 4.02 (2H, d, J=5.4 Hz), 4.44 (2H, d, J=5.9 Hz), 4.48 (2H, s), 6.12 (1H, br), 6.79 (2H, d, J=9.1 Hz), 6.98 (1H, br), 7.24-7.35 (5H, m), 7.38 (2H, d, J=9.1 Hz)

$^{13}$C-NMR (100 MHz, DMSO-d$_6$): δ 41.80, 41.99, 66.99, 112.61, 117.04, 126.73, 127.15, 128.21, 132.13, 139.30, 156.99, 167.80, 168.55

IR (KBr): 1653, 3277 cm$^{-1}$

MS (EI): m/z 376 (M$^+$)

N-(Benzylcarbamoylmethyl)-2-(4-fluorophenoxy)acetamide

MM-17

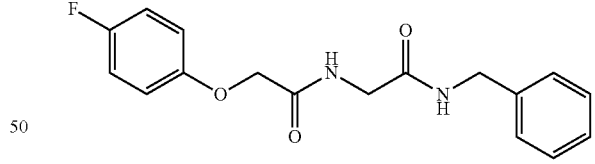

N-(Benzylcarbamoyl-methyl)-2-(4-fluoro-phenoxy)-acetamide

Yield: 88%

Melting point: 165 to 166° C. (recrystallization solvent: acetone)

$^1$H-NMR (400 MHz, CDCl$_3$): δ 4.03 (2H, d, J=5.6 Hz), 4.45 (2H, d, J=5.6 Hz), 4.48 (2H, s), 6.16 (1H, br), 6.85 (2H, dd, J=8.9, 4.1 Hz), 6.97 (2H, t, J=8.9 Hz), 7.09 (1H, br), 7.22-7.35 (5H, m)

IR (KBr): 1655, 3263 cm$^{-1}$

N-[(4-Methoxy-2-methylphenylcarbamoyl)methyl]-2-(4-methoxyphenoxy)acetamide

MM-18

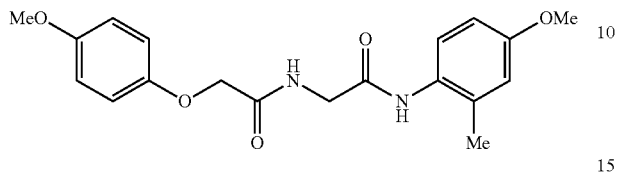

N-[(4-Methoxy-2-methyl-phenylcarbamoyl)-methyl]-2-(4-methoxy-phenoxy)-acetamide

Yield: 94%

Melting point: 143 to 144° C. (recrystallization solvent: acetone)

$^1$H-NMR (400 MHz, CDCl$_3$): δ 2.21 (3H, s), 3.76 (3H, s), 3.78 (3H, s), 4.17 (2H, d, J=6.1 Hz), 4.53 (2H, s), 6.73-6.75 (2H, m), 6.84 (2H, d, J=9.5 Hz), 6.88 (2H, d, J=9.5 Hz), 7.39 (1H, br), 7.53 (1H, d, J=9.5 Hz), 7.64 (1H, br)

$^{13}$C-NMR (100 MHz, DMSO-d$_6$): δ 17.95, 42.01, 55.08, 55.33, 67.61, 111.14, 114.56, 115.31, 115.72, 126.66, 128.81, 134.02, 151.70, 153.82, 156.80, 167.49, 168.41

IR (KBr): 1660, 3273 cm$^{-1}$

MS (EI): m/z 358 (M$^+$)

N-[(4-Methoxy-2-methylphenylcarbamoyl)methyl]-2-(3-methoxyphenoxy)acetamide

MM-19

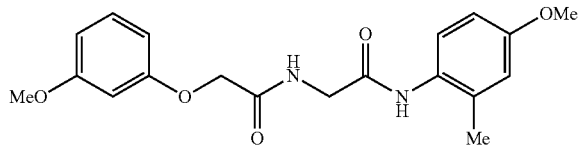 [SMILES: COc1cccc(OCC(=O)NCC(=O)Nc2ccc(OC)cc2C)c1]

N-[(4-Methoxy-2-methyl-phenylcarbamoyl)-methyl]-2-(3-methoxy-phenoxy)-acetamide

Yield: 70%

Melting point: 115 to 116° C.

$^1$H-NMR (400 MHz, CDCl$_3$): δ 2.21 (3H, s), 3.78-3.81 (6H, m), 4.18 (2H, d, J=5.9 Hz), 4.57 (2H, s), 6.51-6.53 (2H, m), 6.58 (1H, d, J=7.8 Hz), 6.73-6.75 (2H, m), 7.21 (1H, t, J=7.8 Hz), 7.38 (1H, br), 7.52 (1H, d, J=9.5 Hz), 7.65 (1H, br)

IR (KBr): 1659, 3331 cm$^{-1}$

2-(4-Chlorophenoxy)-N-[(2,6-difluorophenylcarbamoyl)methyl]acetamide

MM-20

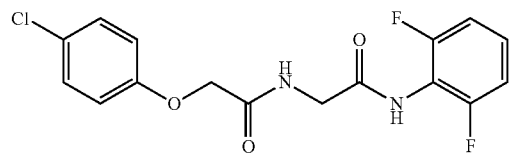 [SMILES: O=C(COc1ccc(Cl)cc1)NCC(=O)Nc1c(F)cccc1F]

2-(4-Chloro-phenoxy)-N-[(2,6-difluoro-phenylcarbamoyl)-methyl]acetamide

Yield: 68%

Melting point: 184 to 185° C.

$^1$H-NMR (400 MHz, CDCl$_3$): δ 4.22 (2H, d, J=1.0 Hz), 4.54 (2H, s), 6.86 (2H, d, J=9.0 Hz), 6.96 (2H, t, J=8.2 Hz), 7.22-7.26 (1H, m), 7.26 (2H, d, J=9.0 Hz), 7.30 (1H, br), 7.50 (1H, br)

IR (KBr): 1663, 3261 cm$^{-1}$

N-[(2,6-Difluorophenylcarbamoyl)methyl]-2-(4-phenoxyphenoxy)acetamide

MM-21

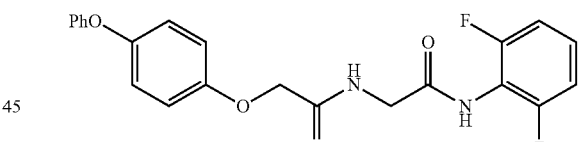

N-[(2,6-Difluoro-phenylcarbamoyl)-methyl]-2-(4-phenoxy-phenoxy)-acetamide

Yield: 84%

Melting point: 164 to 165° C. (recrystallization solvent: toluene)

$^1$H-NMR (400 MHz, CDCl$_3$): 4.25 (2H, d, J=3.2 Hz), 4.55 (2H, s), 6.89-7.01 (9H, m), 7.05 (1H, t, J=7.4 Hz), 7.29 (2H, t, J=7.4 Hz), 7.37 (1H, br), 7.60 (1H, br)

$^{13}$C-NMR (100 MHz, DMSO-d$_6$): δ 41.58, 67.36, 111.88 (dd, J=17.8, 5.4 Hz), 114.19 (t, J=16.5 Hz), 116.14, 117.47, 120.58, 122.73, 128.06 (t, J=10.3 Hz), 129.92, 150.06, 154.04, 157.73 (dd, J=248.1, 5.8 Hz), 157.82, 167.91, 168.26

IR (KBr): 1665, 3273 cm$^{-1}$

71

N-[(2,6-Difluorophenylcarbamoyl)methyl]-2-m-tolyloxyacetamide

MM-22

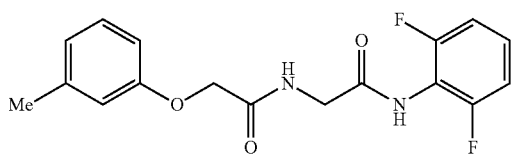 [SMILES: Cc1cccc(OCC(=O)NCC(=O)Nc2c(F)cccc2F)c1]

N-[(2,6-Difluoro-phenylcarbamoyl)-methyl]-2-m-tolyloxy-acetamide

Yield: 82%

Melting point: 161 to 162° C. (recrystallization solvent: toluene)

$^1$H-NMR (400 MHz, CDCl$_3$): δ 2.33 (3H, s), 4.25 (2H, s), 4.57 (2H, s), 6.74 (1H, d, J=8.3 Hz), 6.77 (1H, s), 6.83 (1H, d, J=8.3 Hz), 6.97 (2H, t, J=7.9 Hz), 7.19 (1H, t, J=7.9 Hz), 7.20-7.27 (1H, m), 7.38 (1H, br), 7.61 (1H, br)

$^{13}$C-NMR (100 MHz, DMSO-d$_6$): δ 21.09, 41.56, 66.80, 111.87 (dd, J=19.0, 5.8 Hz), 114.19 (t, J=16.5 Hz), 115.44, 121.97, 128.04 (t, J=9.9 Hz), 128.21, 129.25, 139.03, 157.69, 157.73 (dd, J=248.1, 5.8 Hz), 167.88, 168.30

IR (KBr): 1680, 3258 cm$^{-1}$

N-[(2,6-Difluorophenylcarbamoyl)methyl]-2-(4-methoxyphenoxy)acetamide

MM-23

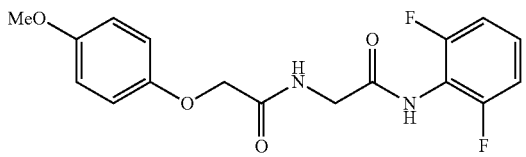 [SMILES: COc1ccc(OCC(=O)NCC(=O)Nc2c(F)cccc2F)cc1]

N-[(2,6-Difluoro-phenylcarbamoyl)-methyl]-2-(4-methoxy-phenoxy)-acetamide

Yield: 95%

Melting point: 164 to 165° C. (recrystallization solvent: toluene)

$^1$H-NMR (400 MHz, CDCl$_3$): δ 3.74 (3H, s), 4.23 (2H, s), 4.52 (2H, s), 6.82 (2H, d, J=9.1 Hz), 6.86 (2H, d, J=9.1 Hz), 6.95 (2H, t, J=8.1 Hz), 7.24-7.25 (1H, m), 7.36 (1H, br), 7.61 (1H, br)

$^{13}$C-NMR (100 MHz, DMSO-d$_6$): δ 41.54, 55.35, 67.60, 111.88 (dd, J=17.8, 5.4 Hz), 114.19 (t, J=17.0 Hz), 114.59, 115.75, 128.04 (t, J=12.0 Hz), 151.73, 153.85, 157.72 (dd, J=249.4, 6.2 Hz), 167.90, 168.46

IR (KBr): 1666, 3271 cm$^{-1}$

72

N-[(2,6-Difluorophenylcarbamoyl)methyl]-2-(4-fluorophenoxy)acetamide

MM-24

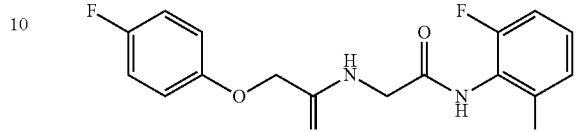

N-[(2,6-Difluoro-phenylcarbamoyl)-methyl]-2-(4-fluoro-phenoxy)-acetamide

Yield: 34%

Melting point: 194 to 195° C. (recrystallization solvent: toluene)

$^1$H-NMR (400 MHz, CDCl$_3$): δ 4.27 (2H, s), 4.54 (2H, s), 6.89 (2H, dd, J=9.1, 4.3 Hz), 6.95-7.03 (4H, m), 7.22-7.26 (1H, m), 7.39 (1H, br), 7.67 (1H, br)

IR (KBr): 1663, 3261 cm$^{-1}$ 2-(4-Bromophenoxy)-N-[(2,6-difluorophenylthiocarbamoyl)methyl]acetamide

MM-25

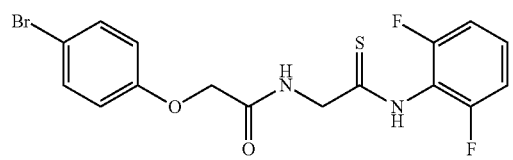

2-(4-Bromo-phenoxy)-N-[(2,6-difluoro-phenylthio-carbamoyl)-methyl]-acetamide

Yield: 66%

Melting point: 174 to 175° C. (recrystallization solvent: toluene)

$^1$H-NMR (400 MHz, CDCl$_3$): δ 4.57 (2H, s), 4.59 (2H. s), 6.84 (2H, d, J=9.0 Hz), 7.00 (2H, t, J=7.7 Hz), 7.33 (1H, t, J=7.7 Hz), 7.43 (2H, d, J=9.0 Hz), 7.62 (1H, br), 9.46 (1H, br)

$^{13}$C-NMR (100 MHz, DMSO-d$_6$): δ 48.89, 67.03, 112.11 (dd, J=18.2, 4.1 Hz), 112.63, 116.18 (t, J=16.5 Hz), 117.09, 129.74 (t, J=9.5 Hz), 132.12, 156.99, 157.49 (dd, J=250.6, 5.8 Hz), 167.99, 203.40

IR (KBr): 1670, 3020, 3207 cm$^{-1}$

73

N-[(2,6-Difluorophenylthiocarbamoyl)methyl]-2-(4-methoxyphenoxy)acetamide

MM-26

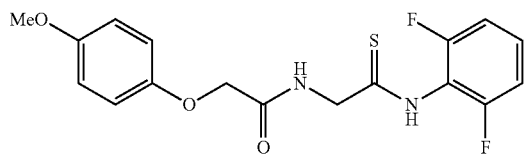 [SMILES: COc1ccc(OCC(=O)NCC(=S)Nc2c(F)cccc2F)cc1]

N-[(2,6-Difluoro-phenylthiocarbamoyl)-methyl]-2-(4-methoxy-phenoxy)-acetamide

Yield: 75%

Melting point: 160 to 161° C. (recrystallization solvent: toluene)

$^1$H-NMR (400 MHz, CDCl$_3$): δ 3.74 (3H, s), 4.54 (2H, s), 4.57 (2H, d, J=6.1 Hz), 6.83 (2H, d, J=9.5 Hz), 6.87 (2H, d, J=9.5 Hz), 6.98 (2H, t, J=8.1 Hz), 7.31 (1H, t, J=8.1 Hz), 7.57 (1H, br), 9.45 (1H, br)

$^{13}$C-NMR (100 MHz, DMSO-d$_6$): δ 48.90, 55.35, 67.64, 112.13 (dd, J=18.6, 4.5 Hz), 114.58, 115.75, 116.21 (t, J=16.5 Hz), 129.75 (t, J=9.9 Hz), 151.71, 153.83, 157.52 (dd, J=249.8, 5.0 Hz), 168.53, 203.48

IR (KBr): 1670, 3007, 3182 cm$^{-1}$ 2-(4-Bromophenoxy)-N-[(2-methylbenzylcarbamoyl)methyl]acetamide

MM-27

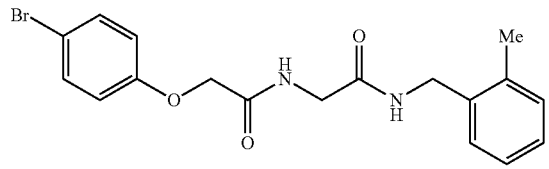 [SMILES: Cc1ccccc1CNC(=O)CNC(=O)COc1ccc(Br)cc1]

2-(4-Bromo-phenoxy)-N-[(2-methyl-benzylcarbamoyl)-methyl]-acetamide

Yield: 47%

Melting point: 174 to 175° C. (recrystallization solvent: toluene)

$^1$H-NMR (400 MHz, CDCl$_3$): δ 2.30 (3H, s), 4.01 (2H, d, J=5.4 Hz), 4.44 (2H, d, J=5.6 Hz), 4.46 (2H, s), 6.06 (1H, br), 6.79 (2H, d, J=9.1 Hz), 7.14-7.24 (5H, m), 7.38 (2H, d, J=9.1 Hz)

IR (KBr): 1649, 3275 cm$^{-1}$

74

N-[(4-Bromophenylcarbamoyl)methyl]-2-(4-bromophenoxy)acetamide

MM-28

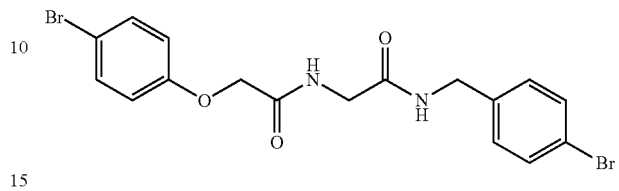

N-[(4-Bromo-benzylcarbamoyl)-methyl]-2-(4-bromo-phenoxy)-acetamide

Yield: 76%

Melting point: 208 to 209° C. (recrystallization solvent: acetone)

$^1$H-NMR (400 MHz, CDCl$_3$): δ 4.04 (2H, d, J=5.4 Hz), 4.41 (2H, d, J=6.1 Hz), 4.50 (2H, s), 6.26 (1H, br), 6.81 (2H, d, J=9.0 Hz), 7.14 (2H, d, J=8.5 Hz), 7.20-7.35 (1H, m), 7.41 (2H, d, J=9.0 Hz), 7.46 (2H, d, J=8.5 Hz)

IR (KBr): 1655, 3271 cm$^{-1}$

N-[(4-bromo-2-fluorobenzylcarbamoyl)methyl]-2-(4-bromophenoxy)acetamide

MM-29

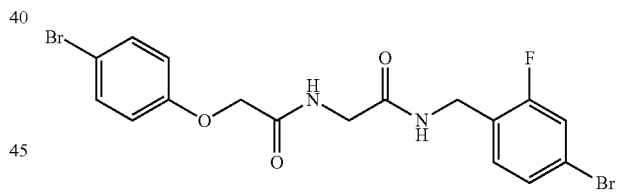

N-[(4-Bromo-2-fluoro-benzylcarbamoyl)-methyl]-2-(4-bromo-phenoxy)-acetamide

Yield: 85%

Melting point: 179 to 180° C. (recrystallization solvent: toluene)

$^1$H-NMR (400 MHz, CDCl$_3$): δ 4.02 (2H, d, J=5.6 Hz), 4.45 (2H, d, J=5.9 Hz), 4.50 (2H, s), 6.30 (1H, br), 6.81 (2H, d, J=9.0 Hz), 7.19-7.26 (3H, m), 7.41 (2H, d, J=9.0 Hz), 7.79 (1H, br)

$^{13}$C-NMR (100 MHz, DMSO-d$_6$): δ 35.60, 41.79, 66.96, 112.64, 117.02, 118.38 (d, J=24.8 Hz), 120.07 (d, J=9.1 Hz), 125.62 (d, J=14.9 Hz), 127.37 (d, J=3.3 Hz), 131.04 (d, J=5.0 Hz), 132.12, 156.96, 159.81 (d, J=249.8 Hz), 167.89, 168.86

IR (KBr): 1661, 3279 cm$^{-1}$

2-(4-Bromophenoxy)-N-[(3-bromophenylcarbamoyl)methyl]acetamide

MM-30

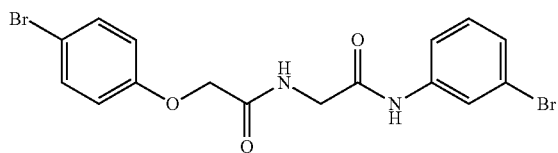 [SMILES: O=C(COc1ccc(Br)cc1)NCC(=O)Nc1cccc(Br)c1]

2-(4-Bromo-phenoxy)-N-[(3-bromo-phenylcarbamoyl)-methyl]acetamide

Yield: 70%

Melting point: 227 to 228° C.

$^1$H-NMR (400 MHz, CDCl$_3$): δ 4.13 (2H, d, J=5.9 Hz), 4.53 (2H, s), 6.81 (2H, d, J=9.1 Hz), 7.16 (1H, t, J=8.1 Hz), 7.22-7.35 (2H, m), 7.37 (1H, d, J=8.1 Hz), 7.41 (2H, d, J=9.1 Hz), 7.74 (1H, s), 8.18 (1H, br)

$^{13}$C-NMR (100 MHz, DMSO-d$_6$): δ 42.45, 66.97, 112.71, 117.08, 117.90, 121.48, 121.57, 125.93, 130.80, 132.15, 140.37, 156.98, 167.77, 168.00

IR (KBr): 1661, 3281 cm$^{-1}$

N-[(3-Bromophenylcarbamoyl)methyl]-2-(4-methoxyphenoxy)acetamide

MM-31

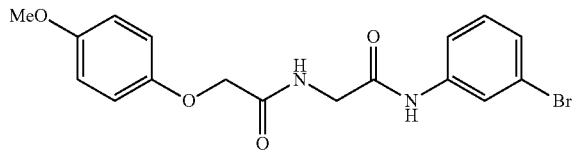 [SMILES: COc1ccc(OCC(=O)NCC(=O)Nc2cccc(Br)c2)cc1]

N-[(3-Bromo-phenylcarbamoyl)-methyl]-2-(4-methoxy-phenoxy)-acetamide

Yield: 73%

Melting point: 174 to 175° C.

$^1$H-NMR (400 MHz, CDCl$_3$): δ 3.75 (3H, s), 4.16 (2H, d, J=5.6 Hz), 4.53 (2H, s), 6.83 (2H, d, J=9.3 Hz), 6.87 (2H, d, J=9.3 Hz), 7.16 (1H, t, J=7.8 Hz), 7.22-7.24 (1H, m), 7.39 (1H, d, J=7.8 Hz), 7.40 (1H, br), 7.74 (1H, s), 8.33 (1H, br)

$^{13}$C-NMR (100 MHz, DMSO-d$_6$): δ 42.43, 55.36, 67.59, 114.60, 115.77, 117.90, 121.48, 121.57, 125.92, 130.81, 140.41, 151.70, 153.87, 167.83, 168.53

IR (KBr): 1663, 3312 cm$^{-1}$

2-(4-Bromophenoxy)-N-[(3-chlorophenylcarbamoyl)methyl]acetamide

MM-32

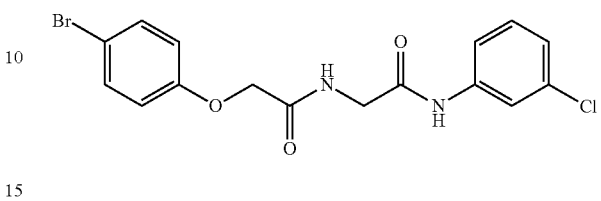

2-(4-Bromo-phenoxy)-N-[(3-chloro-phenylcarbamoyl)-methyl]-acetamide

Yield: 71%

Melting point: 205 to 206° C. (recrystallization solvent: toluene)

$^1$H-NMR (400 MHz, CDCl$_3$): δ 4.14 (2H, d, J=5.9 Hz), 4.54 (2H, s), 6.82 (2H, d, J=9.0 Hz), 7.09 (1H, d, J=8.3 Hz), 7.21-7.28 (2H, m), 7.30 (1H, d, J=8.3 Hz), 7.41 (2H, d, J=9.0 Hz), 7.61 (1H, s), 8.10 (1H, br)

$^{13}$C-NMR (100 MHz, DMSO-d$_6$): δ 42.42, 66.95, 112.70, 117.07, 117.49, 118.60, 123.01, 130.47, 132.14, 133.08, 140.23, 156.97, 167.77, 167.99

IR (KBr): 1661, 3281 cm$^{-1}$

2-(4-Bromophenoxy)-N-[(3-nitrophenylcarbamoyl)methyl]acetamide

MM-33

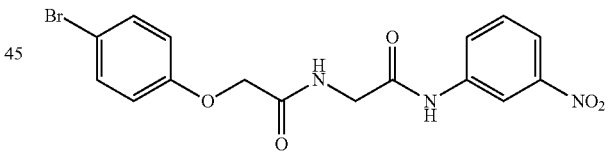

2-(4-Bromo-phenoxy)-N-[(3-nitro-phenylcarbamoyl)-methyl]-acetamide

Yield: 77%

Melting point: 197 to 198° C.

$^1$H-NMR (400 MHz, CDCl$_3$): δ 4.22 (2H, d, J=5.9 Hz), 4.58 (2H, s), 6.84 (2H, d, J=8.7 Hz), 7.41 (1H, br), 7.42 (2H, d, J=8.7 Hz), 7.48 (1H, t, J=8.5 Hz), 7.90 (1H, d, J=8.5 Hz), 7.96 (1H, d, J=8.5 Hz), 8.39 (1H, s), 8.76 (1H, br)

$^{13}$C-NMR (100 MHz, DMSO-d$_6$): δ 42.51, 66.95, 112.69, 113.22, 117.06, 117.81, 125.08, 130.20, 132.13, 139.91, 147.92, 156.96, 168.07, 168.21

IR (KBr): 1676, 3265 cm$^{-1}$ 2-(4-Benzyloxyphenoxy)-N-[(2,6-difluorophenylcarbamoyl)methyl]acetamide

MM-34

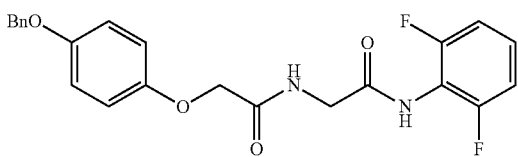 [SMILES: O=C(COc1ccc(OCc2ccccc2)cc1)NCC(=O)Nc1c(F)cccc1F]

2-(4-Benzyloxy-phenoxy)-N-[(2,6-difluoro-phenylcarbamoyl)-methyl]-acetamide

Yield: 82%
Melting point: 145 to 146° C.
$^1$H-NMR (400 MHz, CDCl$_3$): δ 4.26 (2H, s), 4.53 (2H, s), 5.00 (2H, s), 6.87 (2H, d, J=9.1 Hz), 6.92 (2H, d, J=9.1 Hz), 6.96 (2H, t, J=8.1 Hz), 7.30-7.42 (7H, m), 7.66 (1H, br)
IR (KBr): 1663, 3260 cm$^{-1}$ N-[(4-Iodophenylcarbamoyl)methyl]-2-m-tolyloxyacetamide

MM-36

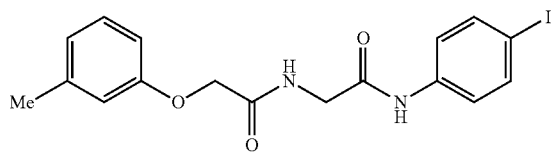 [SMILES: Cc1cccc(OCC(=O)NCC(=O)Nc2ccc(I)cc2)c1]

N-[(4-Iodo-phenylcarbamoyl)-methyl]-2-m-tolyloxy-acetamide

Yield: 69%
Melting point: 192 to 193° C. (recrystallization solvent: toluene)
$^1$H-NMR (400 MHz, CDCl$_3$): δ 2.34 (3H, s), 4.16 (2H, d, J=5.9 Hz), 4.57 (2H, s), 6.74 (1H, d, J=7.7 Hz), 6.77 (1H, s), 6.86 (1H, d, J=7.7 Hz), 7.20 (1H, t, J=7.7 Hz), 7.26-7.28 (2H, m), 7.37 (1H, br), 7.62 (2H, J=8.8 Hz), 8.21 (1H, br)
$^{13}$C-NMR (100 MHz, DMSO-d$_6$): δ 21.10, 42.42, 66.75, 86.75, 111.73, 115.40, 121.30, 121.98, 129.23, 137.40, 138.65, 139.02, 157.64, 167.59, 168.31
IR (KBr): 1663, 3277 cm$^{-1}$ N-[(4-Benzyloxyphenylcarbamoyl)methyl]-2-m-tolyloxyacetamide

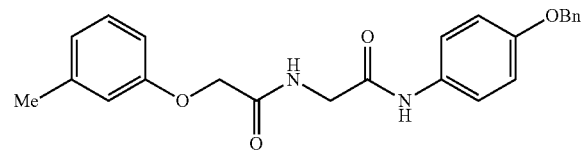 [SMILES: Cc1cccc(OCC(=O)NCC(=O)Nc2ccc(OCc3ccccc3)cc2)c1]

N-[(4-Benzyloxy-phenylcarbamoyl)-methyl]-2-m-tolyloxy-acetamide

Yield: 96%
Melting point: 169 to 170° C.

$^1$H-NMR (400 MHz, CDCl$_3$): δ 2.33 (3H, s), 4.16 (2H, d, J=5.6 Hz), 4.57 (2H, s), 5.05 (2H, s), 6.74 (1H, d, J=7.8 Hz), 6.77 (1H, s), 6.85 (1H, d, J=7.8 Hz), 6.93 (2H, d, J=9.0 Hz), 7.20 (1H, t, J=7.8 Hz), 7.32-7.43 (8H, m), 7.91 (1H, br)
IR (KBr): 1663, 3329 cm$^{-1}$

Example 3

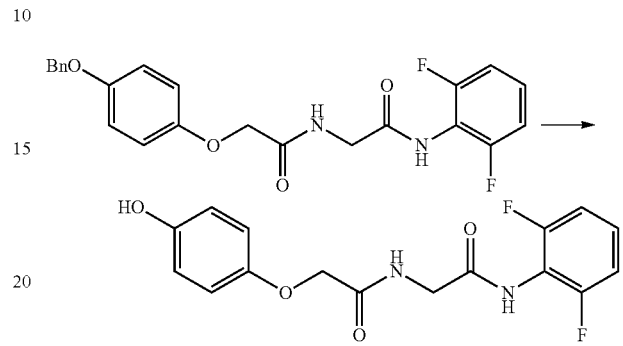

Palladium hydroxide (5 mg) was added to a methanol solution (10 mL) of 2-(4-benzyloxyphenoxy)-N-[(2,6-difluorophenylcarbamoyl)methyl]acetamide (91 mg, 0.21 mmol) in a hydrogen atmosphere, and the mixture was stirred at room temperature overnight.

After filtering the reaction mixture through celite, the solvent was evaporated to obtain N-[(2,6-difluorophenylcarbamoyl)methyl]-2-(4-hydroxyphenoxy)acetamide (72 mg) as a colorless crystalline substance.

MM-35

Yield: 100%
Melting point: 197 to 198° C.
$^1$H-NMR (400 MHz, CDCl$_3$): δ 3.98 (2H, s), 4.41 (2H, s), 6.67 (2H, d, J=8.8 Hz), 6.81 (2H, d, J=8.8 Hz), 7.14 (2H, t, J=7.6 Hz), 7.32 (1H, t, J=7.6 Hz), 8.35 (1H, br), 9.72 (1H, br)
IR (KBr): 1680, 3261 cm$^{-1}$ Example 4

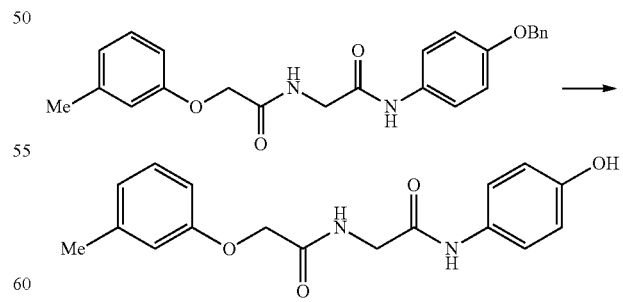

Palladium hydroxide (10 mg) was added to a methanol-ethanol (5:1) solution (60 mL) of N-(4-benzyloxyphenylcarbamoyl)-2-m-tolyloxyacetamide (200 mg, 0.49 mmol) in a hydrogen atmosphere, and the mixture was stirred at room temperature overnight.

After filtering the reaction mixture through celite, the solvent was evaporated to obtain N-[(4-hydroxyphenylcarbamoyl)methyl]-2-m-tolyloxyacetamide (154 mg) as a colorless crystalline substance.

MM-37

Yield: 99%
Melting point: 186 to 187° C.
$^1$H-NMR (400 MHz, DMSO-$d_6$): δ 2.27 (3H, s), 3.90 (2H, d, J=5.4 Hz), 4.51 (2H, s), 6.68 (2H, d, J=8.4 Hz), 6.77-6.82 (3H, m), 7.17 (1H, t, J=7.7 Hz), 7.33 (2H, d, J=8.4 Hz), 8.30 (1H, br), 9.20 (1H, br), 9.71 (1H, m)
$^{13}$C-NMR (100 MHz, DMSO-$d_6$): δ 21.13, 42.26, 66.82, 111.78, 115.15, 115.45, 121.04, 122.02, 129.29, 130.43, 139.09, 153.52, 157.72, 166.69, 168.27
IR (KBr): 1663, 3339 cm$^{-1}$ Example 5

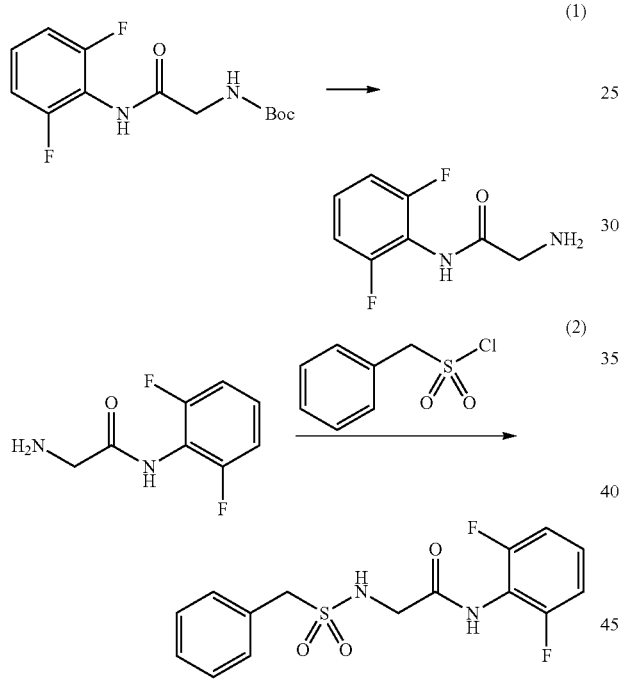

(1) Trifluoroacetic acid (1.0 mL, 13.6 mmol) was added to a methylene chloride (5.7 mL) solution of [(2,6-difluorophenylcarbamoyl)methyl]carbamic acid tert-butyl ester (384 mg, 1.34 mmol) in an argon atmosphere, and the mixture was stirred at room temperature overnight.

A saturated sodium bicarbonate solution was added to the reaction mixture at 0° C. until the aqueous layer became basic.

The organic layer was extracted with methylene chloride, dried over potassium carbonate, and filtered.

The solvent was evaporated to obtain 2-amino-N-(2,6-difluorophenyl)acetamide (colorless crystals) (122 mg, yield: 49%).

(2) Diethylamine (0.17 mL, 1.22 mmol) was added to a methylene chloride (4 mL) solution of 2-amino-N-(2,6-difluorophenyl)acetamide (114 mg, 0.61 mmol) in an argon atmosphere. After the addition of benzylsulfamoyl chloride (114 mg, 0.67 mmol) at 0° C., the mixture was stirred at room temperature overnight.

After evaporating the solvent, the residue was purified by silica gel column chromatography (15 g, hexane:acetone=4:1 to 3:1) to obtain N-(2,6-difluorophenyl)-2-phenylmethanesulfonylaminoacetamide (colorless crystals) (113 mg, DR-1).

Yield: 54%
Melting point: 141 to 142° C. (recrystallization solvent: toluene)
$^1$H-NMR (400 MHz, CDCl$_3$): δ 3.77 (2H, s), 4.35 (2H, s), 5.00 (1H, br), 6.94 (2H, t, J=8.2 Hz), 7.19-7.24 (1H, m), 7.37-7.43 (6H, m)

Example 6

The following compounds were obtained in the same manner as in Example 5.

N-(2,6-difluorophenyl)-2-(toluene-4-phenylmethanesulfonylamino)acetamide

DR-2

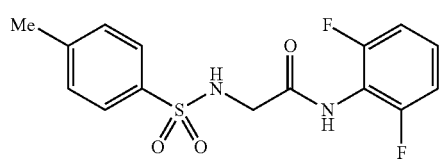 [SMILES: Cc1ccc(S(=O)(=O)NCC(=O)Nc2c(F)cccc2F)cc1]

N-(2,6-Difluoro-phenyl)-2-(toluene-4-sulfonylamino)-acetamide

Yield: 70%
Melting point: 129 to 130° C. (recrystallization solvent: toluene)
$^1$H-NMR (400 MHz, CDCl$_3$): δ 2.42 (3H, s), 3.79 (2H, s), 5.36 (1H, br), 6.93 (2H, t, J=8.2 Hz), 7.17-7.24 (1H, m), 7.32 (2H, d, J=8.2 Hz), 7.72 (1H, br), 7.76 (2H, d, J=8.2 Hz)

N-(1-phenylethyl)-2-phenylmethanesulfonylaminoacetamide

DR-3

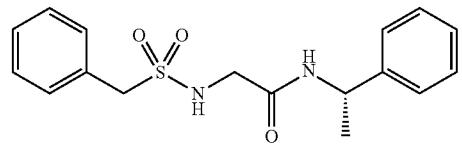 [SMILES: C[C@H](NC(=O)CNS(=O)(=O)Cc1ccccc1)c1ccccc1]

N-(1-Phenyl-ethyl)-2-phenylmethanesulfonylaminoacetamide

Yield: 38%
Melting point: 147 to 148° C. (recrystallization solvent: toluene)
$^1$H-NMR (400 MHz, CDCl$_3$): δ 1.46 (3H, d, J=7.1 Hz), 3.52 (2H, s), 4.27 (2H, s), 4.90 (1H, br), 5.06 (1H, quint, J=7.1 Hz), 6.27 (1H, br), 7.24-7.35 (10H, m)

81

N-(1-Phenylethyl)-2-(toluene-4-methanesulfonylamino)acetamide

DR-4

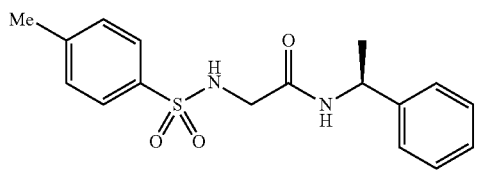 [SMILES: Cc1ccc(S(=O)(=O)NCC(=O)N[C@@H](C)c2ccccc2)cc1]

N-(1-Phenyl-ethyl)-2-(toluene-4-sulfonylamino)-acetamide

Yield: 59%
$^1$H-NMR (400 MHz, CDCl$_3$): δ 1.42 (3H, d, J=7.1 Hz), 2.40 (3H, s), 3.53 (2H, s), 5.02 (1H, quint, J=7.1 Hz), 5.25 (1H, br), 6.52 (1H, br), 7.22-7.32 (7H, m), 7.70 (2H, d, J=8.3 Hz)

Phenylmethanesulfonylaminoacetic acid benzyl ester

DR-5

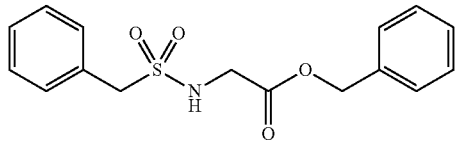 [SMILES: O=C(CNS(=O)(=O)Cc1ccccc1)OCc1ccccc1]

Phenylmethanesulfonylamino-acetic acid benzyl ester

Yield: 30%
Melting point: 92 to 93° C.
$^1$H-NMR (400 MHz, CDCl$_3$): δ 3.71 (2H, d, J=5.4 Hz), 4.30 (2H, s), 4.69 (1H, br), 5.15 (2H, s), 7.30-7.42 (10H, m)

(Toluene-4-sulfonylamino)acetic acid benzyl ester

DR-6

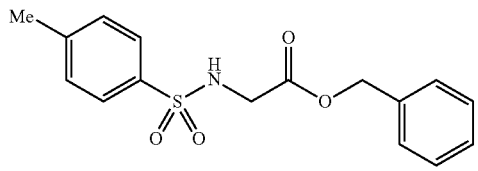 [SMILES: Cc1ccc(S(=O)(=O)NCC(=O)OCc2ccccc2)cc1]

(Toluene-4-sulfonylamino)-acetic acid benzyl ester

Yield: 70%
Helv. Chim. Acta, 1996, 79, 1843-1862.

82

N-(4-Methylbenzyl)-2-(toluene-4-sulfonylamino)acetamide

DR-8

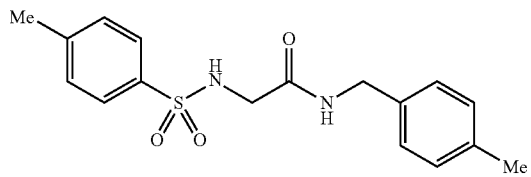 [SMILES: Cc1ccc(CNC(=O)CNS(=O)(=O)c2ccc(C)cc2)cc1]

N-(4-Methyl-benzyl)-2-(toluene-4-sulfonylamino)-acetamide

Yield: 31%
$^1$H-NMR (400 MHz, CDCl$_3$): δ 2.32 (3H, s), 2.41 (3H, s), 3.58 (2H, d, J=5.9 Hz), 4.35 (2H, d, J=5.6 Hz), 5.07 (1H, br), 6.42 (1H, br), 7.10 (2H, d, J=7.2 Hz), 7.12 (2H, d, J=7.2 Hz), 7.29 (2H, d, J=8.2 Hz), 7.71 (2H, d, J=8.2 Hz)

N-(4-Bromobenzyl)-2-(toluene-4-sulfonylamino)acetamide

DR-10

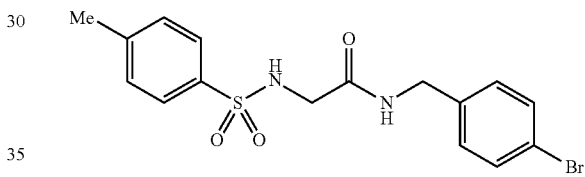

N-(4-Bromo-benzyl)-2-(toluene-4-sulfonylamino)-acetamide

Yield: 50%
Melting point: 207 to 208° C. (recrystallization solvent: acetone)
$^1$H-NMR (400 MHz, CDCl$_3$): δ 2.44 (3H, s), 3.61 (2H, d, J=6.1 Hz), 4.38 (2H, d, J=6.3 Hz), 5.03 (1H, br), 6.61 (1H, br), 7.12 (2H, d, J=8.3 Hz), 7.32 (2H, d, J=8.3 Hz), 7.45 (2H, d, J=8.3 Hz), 7.73 (2H, d, J=8.3 Hz)

N-(4-Bromo-2-fluorobenzyl)-2-(toluene-4-sulfonylamino)acetamide

DR-11

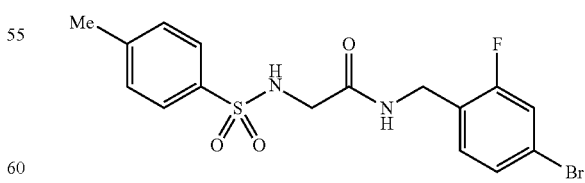

N-(4-Bromo-2-fluoro-benzyl)-2-(toluene-4-sulfonylamino)-acetamide

Yield: 64%
Melting point: 123 to 124° C.

$^1$H-NMR (400 MHz, CDCl$_3$): δ 2.42 (3H, s), 3.58 (2H, d, J=6.3 Hz), 4.40 (2H, d, J=5.9 Hz), 5.01 (1H, br), 6.60 (1H, br), 7.16 (1H, t, J=8.1 Hz), 7.22 (1H, dd, J=8.1, 1.5 Hz), 7.23-7.24 (1H, m), 7.30 (2H, d, J=8.2 Hz), 7.70 (2H, d, J=8.2 Hz)

N-(3-Bromophenyl)-2-(toluene-4-sulfonylamino)acetamide

DR-13

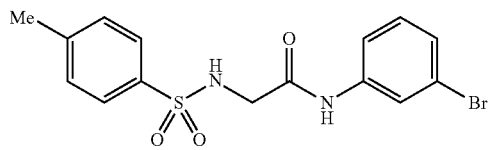 [SMILES: Cc1ccc(S(=O)(=O)NCC(=O)Nc2cccc(Br)c2)cc1]

N-(3-Bromo-phenyl)-2-(toluene-4-sulfonylamino)-acetamide

Yield: 83%
Yingyong Huaxue, 1991, 8, 48-51.

N-(4-Chlorophenyl)-2-(toluene-4-sulfonylamino)acetamide

DR-15

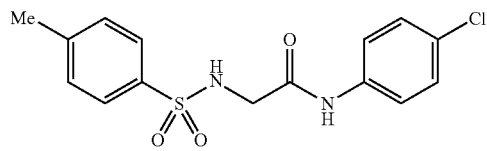 [SMILES: Cc1ccc(S(=O)(=O)NCC(=O)Nc2ccc(Cl)cc2)cc1]

N-(4-Chloro-phenyl)-2-(toluene-4-sulfonylamino)-acetamide

Yield: 24%
Indian J. Chem. Sect. B, 2002, 41B, 2635-2641.

N-(3-Bromophenyl)-2-(4-chlorobenzenesulfonylamino)acetamide

DR-22

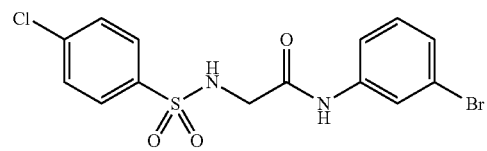 [SMILES: O=C(CNS(=O)(=O)c1ccc(Cl)cc1)Nc1cccc(Br)c1]

N-(3-Bromo-phenyl)-2-(4-chloro-benzenesulfonylamino)-acetamide

Yield: 52%
$^1$H-NMR (400 MHz, CDCl$_3$): δ 3.74 (2H, d, J=6.1 Hz), 5.22 (1H, br), 7.20 (1H, t, J=8.1 Hz), 7.26-7.30 (1H, m), 7.37 (1H, d, J=8.1 Hz), 7.54 (2H, d, J=8.5 Hz), 7.74 (1H, s), 7.84 (2H, d, J=8.5 Hz), 7.93 (1H, br)

N-(3-Bromophenyl)-2-(4-fluorobenzenesulfonylamino)acetamide

DR-23

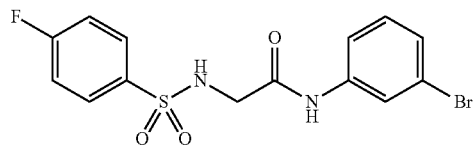 [SMILES: O=C(CNS(=O)(=O)c1ccc(F)cc1)Nc1cccc(Br)c1]

N-(3-Bromo-phenyl)-2-(4-fluoro-benzenesulfonylamino)-acetamide

Yield: 41%
$^1$H-NMR (400 MHz, CDCl$_3$): δ 3.78 (2H, d, J=6.1 Hz), 5.28 (1H, br), 7.23 (1H, t, J=8.0 Hz), 7.21-7.33 (3H, m), 7.41 (1H, d, J=8.0 Hz), 7.78 (1H, s), 7.96 (2H, dd, J=8.7, 4.8 Hz), 8.04 (1H, br)

N-(3-Bromophenyl)-2-(4-methoxybenzenesulfonylamino)acetamide

DR-24

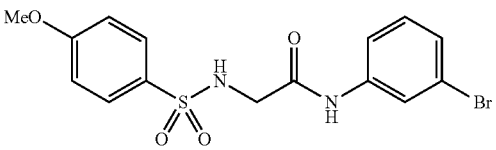 [SMILES: COc1ccc(S(=O)(=O)NCC(=O)Nc2cccc(Br)c2)cc1]

N-(3-Bromo-phenyl)-2-(4-methoxy-benzenesulfonylamino)-acetamide

Yield: 49%
$^1$H-NMR (400 MHz, CDCl$_3$): δ 3.70 (2H, d, J=6.6 Hz), 3.88 (3H, s), 5.12 (1H, br), 7.01 (2H, d, J=8.9 Hz), 7.19 (1H, t, J=8.1 Hz), 7.26-7.28 (1H, m), 7.39 (1H, d, J=8.1 Hz), 7.73 (1H, s), 7.83 (2H, d, J=8.9 Hz), 8.16 (1H, br)

N-(4-Chlorophenyl)-2-(4-methoxybenzenesulfonylamino)acetamide

DR-25

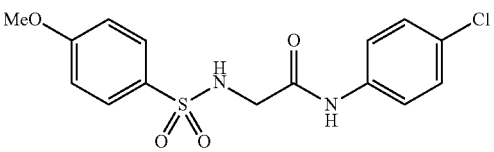 [SMILES: COc1ccc(S(=O)(=O)NCC(=O)Nc2ccc(Cl)cc2)cc1]

N-(4-Chloro-phenyl)-2-(4-methoxy-benzenesulfonylamino)-acetamide

Yield: 67%
$^1$H-NMR (400 MHz, CDCl$_3$): δ 3.70 (2H, d, J=6.6 Hz), 3.87 (3H, s), 5.14 (1H, br), 7.01 (2H, d, J=8.8 Hz), 7.29 (2H, d, J=8.9 Hz), 7.45 (2H, d, J=8.9 Hz), 7.82 (2H, d, J=8.8 Hz), 8.18 (1H, br)

N-(4-Chlorophenyl)-2-(4-fluorobenzenesulfonylamino)acetamide

DR-26

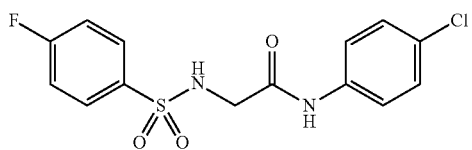 [SMILES: O=C(CNS(=O)(=O)c1ccc(F)cc1)Nc1ccc(Cl)cc1]

N-(4-Chloro-phenyl)-2-(4-fluoro-benzenesulfonylamino)-acetamide

Yield: 54%
$^1$H-NMR (400 MHz, CDCl$_3$): δ 3.74 (2H, d, J=6.3 Hz), 5.19 (1H, br), 7.22-7.32 (4H, m), 7.44 (2H, d, J=8.8 Hz), 7.92 (2H, dd, J=9.0, 4.9 Hz), 7.98 (1H, br)

N-(4-Chlorophenyl)-2-(4-chlorobenzenesulfonylamino)acetamide

DR-27

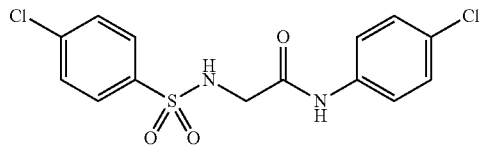 [SMILES: O=C(CNS(=O)(=O)c1ccc(Cl)cc1)Nc1ccc(Cl)cc1]

2-(4-Chloro-benzenesulfonylamino)-N-(4-chlorophenyl)-acetamide

Yield: 56%
Indian J. Exp. Biol., 1966, 4, 190-1.

N-(2-Bromophenyl)-2-(4-fluorobenzenesulfonylamino)acetamide

DR-28

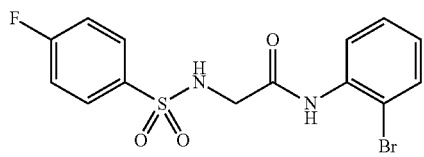 [SMILES: O=C(CNS(=O)(=O)c1ccc(F)cc1)Nc1ccccc1Br]

N-(2-Bromo-phenyl)-2-(4-fluoro-benzenesulfonylamino)-acetamide

Yield: 27%
$^1$H-NMR (400 MHz, CDCl$_3$): δ 3.83 (2H, d, J=6.1 Hz), 5.27 (1H, br), 7.02 (1H, t, J=7.9 Hz), 7.22 (2H, t, J=8.5 Hz), 7.32 (1H, t, J=7.9 Hz), 7.55 (1H, d, J=7.9 Hz), 7.94 (2H, dd, J=8.5, 5.1 Hz), 8.23 (1H, d, J=7.9 Hz), 8.37 (1H, br)

N-(2-Bromophenyl)-2-(4-chlorobenzenesulfonylamino)acetamide

DR-29

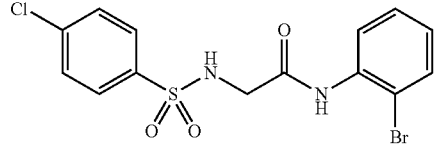 [SMILES: O=C(CNS(=O)(=O)c1ccc(Cl)cc1)Nc1ccccc1Br]

N-(2-Bromo-phenyl)-2-(4-chloro-benzenesulfonylamino)-acetamide

Yield: 29%
$^1$H-NMR (400 MHz, CDCl$_3$): δ 3.83 (2H, d, J=6.1 Hz), 5.43 (1H, br), 7.02 (1H, t, J=8.1 Hz), 7.31 (1H, t, J=8.1 Hz), 7.51 (2H, d, J=8.7 Hz), 7.54 (1H, d, J=8.1 Hz), 7.85 (2H, d, J=8.7 Hz), 8.21 (1H, d, J=8.1 Hz), 8.37 (1H, br)

Example 7

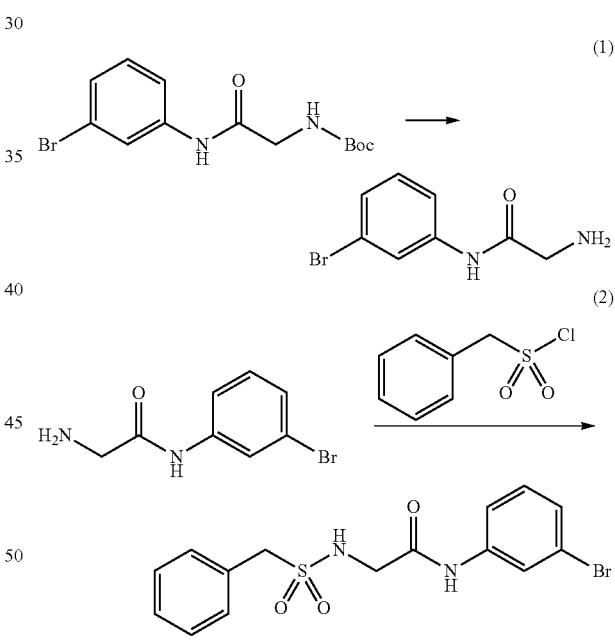

(1) Trifluoroacetic acid (1.6 mL, 22.07 mmol) was added to a methylene chloride (9 mL) solution of [(3-bromophenylcarbamoyl)methyl]carbamic acid tert-butyl ester (717 mg, 2.18 mmol) in an argon atmosphere, and the mixture was stirred at room temperature overnight.

A saturated sodium bicarbonate solution was added to the reaction mixture at 0° C. until the aqueous layer became basic.

The organic layer was extracted with methylene chloride, dried over potassium carbonate, and filtered.

The solvent was evaporated to obtain 2-amino-N-(3-bromophenyl)acetamide (colorless crystals) (421 mg, yield: 84%).

(2) Triethylamine (0.17 mL, 1.22 mmol) and DMAP (41 mg, 0.33 mmol) were added to a methylene chloride (5 mL) solution of 2-amino-N-(3-bromophenyl)acetamide (80 mg, 0.33 mmol) in an argon atmosphere. After the addition of benzylsulfamoyl chloride (69 mg, 0.36 mmol) at 0° C., the mixture was stirred at room temperature overnight.

After evaporating the solvent, the residue was purified by silica gel column chromatography (15 g, hexane:acetone=6:1 to 4:1) to obtain N-(3-bromophenyl)-2-phenylmethanesulfonylaminoacetamide (colorless crystals) (41 mg, DR-12).

Yield: 31%
Melting point: 215 to 216° C. (recrystallization solvent: toluene)
$^1$H-NMR (400 MHz, CDCl$_3$): δ 3.69 (2H, d, J=6.3 Hz), 4.38 (2H, s), 4.84 (1H, br), 7.17-7.27 (3H, m), 7.35-7.45 (5H, m), 7.75 (1H, s), 7.80 (1H, br)

Example 8

The following compounds were obtained in the same manner as in Example 7.

N-(4-Chlorophenyl)-2-phenylmethanesulfonylaminoacetamide

DR-14

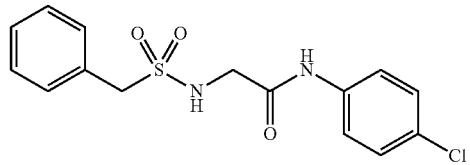 [SMILES: O=C(CNS(=O)(=O)Cc1ccccc1)Nc1ccc(Cl)cc1]

N-(4-Chloro-phenyl)-2-phenylmethanesulfonylamino-acetamide

Yield: 28%
Melting point: 200 to 201° C.
$^1$H-NMR (400 MHz, CDCl$_3$): δ 3.69 (2H, d, J=6.3 Hz), 4.38 (2H, s), 4.84 (1H, br), 7.42-7.52 (9H, m), 7.81 (1H, br)

N-(3-Chlorophenyl)-2-phenylmethanesulfonylaminoacetamide

DR-16

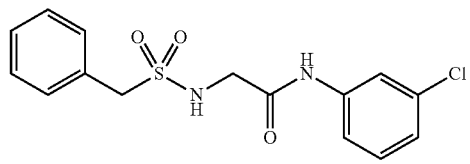 [SMILES: O=C(CNS(=O)(=O)Cc1ccccc1)Nc1cccc(Cl)c1]

N-(3-Chloro-phenyl)-2-phenylmethanesulfonylamino-acetamide

Yield: 45%
$^1$H-NMR (400 MHz, CDCl$_3$): δ 3.67 (2H, d, J=6.3 Hz), 4.36 (2H, s), 4.84 (1H, br), 7.10 (1H, d, J=7.6 Hz), 7.20-7.32 (2H, m), 7.35-7.45 (5H, m), 7.60 (1H, s), 7.81 (1H, br)

N-(3-Chlorophenyl)-2-(toluene-4-sulfonylamino)acetamide

DR-17

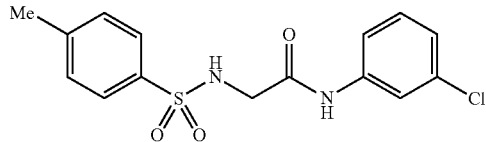 [SMILES: Cc1ccc(S(=O)(=O)NCC(=O)Nc2cccc(Cl)c2)cc1]

N-(3-Chloro-phenyl)-2-(toluene-4-sulfonylamino)-acetamide

Yield: 82%
Yingyong Huaxue, 1991, 8, 48-51.

N-(3-Nitrophenyl)-2-(toluene-4-sulfonylamino)acetamide

DR-18

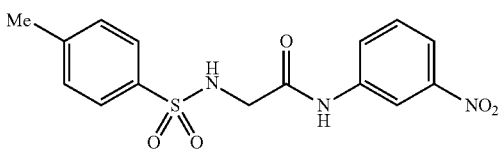 [SMILES: Cc1ccc(S(=O)(=O)NCC(=O)Nc2cccc([N+](=O)[O-])c2)cc1]

N-(3-Nitro-phenyl)-2-(toluene-4-sulfonylamino)-acetamide

Yield: 55%
Yingyong Huaxue, 1991, 8, 48-51.

N-(4-Benzyloxyphenyl)-2-(toluene-4-sulfonylamino)acetamide

DR-20

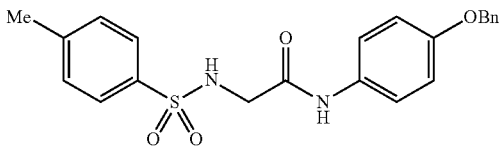 [SMILES: Cc1ccc(S(=O)(=O)NCC(=O)Nc2ccc(OCc3ccccc3)cc2)cc1]

N-(4-Benzyloxy-phenyl)-2-(toluene-4-sulfonylamino)-acetamide

Yield: 86%
$^1$H-NMR (400 MHz, CDCl$_3$): δ 2.43 (3H, s), 3.70 (2H, d, J=5.9 Hz), 5.04 (2H, s), 5.19 (1H, br), 6.93 (2H, d, J=8.8 Hz), 7.34-7.43 (9H, m), 7.77 (2H, d, J=8.1 Hz), 7.93 (1H, br)

N-(4-Fluorobenzenesulfonylamino)-N-(4-methyl-benzyl)acetamide

DR-21

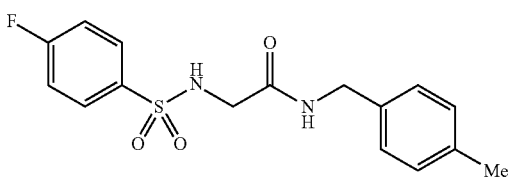 [SMILES: Cc1ccc(CNC(=O)CNS(=O)(=O)c2ccc(F)cc2)cc1]

2-(4-Fluoro-benzenesulfonylamino)-N-(4-methyl-benzyl)-acetamide

Yield: 37%
$^1$H-NMR (400 MHz, CDCl$_3$): δ 2.34 (3H, s), 3.63 (2H, s), 4.36 (2H, d, J=5.9 Hz), 6.25 (1H, br), 7.10 (2H, d, J=8.2 Hz), 7.14 (2H, d, J=8.2 Hz), 7.15-7.21 (3H, m), 7.87 (2H, dd, J=8.7, 5.0 Hz)

Example 9

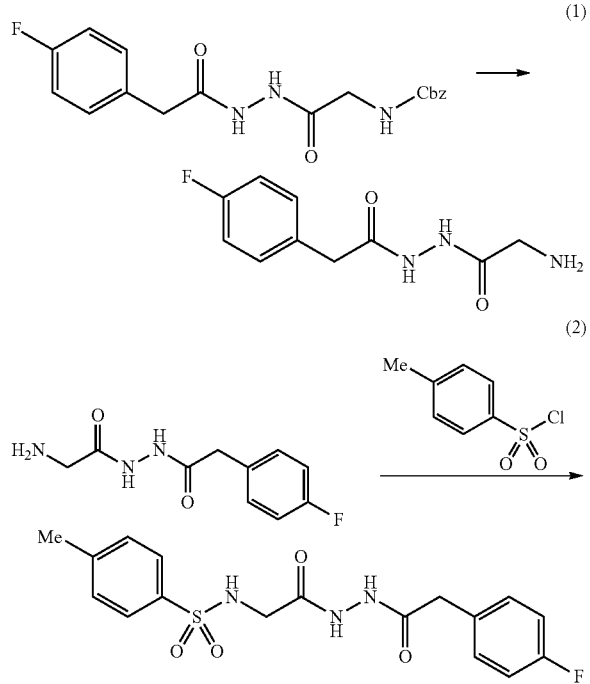

(1) Palladium hydroxide (5 mg) was added to a methanol solution (30 mL) of [N'-[2-(4-fluorophenyl)acetyl]hydrazinocarbamoylmethyl]carbamic acid butyl ester (298 mg, 0.83 mmol) in a hydrogen atmosphere, and the mixture was stirred at room temperature overnight.

After filtering the reaction mixture through celite, the solvent was evaporated to obtain 2-amino-N'-(2-(4-fluorophenyl)acetyl)acetohydrazide (colorless crystals) (233 mg, yield: 100%).

(2) Triethylamine (0.084 mL, 0.60 mmol) and DMAP (37 mg, 0.30 mmol) were added to a methylene chloride (5 mL) solution of 2-amino-N'-(2-(4-fluorophenyl)acetyl)acetohydrazide (68 mg, 0.30 mmol) in an argon atmosphere. After the addition of toluenesulfamoyl chloride (63 mg, 0.33 mmol) at 0° C., the mixture was stirred at room temperature overnight.

After evaporating the solvent, the residue was purified by silica gel column chromatography (15 g, hexane:acetone=2:1 to 1.5:1) to obtain N-(2-{N'-[2-(4-fluorophenyl)acetyl]hydrazino}-2-oxoethyl)-4-methylbenzenesulfonamide (colorless crystals) (82 mg, DR-19).

Yield: 71%
$^1$H-NMR (400 MHz, CDCl$_3$): δ 2.44 (3H, s), 3.59 (2H, s), 4.81 (2H, s), 7.05 (2H, t, J=8.7 Hz), 7.10 (1H, br), 7.10-7.26 (4H, m), 7.36 (2H, d, J=8.2 Hz), 7.72 (2H, d, J=8.2 Hz)

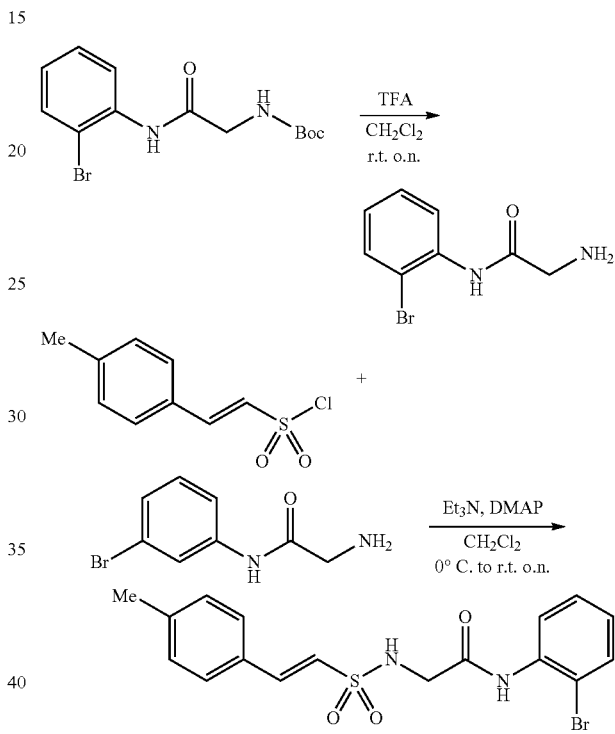

(1) Tetrahydrofuran (1.6 mL, 2.37 mmol) was added to a methylene chloride (2 mL) solution of the Boc compound (144 mg, 0.44 mmol) in an argon atmosphere, and the mixture was stirred at room temperature overnight.

A saturated sodium bicarbonate solution was added to the reaction mixture at 0° C. until the aqueous layer became basic. The organic layer was extracted with methylene chloride, dried over potassium carbonate, and filtered, and the solvent was evaporated to obtain an amine compound (98 mg, 98%) as a colorless crystalline substance.

(2) Triethylamine (0.12 mL, 0.86 mmol) was added to a methylene chloride (5 mL) solution of the amine compound (98 mg, 0.43 mmol) in an argon atmosphere. After the addition of the sulfonyl chloride compound (102 mg, 0.47 mmol) at 0° C., the mixture was stirred at room temperature overnight.

After evaporating the solvent, the residue was purified by silica gel column chromatography (15 g, hexane:acetone=8:1 to 5:1) to obtain N-(2-bromophenyl)-2-(2-tolylethanesulfonylamino)acetamide (DR-30) (colorless crystals) (75 mg, yield: 43%).

$^1$H-NMR (400 MHz, CDCl$_3$): δ 2.39 (3H, s), 3.92 (2H, d, J=6.1 Hz), 5.12 (1H, br), 6.74 (1H, d, J=15.2 Hz), 7.01 (1H, t, J=7.9 Hz), 7.21 (2H, d, J=8.2 Hz), 7.30 (1H, t, J=7.9 Hz), 7.38

(2H, d, J=8.2 Hz), 7.53 (1H, d, J=7.9 Hz), 7.54 (1H, d, J=15.2 Hz), 8.28 (1H, d, J=7.9 Hz), 8.53 (1H, br);

Melting point: 132 to 133° C.

Example 10

The following compounds were obtained in the same manner as in Example 9.

N-(4-Bromophenyl)-2-(2-tolylethanesulfonylamino)acetamide

DR-31

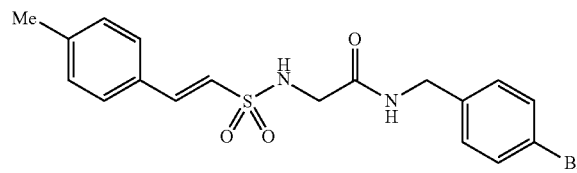

N-(4-Bromo-benzyl)-2-(2-p-tolyl-ethenesulfonylamino)-acetamide

Yield: 83%

$^1$H-NMR (400 MHz, CDCl$_3$): δ 2.41 (3H, s), 3.74 (2H, d, J=4.4 Hz), 4.39 (2H, d, J=5.9 Hz), 5.07 (1H, br), 6.58 (1H, br), 6.66 (1H, d, J=15.5 Hz), 7.09 (2H, d, J=8.1 Hz), 7.23 (2H, d, J=7.8 Hz), 7.36-7.38 (4H, m), 7.51 (1H, d, J=15.5 Hz)

Melting point: 200 to 201° C.

N-(4-Methoxyphenylphenyl)-2-(2-tolylethanesulfonylamino)acetamide

DR-32

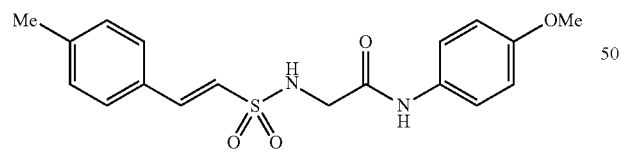

N-(4-Methoxy-phenyl)-2-(2-p-tolyl-ethenesulfonylamino)-acetamide

Yield: 35%

$^1$H-NMR (500 MHz, CDCl$_3$): δ 2.39 (3H, s), 3.79 (3H, s), 3.83 (2H, d, J=4.6 Hz), 5.14 (1H, br), 6.70 (1H, d, J=15.5 Hz), 6.85 (2H, d, J=9.2 Hz), 7.21 (2H, d, J=8.0 Hz), 7.37-7.39 (4H, m), 7.52 (1H, d, J=15.5 Hz), 7.93 (1H, br)

Melting point: 145 to 146° C.

N-(4-Bromophenyl)-2-(2-tolylethanesulfonylamino)acetamide

DR-33

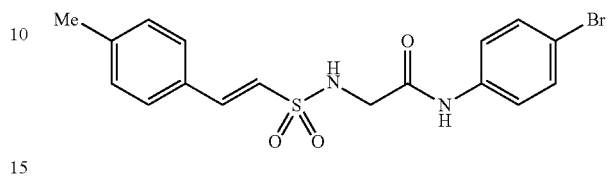

N-(4-Bromo-phenyl)-2-(2-p-tolyl-ethenesulfonylamino)-acetamide

Yield: 65%

$^1$H-NMR (500 MHz, CDCl$_3$): δ 2.39 (3H, s), 3.83 (2H, d, J=6.3 Hz), 5.22 (1H, br), 6.69 (1H, d, J=15.2 Hz), 7.21 (2H, d, J=8.0 Hz), 7.36 (2H, d, J=8.0 Hz), 7.39-7.43 (4H, m), 7.51 (1H, d, J=15.2 Hz), 8.19 (1H, br)

Melting point: 216 to 219° C.

N-(4-Bromo-2-fluorophenyl)-2-(2-tolylethanesulfonylamino)acetamide

DR-34

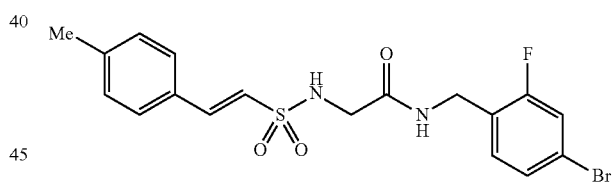

N-(4-Bromo-2-fluoro-benzyl)-2-(2-p-tolyl-ethenesulfonylamino)-acetamide

Yield: 65%

$^1$H-NMR (500 MHz, CDCl$_3$): δ 2.40 (3H, s), 3.73 (2H, d, J=6.3 Hz), 4.44 (2H, d, J=6.3 Hz), 5.01 (1H, br), 6.58 (1H, br), 6.65 (1H, d, J=15.5 Hz), 7.15-7.20 (2H, m), 7.22 (2H, d, J=8.0 Hz), 7.25-7.30 (1H, m), 7.36 (2H, d, J=8.0 Hz), 7.47 (1H, d, J=15.5 Hz);

$^{13}$C-NMR (125 MHz, DMSO-d$_6$): 21.02, 35.64 (d, J=4.8 Hz), 44.95, 118.32 (d, J=23.9 Hz), 119.99 (d, J=9.6 Hz), 125.46 (d, J=15.6 Hz), 125.64, 127.28 (d, J=3.6 Hz), 128.36, 129.54, 130.05, 130.80 (d, J=4.8 Hz), 139.20, 140.44, 159.73 (d, J=249.5 Hz), 168.53

Melting point: 161 to 162° C.

N-(4-Benzyloxyphenyl)-2-(2-tolylethanesulfony-lamino)acetamide

DR-35

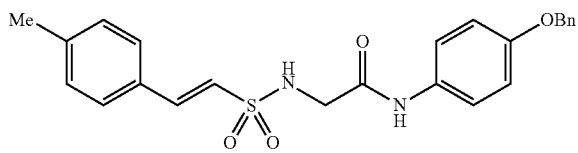 [SMILES: Cc1ccc(/C=C/S(=O)(=O)NCC(=O)Nc2ccc(OCc3ccccc3)cc2)cc1]

N-(4-Benzyloxy-phenyl)-2-(2-p-tolyl-ethenesulfony-lamino)-acetamide

Yield: 66%

$^1$H-NMR (400 MHz, CDCl$_3$): δ 2.36 (3H, s), 3.80 (2H, d, J=6.1 Hz), 5.00 (2H, s), 5.29 (1H, br), 6.68 (1H, d, J=15.4 Hz), 6.88 (2H, d, J=9.0 Hz), 7.17 (2H, d, J=7.8 Hz), 7.25-7.45 (9H, m), 7.49 (1H, d, J=15.4 Hz), 8.02 (1H, br)

$^{13}$C-NMR (125 MHz, DMSO-d$_6$): δ 20.99, 45.59, 69.33, 114.79, 120.80, 125.89, 127.64, 127.77, 128.31, 128.39, 129.51, 130.07, 131.90, 137.13, 139.05, 140.35, 154.38, 166.45

Melting point: 178 to 179° C.

Example 11

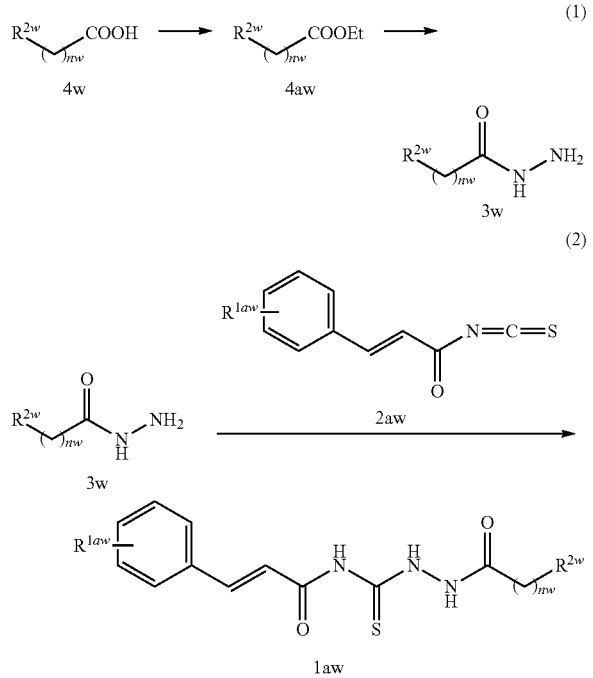

(1) Concentrated hydrochloric acid (one drop) was added to an ethanol (3 mL) solution of the carboxylic acid represented by the general formula 4w (1 mmol) in an argon atmosphere, and the mixture was refluxed with heating overnight.

After evaporating the solvent, a saturated sodium bicarbonate solution was added to the mixture until the aqueous layer became basic, followed by extraction with methylene chloride.

The organic layer was dried over sodium sulfate, and filtered, and the solvent was evaporated to obtain the ethyl ester compound represented by the general formula 4aw.

(2) Hydrazine monohydrate (0.05 mL, 1 mmol) was added to an ethanol (0.5 mL) solution of the ethyl ester compound represented by the general formula 4aw (1 mmol) in an argon atmosphere, and the mixture was refluxed with heating overnight to obtain the hydrazine compound represented by the general formula 3w.

After evaporating the solvent, a methylene chloride (5 mL) solution of the isothiocyanate compound represented by the general formula 2aw (1 mmol) was added to the mixture using a cannula, and the mixture was stirred at room temperature overnight.

The reaction mixture was filtered under suction to obtain the thiourea compound represented by the general formula 1aw.

3-(4-Chlorophenyl)-N—[N'-(2-thiophen-2-ylacetyl)hydrazinocarbothioyl]acrylamide

LW-1

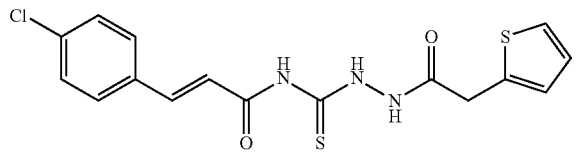 [SMILES: O=C(/C=C/c1ccc(Cl)cc1)NC(=S)NNC(=O)Cc1cccs1]

3-(4-Chloro-phenyl)-N—[N'-(2-thiophen-2-yl-acetyl)-hydrazinocarbothioyl]-acrylamide Yield: 64%

Melting point: 232 to 233° C. (recrystallization solvent: ethanol)

$^1$H-NMR (400 MHz, DMSO-d$_6$): δ 3.85 (2H, s), 6.95-7.01 (3H, m), 7.38 (1H, dd, J=5.0, 1.3 Hz), 7.53 (2H, d, J=8.5 Hz), 7.64 (2H, d, J=8.5 Hz), 7.73 (1H, d, J=15.9 Hz), 11.16 (1H, br), 11.66 (1H, br), 12.57 (1H, br)

$^{13}$C-NMR (100 MHz, DMSO-d$_6$): δ 33.90, 120.18, 125.18, 126.65, 126.67, 129.20, 129.90, 132.97, 135.26, 136.19, 143.14, 165.56, 166.26, 176.63

IR (KBr): 3211, 1684, 1655, 1630 cm$^{-1}$

MS (EI): m/z 379 (M$^+$)

[N'-(Thiophen-2-ylacetyl)hydrazinocarbothioyl]-3-(2,4,6-trichlorophenyl)acrylamide

LW-2

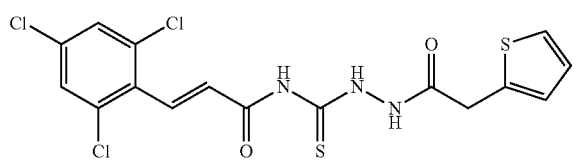 [SMILES: O=C(/C=C/c1c(Cl)cc(Cl)cc1Cl)NC(=S)NNC(=O)Cc1cccs1]

N—[N'-(2-Thiophen-2-yl-acetyl)-hydrazinocarboth-ioyl]-3-(2,4,6-trichloro-phenyl)-acrylamide Yield: 81%

Melting point: 219 to 220° C. (recrystallization solvent: hexane-acetone)

¹H-NMR (400 MHz, DMSO-d₆): δ 3.86 (2H, s), 6.95-6.98 (2H, m), 7.14 (1H, d, J=16.1 Hz), 7.38 (1H, dd, J=5.0, 1.3 Hz), 7.72 (1H, d, J=16.1 Hz), 7.81 (2H, s), 11.2 (1H, br), 11.9 (1H, br), 12.5 (1H, br)
¹³C-NMR (100 MHz, DMSO-d₆): δ 33.89, 125.18, 126.63, 126.65, 128.05, 129.00, 130.17, 134.61, 134.88, 136.16, 136.68, 164.59, 166.29, 176.44
IR (KBr): 3196, 1682, 1653, 1624 cm⁻¹
MS (EI): m/z 447 (M⁺)

3-(4-Nitrophenyl)-N—[N'-(2-thiophen-2-ylacetyl) hydrazinocarbothioyl]acrylamide

LW-3

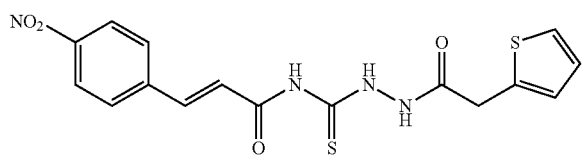 [SMILES: O=C(/C=C/c1ccc([N+](=O)[O-])cc1)NC(=S)NNC(=O)Cc1cccs1]

3-(4-Nitro-phenyl)-N—[N'-(2-thiophen-2-yl-acetyl)-hydrazinocarbothioyl]-acrylamide Yield: 60%
Melting point: 222 to 223° C. (recrystallization solvent: hexane-acetone)
¹H-NMR (400 MHz, DMSO-d₆) δ: 3.88 (2H, s), 6.97-7.00 (2H, m), 7.17 (1H, d, J=16.3 Hz), 7.40 (1H, dd, J=5.1, 1.5 Hz), 7.86 (1H, d, J=16.3 Hz), 7.89 (2H, d, J=8.9 Hz), 8.32 (2H, d, J=8.9 Hz), 11.20 (1H, br), 11.78 (1H, br), 12.56 (1H, br)
¹³C-NMR (100 MHz, DMSO-d₆) δ: 33.89, 123.72, 124.25, 125.19, 126.66, 126.67, 129.25, 136.17, 140.38, 141.79, 148.16, 165.00, 166.28, 176.46
IR (KBr): 3244, 1682, 1655, 1522, 1342 cm⁻¹
MS (EI): m/z 390 (M⁺)

N—[N'-(2-Thiophen-2-ylacetyl)hydrazinocarbothioyl]-3-p-tolylacrylamide

LW-4

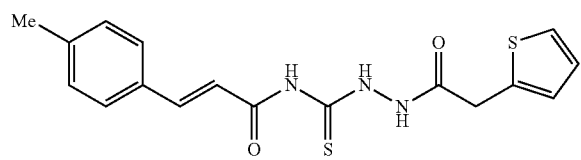 [SMILES: Cc1ccc(/C=C/C(=O)NC(=S)NNC(=O)Cc2cccs2)cc1]

N—[N'-(2-Thiophen-2-yl-acetyl)-hydrazinocarbothioyl]-3-p-tolyl-acrylamide

Yield: 77%
Melting point: 212 to 213° C. (recrystallization solvent: ethanol)
¹H-NMR (400 MHz, DMSO-d₆): δ 2.33 (3H, s), 3.85 (2H, s), 6.92-6.98 (3H, m), 7.27 (2H, d, J=7.9 Hz) 7.38 (1H, dd, J=5.1, 1.0 Hz), 7.51 (2H, d, J=7.9 Hz), 7.69 (1H, d, J=15.9 Hz), 11.14 (1H, br), 11.60 (1H, br), 12.59 (1H, br)

¹³C-NMR (100 MHz, DMSO-d₆): δ 21.09, 33.92, 118.26, 125.20, 126.66, 126.69, 128.30, 129.75, 131.32, 136.22, 140.95, 144.69, 165.96, 166.26, 176.69
IR (KBr): 3227, 1684, 1661, 1630 cm⁻¹
MS (EI): m/z 359 (M⁺)

3-(4-Fluorophenyl)-N—[N'-(2-thiophen-2-ylacetyl) hydrazinocarbothioyl]acrylamide

LW-5

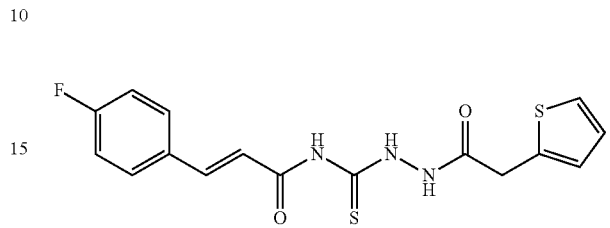

3-(4-Fluoro-phenyl)-N—[N'-(2-thiophen-2-yl-acetyl)-hydrazinocarbothiol]-acrylamide Yield: 89%
Melting point: 215 to 216° C. (recrystallization solvent: acetone)
¹H-NMR (400 MHz, DMSO-d₆): δ 3.85 (2H, s), 6.93 (1H, d, J=15.9 Hz), 6.96-6.99 (2H, m), 7.31 (2H, t, J=8.8 Hz), 7.38 (1H, dd, J=4.9, 1.5 Hz), 7.69 (2H, dd, J=8.8, 5.6 Hz), 7.74 (1H, d, J=15.9 Hz), 11.15 (1H, br), 11.64 (1H, br), 12.58 (1H, br)
¹³C-NMR (100 MHz, DMSO-d₆): δ 33.93, 116.25 (d, J=22.3 Hz), 119.25, 125.23, 126.69, 126.72, 130.63 (d, J=8.3 Hz), 130.73 (d, J=3.3 Hz), 136.22, 143.42, 163.46 (d, J=248.9 Hz), 165.73, 166.31, 176.78
IR (KBr): 3186, 1680, 1651, 1628 cm⁻¹
MS (EI): m/z 363 (M⁺)

3-(2,4-Dimethoxyphenyl)-N—[N'-(2-thiophen-2-ylacetyl)hydrazinocarbothioyl]acrylamide

LW-6

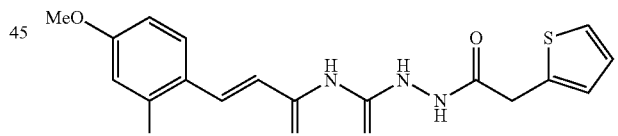

3-(2,4-Dimethoxy-phenyl)-N—[N'-(2-thiophen-2-yl-acetyl)-hydrazinocarbothioyl]-acrylamide Yield: 70%
Melting point: 207 to 208° C. (recrystallization solvent: methanol)
¹H-NMR (600 MHz DMSO-d₆) δ: 3.82 (3H, s), 3.85 (2H, s), 3.88 (3H, s), 6.62 (2H, m), 6.97 (3H, m), 7.38 (1H, dd, J=5.1, 1.5 Hz), 7.47 (1H, d, J=9.5 Hz), 7.81 (1H, d, J=15.8 Hz), 11.11 (1H, br), 11.56 (1H, br), 12.68 (1H, br)
¹³C-NMR (150 MHz, DMSO-d₆) δ: 33.89, 55.54, 55.72, 98.45, 106.33, 115.42, 116.66, 125.15, 126.61, 126.65, 130.97, 136.22, 140.07, 159.98, 163.05, 166.19, 166.80, 176.94
IR (KBr): 3225, 1670, 1606, 1531, 1215, 1132.1 cm⁻¹
MS (EI): m/z 405 (M⁺)

3-(3,5-Dibromophenyl)-N—[N'-(2-thiophen-2-ylacetyl)hydrazinocarbothioyl]acrylamide

LW-7

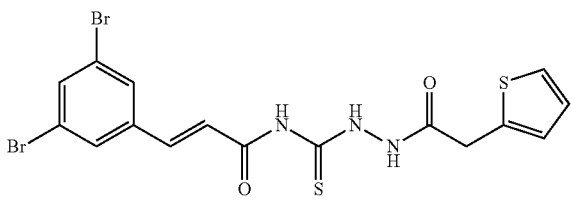 [SMILES: O=C(/C=C/c1cc(Br)cc(Br)c1)NC(=S)NNC(=O)Cc1cccs1]

3-(3,5-Dibromo-phenyl)-N—[N'-(2-thiophen-2-yl-acetyl)-hydrazinocarbothioyl]-acrylamide Yield: 81%

Melting point: 212 to 213° C. (recrystallization solvent: hexane-acetone)

$^1$H-NMR (400 MHz, DMSO-d$_6$): δ 3.85 (2H, s), 6.95-6.98 (2H, s), 7.06 (1H, d, J=15.9 Hz), 7.38 (1H, dd, J=4.9, 1.5 Hz), 7.67 (1H, d, J=15.9 Hz), 7.84 (2H, d, J=1.5 Hz), 7.92 (1H, d, J=1.5 Hz), 11.17 (1H, br), 11.59 (1H, br), 12.48 (1H, br)

$^{13}$C-NMR (100 MHz, DMSO-d$_6$) δ: 33.91, 122.77, 123.13, 125.22, 126.70, 129.69, 129.80, 134.89, 136.19, 138.31, 141.07, 165.00, 166.34, 176.59

IR (KBr): 3184, 1686, 1663, 1632 cm$^{-1}$

MS (EI): m/z 501 (M$^+$)

3-(4-Isopropylphenyl)-N—[N'-(2-thiophen-2-ylacetyl)hydrazinocarbothioyl]acrylamide

LW-8

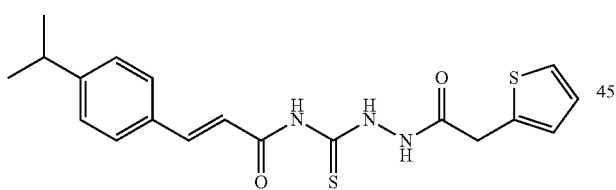

3-(4-Isopropyl-phenyl)-N—[N'-(2-thiophen-2-yl-acetyl)-hydrazinocarbothioyl]-acrylamide Yield: 50%

Melting point: 201 to 202° C. (recrystallization solvent: ethyl acetate)

$^1$H-NMR (400 MHz, DMSO-d$_6$): δ1.20 (6H, d, J=6.8 Hz), 2.91 (1H, sept, J=6.8 Hz), 3.85 (2H, s), 6.93-6.98 (3H, m), 7.34 (2H, d, J=8.1 Hz), 7.38 (1H, dd, J=5.0, 1.3 Hz), 7.54 (2H, d, J=8.1 Hz), 7.70 (1H, d, J=15.9 Hz), 11.14 (1H, br), 11.62 (1H, br), 12.59 (1H, br)

$^{13}$C-NMR (100 MHz, DMSO-d$_6$): δ 23.56, 33.40, 33.89, 118.37, 125.18, 126.64, 126.67, 127.12, 128.40, 131.73, 136.20, 144.63, 151.64, 165.92, 166.24, 176.78

MS (EI): m/z 387 (M$^+$)

3-Biphenyl-4-yl-N—[N'-(2-thiophen-2-ylacetyl)hydrazinocarbothioyl]acrylamide

LW-9

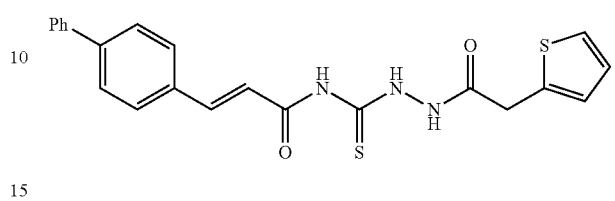

3-Biphenyl-4-yl-N—[N'-(2-thiophen-2-yl-acetyl)-hydrazinocarbothioyl]-acrylamide

Yield: 85%

Melting point: 231 to 232° C.

$^1$H-NMR (400 MHz, DMSO-d$_6$): δ 3.86 (2H, s), 6.96-6.99 (2H, m), 7.04 (1H, d, J=15.9 Hz), 7.38-7.41 (2H, m), 7.48 (2H, t, J=7.6 Hz), 7.70-7.80 (7H, m), 11.16 (1H, br), 11.66 (1H, br), 12.61 (1H, br)

$^{13}$C-NMR (100 MHz, DMSO-d$_6$): δ 33.91, 119.26, 125.19, 126.68, 126.72, 127.30, 128.08, 128.94, 129.05, 131.31, 133.13, 136.21, 139.07, 142.26, 144.13, 165.79, 166.27, 176.74

MS (EI): m/z 421 (M$^+$)

3-(2,6-Dimethoxyphenyl)-N—[N'-(2-thiophen-2-ylacetyl)hydrazinocarbothioyl]acrylamide

LW-10

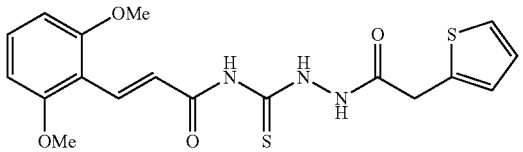 [SMILES: COc1cccc(OC)c1/C=C/C(=O)NC(=S)NNC(=O)Cc1cccs1]

3-(2,6-Dimethoxy-phenyl)-N—[N'-(2-thiophen-2-yl-acetyl)-hydrazinocarbothioyl]-acrylamide Yield: 59%

Melting point: 220 to 221° C. (recrystallization solvent: hexane-acetone)

$^1$H-NMR (400 MHz, DMSO-d$_6$): δ 3.87 (8H, s), 6.71 (2H, d, J=8.3 Hz), 6.96-6.98 (2H, m), 7.34-7.38 (3H, m), 8.06 (1H, d, J=15.9 Hz), 11.12 (1H, br), 11.67 (1H, br), 12.73 (1H, br)

$^{13}$C-NMR (100 MHz, DMSO-d$_6$): δ 33.90, 55.92, 104.07, 110.99, 120.95, 125.18, 126.62, 126.67, 132.55, 135.32, 136.23, 159.82, 166.17, 167.53, 176.86;

IR (KBr): 3219, 1670, 1653, 1611 cm$^{-1}$

MS (EI): m/z 405 (M$^+$)

N—[N'-(2-Thiophen-2-ylacetyl)hydrazinocarbothioyl]-3-(2,4,6-trifluorophenyl)acrylamide

LW-11

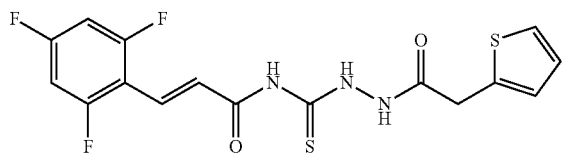 [SMILES: O=C(/C=C/c1c(F)cc(F)cc1F)NC(=S)NNC(=O)Cc1cccs1]

N—[N'-(2-Thiophen-2-yl-acetyl)-hydrazinocarbothioyl]-3-(2,4,6-trifluoro-phenyl)-acrylamide Yield: 69%

Melting point: 207 to 208° C.

$^1$H-NMR (400 MHz, DMSO-$d_6$): δ 3.85 (2H, s), 6.96-6.98 (2H, m), 7.20 (1H, d, J=16.0 Hz), 7.36-7.40 (3H, m), 7.60 (1H, d, J=16.0 Hz), 11.17 (1H, br), 11.87 (1H, br), 12.57 (1H, br)

$^{13}$C-NMR (100 MHz, DMSO-$d_6$): δ 33.90, 101.73 (td, J=26.9, 2.5 Hz), 108.66 (td, J=15.3, 5.0 Hz), 124.64 (td, J=8.4, 3.0 Hz), 125.19, 126.65, 126.68, 129.11, 136.19, 161.35 (dt, J=254.7, 7.9 Hz), 161.42 (dt, J=254.7, 8.1 Hz), 165.39, 166.27, 176.44

IR (KBr): 3190, 1684, 1653, 1624 cm$^{-1}$

MS (EI): m/z 399 (M$^+$)

3-(4-Fluorophenyl)-N—[N'-phenylacetylhydrazinocarbothioyl]acrylamide

LW-12

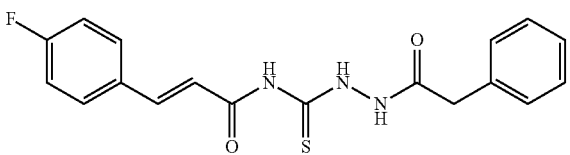 [SMILES: O=C(/C=C/c1ccc(F)cc1)NC(=S)NNC(=O)Cc1ccccc1]

3-(4-Fluoro-phenyl)-N—(N'-phenylacetyl-hydrazinocarbothioyl)-acrylamide

Yield: 89%

Melting point: 212 to 213° C.

$^1$H-NMR (400 MHz, DMSO-$d_6$) δ: 3.62 (2H, s), 6.93 (1H, d, J=15.7 Hz), 7.25-7.32 (7H, m), 7.69 (2H, dd, J=8.8, 5.6 Hz), 7.73 (1H, d, J=15.7 Hz), 11.10 (1H, s), 11.62 (1H, s), 12.56 (1H, s)

$^{13}$C-NMR (100 MHz, DMSO-$d_6$) δ: 39.57, 116.20 (d, J=21.5 Hz), 119.25, 126.61, 128.25, 129.20, 130.57 (d, J=9.1 Hz), 130.71 (d, J=3.3 Hz), 135.26, 143.33, 163.41 (d, J=248.9 Hz), 165.66, 167.29, 176.77

MS (EI): m/z 357 (M$^+$)

N—[N'-(2-Thiophen-2-ylacetyl)hydrazinocarbothioyl]-3-(4-trifluoromethylphenyl)acrylamide

LW-13

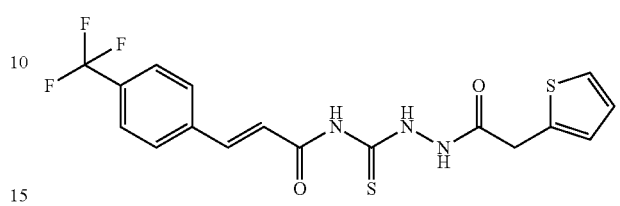

N—[N'-(2-Thiophen-2-yl-acetyl)-hycirazinocarbothioyl]-3-(4-trifluoromethyl-phenyl)-acrylamide Yield: 83%

Melting point: 224 to 225° C.

$^1$H-NMR (400 MHz, DMSO-$d_6$): δ 3.86 (2H, s), 6.95-6.99 (2H, m), 7.11 (1H, d, J=15.9 Hz), 7.38 (1H, dd, J=4.9, 1.5 Hz), 7.76-7.83 (5H, m), 11.17 (1H, br), 11.72 (1H, br), 12.53 (1H, br)

$^{13}$C-NMR (100 MHz, DMSO-$d_6$): δ 33.93, 122.34, 124.00 (q, J=272.4 Hz), 125.22, 126.02 (q, J=4.1 Hz), 126.70, 127.83, 128.86, 130.24 (q, J=32.0 Hz), 136.19, 138.03 (q, J=1.7 Hz), 142.66, 165.28, 166.34, 176.62

IR (KBr): 1636, 1661, 1684, 3196 cm$^{-1}$

MS (EI): m/z 413 (M$^+$)

N—(N'-Phenylacetylhydrazinocarbothioyl)-3-(2,4,6-trifluorophenyl)acrylamide

LW-14

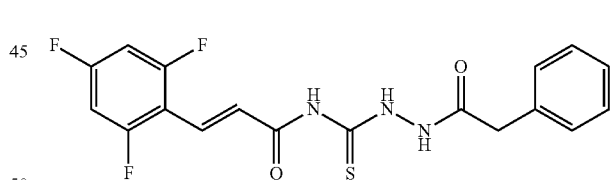

N—(N'-Phenylacetyl-hydrazinocarbothioyl)-3-(2,4,6-trifluoro-phenyl)-acrylamide

Yield: 75%

Melting point: 210 to 211° C.

$^1$H-NMR (400 MHz, DMSO-$d_6$) δ: 3.62 (2H, s), 7.19 (1H, d, J=16.1 Hz), 7.23-7.40 (7H, m), 7.59 (1H, d, J=16.1 Hz), 11.13 (1H, br), 11.86 (1H, br), 12.53 (1H, br)

$^{13}$C-NMR (100 MHz, DMSO-$d_6$) δ: 39.54, 101.72 (td, J=27.3, 3.3 Hz), 108.64 (td, J=16.1, 4.1 Hz), 124.67, 126.60, 128.25, 129.07, 129.18, 135.25, 160.01 (dd, J=12.8, 9.9 Hz), 162.63 (dd, J=12.8, 9.9 Hz), 165.35, 167.28, 176.47

MS (EI): m/z 393 (M$^+$)

3-(3,5-Dibromophenyl)-N—[N'-phenylacetylhydrazinocarbothioyl]acrylamide

LW-15

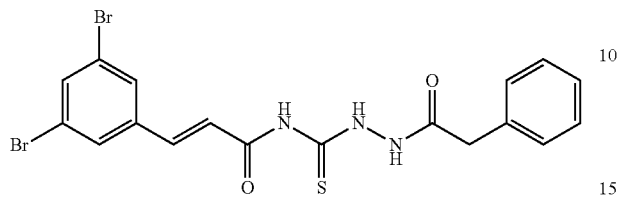

3-(3,5-Dibromo-phenyl)-N—(N-phenylacetyl-hydrazinocarbothioyl)-acrylamide

Yield: 70%

Melting point: 192 to 193° C.

$^1$H-NMR (400 MHz, DMSO-$d_6$) δ: 3.62 (2H, s), 7.06 (1H, d, J=15.9 Hz), 7.23-7.32 (5H, m), 7.66 (1H, d, J=15.9 Hz), 7.84 (2H, s), 7.92 (1H, s), 11.13 (1H, br), 11.57 (1H, br), 12.47 (1H, br)

$^{13}$C-NMR (100 MHz, DMSO-$d_6$) δ: 39.59, 122.79, 123.12, 126.66, 128.30, 129.24, 129.80, 134.88, 135.26, 138.32, 141.06, 164.99, 167.42, 176.69

MS (EI): m/z 495 (M$^+$)

3-(4-Fluorophenyl)-N—[N'-(2-thiophene-2-carbonyl)hydrazinocarbothioyl]acrylamide

LW-16

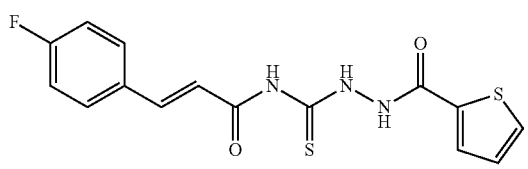 [SMILES: O=C(/C=C/c1ccc(F)cc1)NC(=S)NNC(=O)c1cccs1]

3-(4-Fluoro-phenyl)-N—[N'-(thiophene-2-carbonyl)-hydrazinocarbothioyl]-acrylamide Yield: 85%

Melting point: 217 to 218° C.

$^1$H-NMR (400 MHz, DMSO-$d_6$) δ: 6.98 (1H, d, J=15.7 Hz), 7.21 (1H, t, J=4.5 Hz), 7.32 (2H, t, J=8.7 Hz), 7.69-7.72 (2H, m), 7.77 (1H, d, J=15.7 Hz), 7.87 (1H, d, J=4.5 Hz), 7.90 (1H, d, J=4.5 Hz), 11.10 (1H, br), 11.67 (1H, br), 12.14 (1H, br)

$^{13}$C-NMR (100 MHz, DMSO-$d_6$) δ: 116.24 (d, J=22.3 Hz), 119.41, 128.21, 129.60, 130.63 (d, J=9.1 Hz), 130.76 (d, J=3.3 Hz), 132.00, 136.63, 143.47, 159.48, 163.45 (d, J=248.9 Hz), 165.44, 177.93

MS (EI): m/z 349 (M$^+$)

3-(2,6-Dimethoxyphenyl)-N—[N'-phenylacetylhydrazinocarbothioyl]acrylamide

LW-17

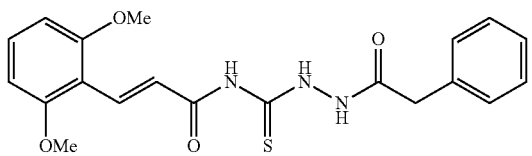 [SMILES: COc1cccc(OC)c1/C=C/C(=O)NC(=S)NNC(=O)Cc1ccccc1]

3-(2,6-Dimethoxy-phenyl)-N—(N-phenylacetyl-hydrazinocarbothioyl)-acrylamide

Yield: 73%

Melting point: 211 to 212° C.

$^1$H-NMR (400 MHz, DMSO-$d_6$) δ: 3.62 (2H, s), 3.89 (6H, s), 6.71 (2H, d, J=8.3 Hz), 7.25-7.39 (7H, m), 8.05 (1H, d, J=15.9 Hz), 11.07 (1H, s), 11.65 (1H, s), 12.70 (1H, br)

$^{13}$C-NMR (100 MHz, DMSO-$d_6$) δ: 39.59, 55.94, 104.09, 111.02, 121.00, 126.63, 128.29, 129.21, 132.57, 135.19, 135.31, 159.84, 167.26, 167.53, 177.00

MS (EI): m/z 399 (M$^+$)

3-(2,6-Dimethoxyphenyl)-N—[N'-(2-thiophene-2-carbonyl)hydrazinocarbothioyl]acrylamide

LW-19

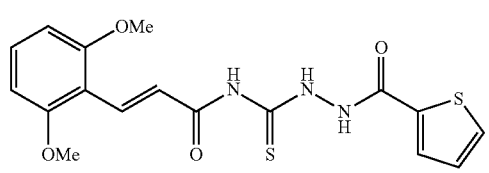 [SMILES: COc1cccc(OC)c1/C=C/C(=O)NC(=S)NNC(=O)c1cccs1]

3-(2,6-Dimethoxy-phenyl)-N—[N'-(thiophene-2-carbonyl)-hydrazinocarbothioyl]-acrylamide Yield: 26%

Melting point: 209 to 210° C.

$^1$H-NMR (400 MHz, DMSO-$d_6$): δ 3.88 (6H, s), 6.72 (2H, d, J=8.5 Hz), 7.21 (1H, t, J=5.1 Hz), 7.37-7.42 (2H, m), 7.84-7.90 (2H, m), 8.09 (1H, d, J=15.9 Hz), 11.07 (1H, br), 11.68 (1H, br), 12.14 (1H, br)

MS (EI): m/z 391 (M$^+$)

3-(3,5-Dibromophenyl)-N—[N'-(2-thiophene-2-carbonyl)hydrazinocarbothioyl]acrylamide

LW-20

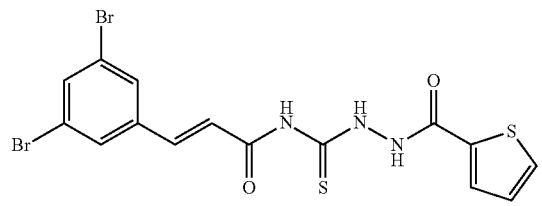 [SMILES: O=C(/C=C/c1cc(Br)cc(Br)c1)NC(=S)NNC(=O)c1cccs1]

3-(3,5-Dibromo-phenyl)-N—[N'-(thiophene-2-carbonyl)-hydrazinocarbothioyl]-acrylamide Yield: 59%

Melting point: 217 to 218° C.

$^{1}$H-NMR (400 MHz, DMSO-d$_{6}$) δ: 7.11 (1H, d, J=15.6 Hz), 7.21 (1H, t, J=4.3 Hz), 7.70 (1H, d, J=15.6 Hz), 7.86-7.93 (5H, m), 11.11 (1H, br), 11.62 (1H, br), 12.06 (1H, br);

$^{13}$C-NMR (100 MHz, DMSO-d$_{6}$) δ: 122.90, 123.11, 128.20, 129.62, 129.80, 132.022, 134.88, 136.59, 138.33, 141.16, 159.51, 164.73, 181.07

MS (EI): m/z 487 (M$^{+}$)

3-(3,5-Dibromophenyl)-N—[N'-[2-(4-fluorophenyl)acetyl]hydrazinocarbothioyl]acrylamide

LW-21

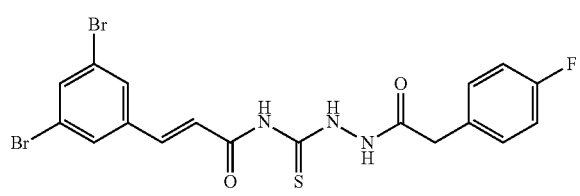 [SMILES: O=C(/C=C/c1cc(Br)cc(Br)c1)NC(=S)NNC(=O)Cc1ccc(F)cc1]

3-(3,5-Dibromo-phenyl)-N-{N'-[2-(4-fluoro-phenyl)-acetyl]hydrazinocarbothioyl}-acrylamide Yield: 28%

Melting point: 195 to 196° C.

$^{1}$H-NMR (400 MHz, DMSO-d$_{6}$) δ: 3.61 (2H, s), 7.06 (1H, d, J=16.0 Hz), 7.11-7.35 (4H, m), 7.66 (1H, d, J=16.0 Hz), 7.84 (2H, s), 7.92 (1H, s), 11.11 (1H, br), 11.56 (1H, br), 12.44 (1H, br)

$^{13}$C-NMR (100 MHz, DMSO-d$_{6}$) δ: 30.88, 115.05 (d, J=21.5 Hz), 122.79, 123.16 (d, J=2.5 Hz), 128.35, 129.28, 129.78, 129.86, 131.11, 134.98 (d, J=8.3 Hz), 139.75 (d, J=282.9 Hz), 151.38, 176.13, 180.47

MS (EI): m/z 515 (M$^{+}$)

N—(N'-Benzoylhydrazinocarbothioyl)-3-(3,5-dibromophenyl)acrylamide

LW-23

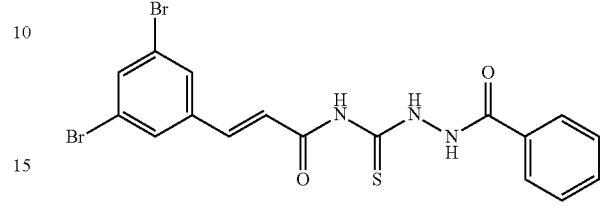

N—(N'-Benzoyl-hydrazinocarbothioyl)-3-(3,5-dibromo-phenyl)-acrylamide

Yield: 44%

Melting point: 224 to 225° C.

$^{1}$H-NMR (400 MHz, DMSO-d$_{6}$) δ: 7.11 (1H, d, J=15.7 Hz), 7.52 (2H, t, J=7.4 Hz), 7.60 (1H, t, J=7.4 Hz), 7.71 (1H, d, J=15.7 Hz), 7.87 (2H, s), 7.90 (2H, d, J=7.4 Hz), 7.93 (1H, s), 11.10 (1H, br), 11.63 (1H, br), 12.18 (1H, br)

$^{13}$C-NMR (100 MHz, DMSO-d$_{6}$) δ: 122.89, 123.12, 127.65, 128.51, 129.80, 132.02, 132.10, 134.88, 138.33, 141.13, 164.56, 164.83, 180.46

3-(3,5-Dibromophenyl)-N—[N'-(2-m-tolylacetyl)hydrazinocarbothioyl]acrylamide

LW-24

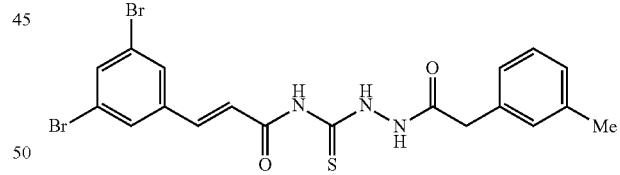

3-(3,5-Dibromo-phenyl)-N—[N'-(2-m-tolyl-acetyl)-hydrazinocarbothioyl]-acrylamide Yield: 76%

Melting point: 203 to 204° C.

$^{1}$H-NMR (400 MHz, DMSO-d$_{6}$) δ: 2.28 (3H, s), 3.57 (2H, s), 7.04-7.20 (5H, m), 7.66 (1H, d, J=15.9 Hz), 7.84 (2H, s), 7.91 (1H, s), 11.10 (1H, br), 11.55 (1H, br), 12.48 (1H, br)

$^{13}$C-NMR (100 MHz, DMSO-d$_{6}$) δ: 20.97, 122.78, 123.12, 126.29, 127.26, 128.18, 129.79, 129.84, 134.88, 135.11, 137.31, 138.31, 141.04, 164.97, 167.40, 176.58

3-(3,5-Dibromophenyl)-N—[N'-[2-(3-methoxyphenylacetyl)hydrazinocarbothioyl]acrylamide

LW-26

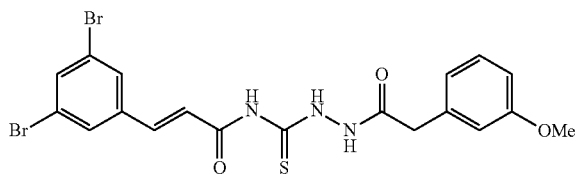 [SMILES: COc1cccc(CC(=O)NNC(=S)NC(=O)/C=C/c2cc(Br)cc(Br)c2)c1]

3-(3,5-Dibromo-phenyl)-N-{N'-[2-(3-methoxy-phenyl)-acetyl]-hydrazinocarbothioyl}-acrylamide Yield: 69%

Melting point: 202 to 203° C.

$^1$H-NMR (400 MHz, DMSO-$d_6$) δ: 3.58 (2H, s), 3.74 (3H, s), 6.81 (1H, d, J=7.9 Hz), 6.89 (1H, d, J=7.9 Hz), 6.92 (1H, s), 7.06 (1H, d, J=16.0 Hz), 7.21 (1H, t, J=7.9 Hz), 7.67 (1H, d, J=16.0 Hz), 7.83-7.84 (2H, m), 7.92 (1H, s), 11.10 (1H, br), 11.56 (1H, br), 12.45 (1H, br)

$^{13}$C-NMR (100 MHz, DMSO-$d_6$) δ: 39.63, 54.98, 112.17, 114.82, 121.48, 122.78, 123.11, 129.27, 129.78, 134.87, 136.69, 138.30, 141.02, 159.16, 164.95, 167.23, 176.72

3-(3,5-Dibromophenyl)-N—[N'-(3-phenylpropionyl)hydrazinocarbothioyl]acrylamide

LW-31

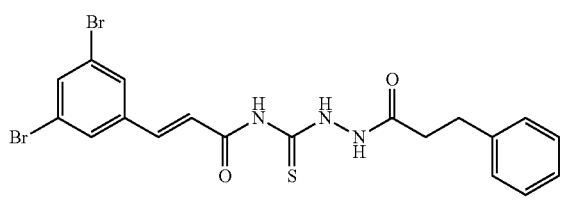 [SMILES: O=C(/C=C/c1cc(Br)cc(Br)c1)NC(=S)NNC(=O)CCc1ccccc1]

3-(3,5-Dibromo-phenyl)-N—[N'-(3-phenyl-propionyl)-hydrazinocarbothioyl]acrylamide Yield: 23%

Melting point: 213 to 214° C.

$^1$H-NMR (400 MHz, DMSO-$d_6$) δ: 2.57 (2H, t, J=7.8 Hz), 2.87 (2H, t, J=7.8 Hz), 7.06 (1H, d, J=16.0 Hz), 7.18-7.28 (5H, m), 7.67 (1H, d, J=16.0 Hz), 7.84 (2H, d, J=1.5 Hz), 7.92 (1H, t, J=1.5 Hz), 10.98 (1H, br), 11.54 (1H, br), 12.47 (1H, br)

$^{13}$C-NMR (100 MHz; DMSO-$d_6$) δ: 30.57, 34.46, 122.80, 123.10, 125.99, 128.22, 128.30, 129.76, 132.25, 138.30, 140.80, 154.67, 168.68, 176.29, 180.24

MS (EI): m/z 511 (M$^+$)

Example 12

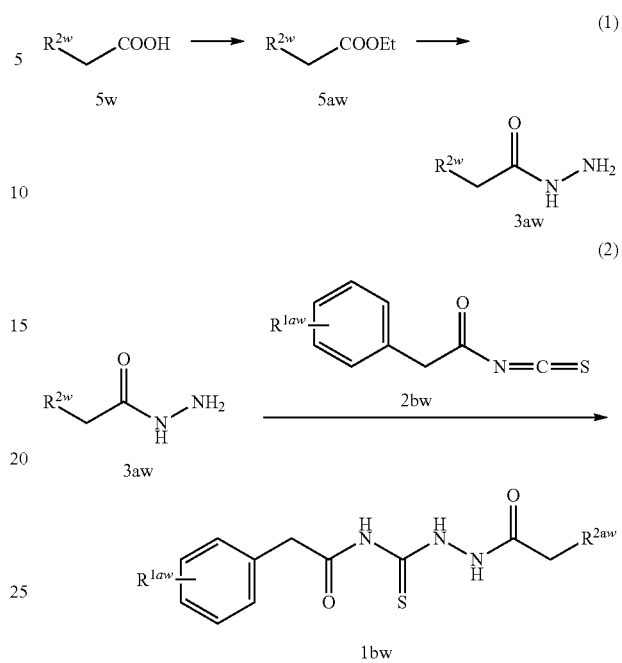

(1) Concentrated hydrochloric acid (one drop) was added to an ethanol (3 mL) solution of the carboxylic acid represented by the general formula 5w (1 mmol) in an argon atmosphere, and the mixture was refluxed with heating overnight.

After evaporating the solvent, a saturated sodium bicarbonate solution was added to the mixture until the aqueous layer became basic, followed by extraction with methylene chloride.

The organic layer was dried over sodium sulfate, and filtered, and the solvent was evaporated to obtain the ethyl ester compound represented by the general formula 5aw.

(2) Hydrazine monohydrate (0.05 mL, 1 mmol) was added to an ethanol (0.5 mL) solution of the ethyl ester compound represented by the general formula 4aw (1 mmol) in an argon atmosphere, and the mixture was refluxed with heating overnight to obtain the hydrazine compound represented by the general formula 3aw.

After evaporating the solvent, a methylene chloride (5 mL) solution of the isothiocyanate compound represented by the general formula 2bw (1 mmol) was added to the mixture using a cannula, and the mixture was stirred at room temperature overnight.

The reaction mixture was filtered under suction to obtain the thiourea compound represented by the general formula 1bw.

2-Phenyl-N—[N'-(2-thiophen-2-ylacetyl)hydrazinocarbothioyl]acetamide

LW-18

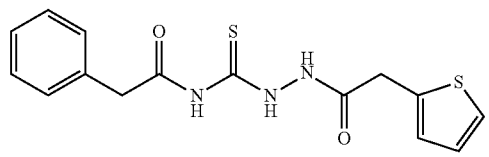 [SMILES: O=C(Cc1cccs1)NNC(=S)NC(=O)Cc1ccccc1]

2-Phenyl-N—[N'-(2-thiophen-2-yl-acetyl)-hydrazinocarbothioyl]-acetamide

Yield: 63%

Melting point: 161 to 162° C.

¹H-NMR (400 MHz, DMSO-d₆) δ: 3.74 (2H, s), 3.81 (2H, s), 6.93-6.95 (2H, m), 7.24-7.37 (6H, m), 11.06 (1H, br), 11.73 (1H, br), 12.30 (1H, br)

¹³C-NMR (100 MHz, DMSO-d₆) δ: 33.94, 42.11, 125.24, 126.70, 126.74, 127.08, 128.32, 128.51, 129.41, 134.30, 166.39, 167.43, 176.90

MS (EI): m/z 333 (M⁺)

N—[N'-(2-(4-Fluorophenyl)acetyl)hydrazinocarbothioyl]-2-phenylacetamide

LW-22

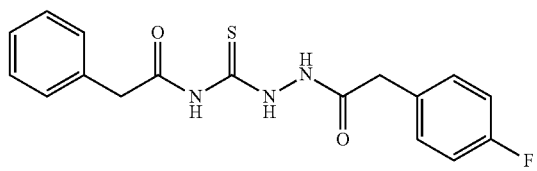 [SMILES: O=C(Cc1ccc(F)cc1)NNC(=S)NC(=O)Cc1ccccc1]

N-{N'-[2-(4-Fluoro-phenyl)-acetyl]-hydrazinocarbothioyl}-2-phenyl-acetamide

Yield: 55%

Melting point: 182 to 183° C.

¹H-NMR (400 MHz, DMSO-d₆) δ: 3.57 (2H, s), 3.74 (2H, s), 7.11 (2H, t, J=8.7H), 7.20-7.40 (7H, m), 10.10 (1H, br), 11.02 (1H, br), 11.73 (1H, br)

¹³C-NMR (100 MHz, DMSO-d₆) δ: 38.64, 42.07, 114.85 (d, J=21.5 Hz), 126.51, 127.01, 128.23, 128.45, 129.04, 129.37, 131.06 (d, J=8.3 Hz), 131.43 (d, J=2.5 Hz), 135.01 (d, J=286.9 Hz), 167.33, 172.57, 177.11

2-Phenyl-N—[N'-(2-m-tolylacetyl)hydrazinocarbothioyl]acetamide

LW-25

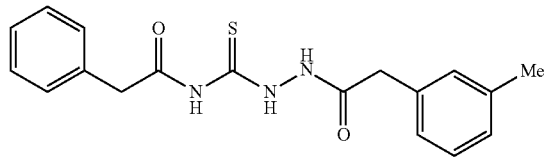 [SMILES: Cc1cccc(CC(=O)NNC(=S)NC(=O)Cc2ccccc2)c1]

2-Phenyl-N—[N'-(2-m-tolyl-acetyl)-hydrazinocarbothioyl]-acetamide

Yield: 24%

Melting point: 149 to 150° C.

¹H-NMR (400 MHz, DMSO-d₆) δ: 2.26 (3H, s), 3.53 (2H, s), 3.74 (2H, s), 7.09-7.29 (9H, m), 11.01 (1H, br), 11.72 (1H, br), 12.28 (1H, br)

2-Phenyl-N—(N'-phenylacetylhydrazinocarbothioyl)acetamide

LW-27

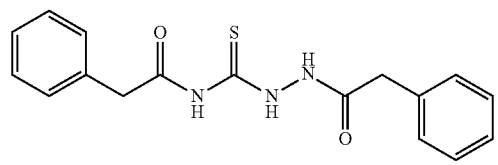 [SMILES: O=C(Cc1ccccc1)NNC(=S)NC(=O)Cc1ccccc1]

2-Phenyl-N—(N'-phenylacetyl-hydrazinocarbothioyl)-acetamide

Yield: 34%

N—[N'-[2-(2,6-difluorophenyl)acetyl]hydrazinocarbothioyl]-2-phenylacetamide

LW-28

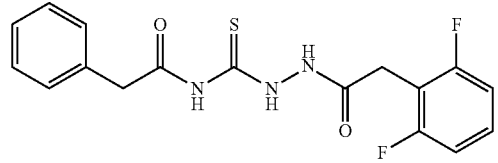 [SMILES: O=C(Cc1c(F)cccc1F)NNC(=S)NC(=O)Cc1ccccc1]

N-{N'-[2-(2,6-Difluoro-phenyl)-acetyl]-hydrazinocarbothioyl}-2-phenyl-acetamide

Yield: 88%

Melting point: 174 to 175° C.

¹H-NMR (400 MHz, DMSO-d₆) δ: 3.67 (2H, s), 3.74 (2H, s), 7.07 (2H, t, J=7.4 Hz), 7.22-7.40 (6H, m), 11.07 (1H, br), 11.73 (1H, br), 12.23 (1H, br)

N—[N'-[2-(3,5-difluorophenyl)acetyl]hydrazinocarbothioyl]-2-phenylacetamide

LW-29

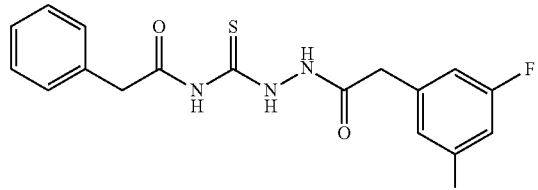

N-{N'-[2-(3,5-Difluoro-phenyl)-acetyl]-hydrazinocarbothioyl}-2-phenyl-acetamide

Yield: 4%

Melting point: 178 to 179° C.

¹H-NMR (400 MHz, DMSO-d₆) δ: 3.74 (2H, s), 4.03 (2H, s), 7.03-7.12 (3H, m), 7.23-7.34 (5H, m), 11.02 (1H, br), 11.74 (1H, br), 12.18 (1H, br)

¹³C-NMR (100 MHz, DMSO-d₆) δ: 26.73, 42.06, 110.77 (d, J=20.7 Hz), 111.26 (d, J=25.6 Hz), 127.00, 128.44, 129.35, 134.29, 159.86 (d, J=8.3 Hz), 162.31 (d, J=6.3 Hz), 165.60, 172.53, 177.32

2-Phenyl-N—[N'-(3-phenylisopropionyl)hydrazinocarbothioyl]acetamide

LW-30

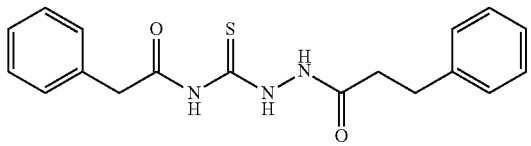 [SMILES: O=C(CCc1ccccc1)NNC(=S)NC(=O)Cc1ccccc1]

2-Phenyl-N—[N'-(3-phenyl-propionyl)-hydrazinocarbothioyl]-acetamide

Yield: 41%

Melting point: 88 to 90° C.

$^1$H-NMR (400 MHz, DMSO-d$_6$) δ: 2.52 (2H, m), 2.83 (2H, m), 3.74 (2H, s), 7.16-7.30 (10H, m), 10.80 (1H, br), 11.70 (1H, br), 12.28 (1H, br)

MS (EI): m/z 341 (M$^+$)

2-(4-Fluorophenyl)-N-{N'-[2-(4-fluoro-phenyl)-acetyl]-hydrazinocarbothioyl}-acetamide

LW-32

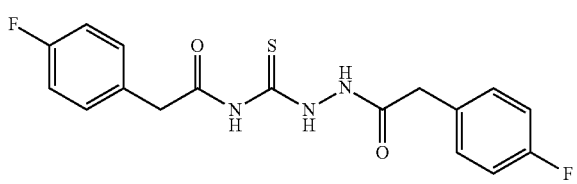 [SMILES: O=C(Cc1ccc(F)cc1)NNC(=S)NC(=O)Cc1ccc(F)cc1]

2-(4-Fluoro-phenyl)-N-{N'-[2-(4-fluoro-phenyl)-acetyl]-hydrazinocarbothioyl}-acetamide Yield: 35%

Melting point: 178 to 179° C.

$^1$H-NMR (400 MHz, DMSO-d$_6$) δ: 3.57 (2H, s), 3.74 (2H, s), 7.12-7.32 (8H, m), 11.03 (1H, br), 11.72 (1H, br), 12.28 (1H, br)

$^{13}$C-NMR (100 MHz, DMSO-d$_6$) δ: 38.60, 41.08, 115.03 (t, J=20.3 Hz), 128.22, 129.15, 130.38 (d, J=2.5 Hz), 131.01 (d, J=7.9 Hz), 131.32 (d, J=7.9 Hz), 161.32 (d, J=242.3 Hz), 167.24, 172.38, 176.98

MS (EI): m/z 363 (M$^+$)

2-(2,6-Difluorophenyl)-N—[N'-[2-(4-fluorophenyl)acetyl]hydrazinocarbothioyl]acetamide

LW-33

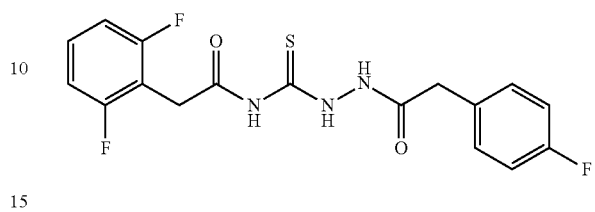

2-(2,6-Difluoro-phenyl)-N-{N'-[2-(4-fluoro-phenyl)-acetyl]-hydrazinocarbothioyl}-acetamide Yield: 59%

Melting point: 186 to 187° C.

$^1$H-NMR (400 MHz, DMSO-d$_6$) δ: 3.57 (2H, s), 3.88 (2H, s), 7.08-7.14 (4H, m), 7.30-7.40 (3H, m), 11.03 (1H, br), 11.86 (1H, br), 12.09 (1H, br)

$^{13}$C-NMR (100 MHz, DMSO-d$_6$) δ: 29.27, 30.70, 38.62, 111.34 (dd, J=5.8, 19.0 Hz), 114.95 (d, J=20.7 Hz), 129.83 (t, J=10.3 Hz), 131.03 (d, J=8.3 Hz), 131.40 (d, J=3.3 Hz), 159.81 (t, J=10.3 Hz), 162.25 (t, J=8.3 Hz), 167.31, 170.28, 176.85

MS (EI): m/z 381 (M$^+$)

Example 13

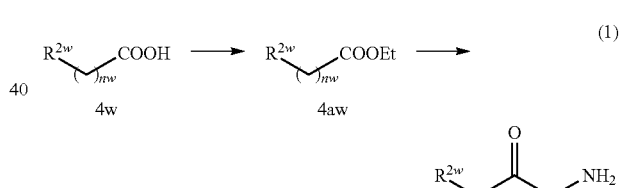

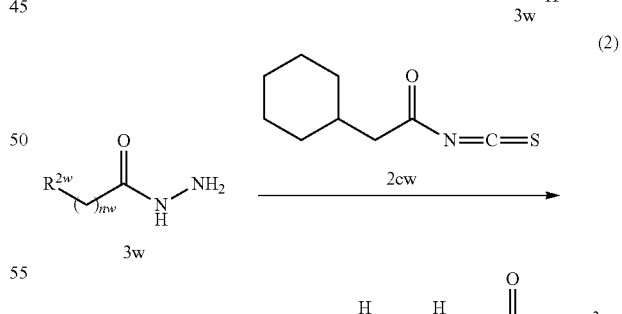

(1) Concentrated hydrochloric acid (one drop) was added to an ethanol (3 mL) solution of the carboxylic acid represented by the general formula 4w (1 mmol) in an argon atmosphere, and the mixture was refluxed with heating overnight.

After evaporating the solvent, a saturated sodium bicarbonate solution was added to the mixture until the aqueous layer became basic, followed by extraction with methylene chloride.

The organic layer was dried over sodium sulfate, and filtered, and the solvent was evaporated to obtain the ethyl ester compound represented by the general formula 4aw.

(2) Hydrazine monohydrate (0.05 mL, 1 mmol) was added to an ethanol (0.5 mL) solution of the ethyl ester compound represented by the general formula 4aw (1 mmol) in an argon atmosphere, and the mixture was refluxed with heating overnight to obtain the hydrazine compound represented by the general formula 3w.

After evaporating the solvent, a methylene chloride (5 mL) solution of the isothiocyanate compound represented by the general formula 2cw (1 mmol) was added to the mixture using a cannula, and the mixture was stirred at room temperature overnight. The reaction mixture was filtered under suction to obtain the thiourea compound represented by the general formula 1cw.

2-Cyclohexyl-N—[N'-[2-(4-fluorophenyl)acetyl]hydrazinocarbothioyl]acetamide

LW-34

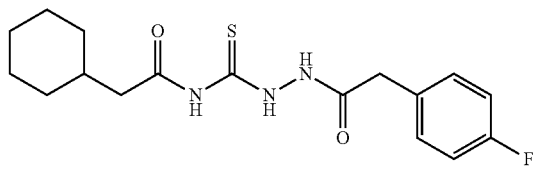 [SMILES: O=C(Cc1ccc(F)cc1)NNC(=S)NC(=O)CC1CCCCC1]

2-Cyclohexyl-N-{N'-[2-(4-fluoro-phenyl)-acetyl]-hydrazinocarbothioyl}-acetamide

Yield: 62%
Melting point: 132 to 133° C.
$^1$H-NMR (400 MHz, DMSO-$d_6$) δ: 0.93-1.92 (5H, m), 2.27 (2H, d, J=6.8 Hz), 3.58 (2H, s), 7.13 (2H, t, J=8.8 Hz), 7.30-7.40 (2H, m), 11.04 (1H, br), 11.46 (1H, br), 12.42 (1H, br)
$^{13}$C-NMR (100 MHz, DMSO-$d_6$) δ: 24.48, 25.66, 32.24, 34.55, 38.60, 42.93, 114.96 (d, J=21.5 Hz), 131.04 (d, J=8.3 Hz), 131.43 (d, J=2.5 Hz), 163.90 (d, J=282.9 Hz), 167.33, 174.15, 176.75 MS (EI): m/z 351 (M$^+$)

N—[N'-[2-(4-Fluorophenyl)acetyl]hydrazinocarbothioyl]-2-thiophen-2-ylacetamide

LW-35

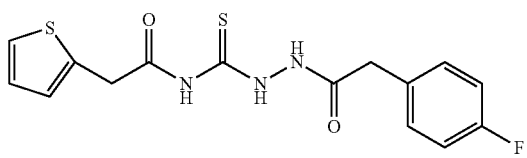 [SMILES: O=C(Cc1ccc(F)cc1)NNC(=S)NC(=O)Cc1cccs1]

N-{N'-[2-(4-Fluoro-phenyl)-acetyl]-hydrazinocarbothioyl}-2-thiophen-2-yl-acetamide Yield: 28%
$^1$H-NMR (500 MHz, DMSO-$d_6$) δ: 3.57 (2H, s), 3.98 (2H, s), 6.96-7.00 (2H, m), 7.12 (2H, t, J=8.7 Hz), 7.33 (2H, dd, J=8.7, 5.7 Hz), 7.41 (1H, dd, J=3.8, 2.6 Hz), 11.03 (1H, br), 11.74 (1H, br), 12.18 (1H, br)

N—[N'-[2-(4-Fluorophenyl)acetyl]hydrazinocarbothioyl]-3-phenylpropionamide

LW-36

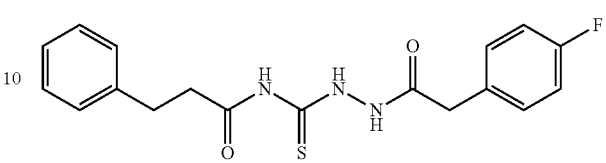

N-{N'-[2-(4-Fluoro-phenyl)-acetyl]hydrazinocarbothioyl}-3-phenyl-propionamide

Yield: 42%
$^1$H-NMR (500 MHz, DMSO-$d_6$) δ: 2.72 (2H, t, J=7.5 Hz), 2.83 (2H, t, J=7.5 Hz), 3.58 (2H, s), 7.13 (2H, t, J=9.0 Hz), 7.17 (1H, td, J=7.4, 1.7 Hz), 7.21 (2H, dd, J=7.4, 1.7 Hz), 7.27 (2H, td, J=7.4, 1.7 Hz), 7.34 (2H, dd, J=9.0, 5.6 Hz), 11.02 (1H, br), 11.52 (1H, br), 12.33 (1H, br)

Example 14

4-Methyl-N-[2-(3-phenylureido)ethyl]benzenesulfonamide

ED-1

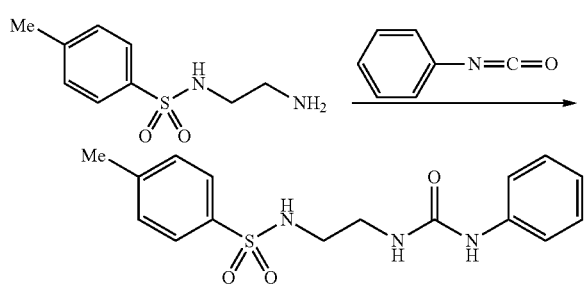

Phenyl isocyanate (0.051 mL, 0.47 mmol) was added to 5 mL of a methylene chloride solution of N-(2-aminoethyl)-4-methylbenzenesulfonamide (100 mg, 0.47 mmol), and the mixture was stirred at room temperature overnight.

After evaporating the solvent, the residue was purified by silica gel column chromatography (15 g, hexane:acetone=10:1 to 1:1) to obtain 4-methyl-N-[2-(3-phenylureido)ethyl]benzenesulfonamide (colorless crystals) (89 mg, 57%).

$^1$H-NMR (400 MHz, CDCl$_3$): δ 2.38 (3H, s), 3.06 (2H, t, J=5.4 Hz), 3.34 (2H, t, J=5.4 Hz), 5.17 (1H, br), 5.40 (1H, br), 6.51 (1H, br), 7.07 (1H, t, J=7.0 Hz), 7.24-7.31 (6H, m), 7.72 (2H, d, J=8.1 Hz)

$^{13}$C-NMR (125 MHz, DMSO-$d_6$): δ 20.92, 38.82, 42.82, 117.65, 121.05, 126.55, 128.62, 129.63, 137.30, 140.40, 142.64, 155.15

IR (KBr): 1161, 1325, 1593, 1645, 3302 cm$^{-1}$
MS (EI): m/z 333 (M$^+$)
Melting point: 154 to 155° C. (recrystallization solvent: toluene)

Example 15

The following compounds were obtained in the same manner as in Example 14.

N-[2-[3-(4-Fluorophenyl)ureido]ethyl]-4-methylbenzenesulfonamide

ED-3

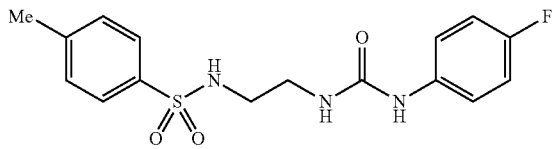 [SMILES: Cc1ccc(S(=O)(=O)NCCNC(=O)Nc2ccc(F)cc2)cc1]

N-{2-[3-(4-Fluoro-phenyl)-ureido]ethyl}-4-methyl-benzenesulfonamide

Yield: 88%

$^1$H-NMR (400 MHz, CDCl$_3$): δ 2.40 (3H, s), 3.07 (2H, t, J=4.8 Hz), 3.35 (2H, t, J=4.8 Hz), 5.12 (1H, br), 5.33 (1H, br), 6.45 (1H, br), 6.97 (2H, t, J=8.2 Hz), 7.24-7.29 (4H, m), 7.72 (2H, d, J=7.8 Hz)

$^{13}$C-NMR (125 MHz, DMSO-d$_6$): δ 20.92, 38.88, 42.81, 115.07 (d, J=21.6 Hz), 119.27 (d, J=8.4 Hz), 126.56, 129.64, 136.78 (d, J=2.4 Hz), 137.33, 142.65, 155.22, 156.91 (d, J=237.5 Hz)

IR (KBr): 1165, 1323, 1508, 1645, 3314 cm$^{-1}$

MS (EI): m/z 351 (M$^+$)

Melting point: 161 to 162° C. (recrystallization solvent: toluene)

N-[2-[3-(3,4-Dichlorophenyl)ureido]ethyl]-4-methylbenzenesulfonamide

ED-4

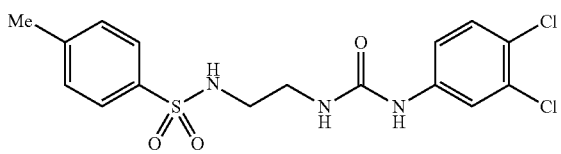 [SMILES: Cc1ccc(S(=O)(=O)NCCNC(=O)Nc2ccc(Cl)c(Cl)c2)cc1]

N-{2-[3-(3,4-Dichloro-phenyl)-ureido]-ethyl}-4-methyl-benzenesulfonamide

Yield: 62%

$^1$H-NMR (400 MHz, CDCl$_3$): δ 2.40 (3H, s), 3.07 (2H, t, J=4.9 Hz), 3.37 (2H, t, J=4.9 Hz), 5.52 (2H, m), 7.01 (1H, br), 7.10 (1H, dd, J=8.7, 2.4 Hz), 7.22-7.27 (1H, m), 7.28 (2H, d, J=8.1 Hz), 7.48 (1H, d, J=2.4 Hz), 7.71 (2H, d, J=8.1 Hz)

$^{13}$C-NMR (125 MHz, DMSO-d$_6$): δ 20.89, 38.90, 42.56, 117.68, 118.66, 122.24, 126.54, 129.61, 130.37, 130.90, 137.30, 142.61, 154.76

IR (KBr): 1157, 1319, 1541, 1674, 3393 cm$^{-1}$

MS (EI): m/z 401 (M$^+$)

Melting point: 154 to 155° C.

N-[2-[3-(2-Methoxyphenyl)ureido]ethyl]-4-methylbenzenesulfonamide

ED-5

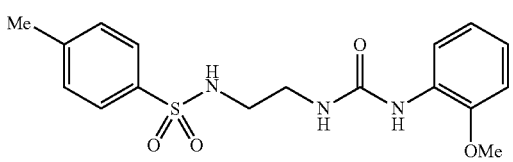 [SMILES: COc1ccccc1NC(=O)NCCNS(=O)(=O)c1ccc(C)cc1]

N-{2-[3-(2-Methoxy-phenyl)-ureido]-ethyl}-4-methyl-benzenesulfonamide

Yield: 89%

$^1$H-NMR (400 MHz, CDCl$_3$): δ 2.39 (3H, s), 3.10 (2H, t, J=5.6 Hz), 3.37 (2H, t, J=5.6 Hz), 3.85 (3H, s), 5.10 (1H, br), 5.33 (1H, br), 6.80 (1H, br), 6.86 (1H, dd, J=7.8, 1.6 Hz), 6.94 (1H, td, J=7.8, 1.6 Hz), 7.01 (1H, td, J=7.8, 1.6 Hz), 7.25-7.27 (2H, m), 7.74 (2H, d, J=8.3 Hz), 7.92 (1H, dd, J=7.8, 1.6 Hz)

$^{13}$C-NMR (125 MHz, DMSO-d$_6$): δ 20.92, 38.86, 42.94, 55.61, 110.53, 118.04, 120.45, 121.04, 126.58, 129.38, 129.63, 137.34, 142.65, 147.34, 155.22

IR (KBr): 1155, 1321, 1572, 1647, 3277 cm$^{-1}$

MS (EI): m/z 363 (M$^+$)

Melting point: 184 to 185° C.

N-[2-[3-(2-Methoxyphenyl)thioureido]ethyl]-4-methylbenzenesulfonamide

ED-6

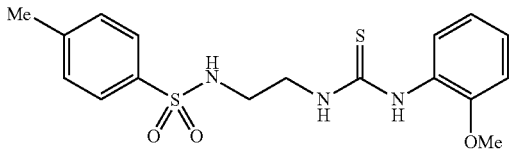 [SMILES: COc1ccccc1NC(=S)NCCNS(=O)(=O)c1ccc(C)cc1]

N-{2-[3-(2-Methoxy-phenyl)-thioureido]-ethyl}-4-methyl-benzenesulfonamide

Yield: 73%

$^1$H-NMR (400 MHz, CDCl$_3$): δ 2.41 (3H, s), 3.20 (2H, t, J=5.5 Hz), 3.78 (2H, t, J=5.5 Hz), 3.88 (3H, s), 6.49 (1H, br), 6.99-7.03 (2H, m), 7.26-7.30 (5H, m), 7.59 (1H, br), 7.71 (2H, d, J=8.3 Hz)

$^{13}$C-NMR (125 MHz, CDCl$_3$): δ 21.43, 42.43, 44.48, 55.74, 111.97, 121.10, 124.93, 125.40, 126.95, 127.80, 129.71, 136.40, 143.50, 152.46, 180.92

MS (EI): m/z 379 (M$^+$)

115

N-[2-[3-(3-Methoxyphenyl)ureido]ethyl]-4-methyl-benzenesulfonamide

ED-7

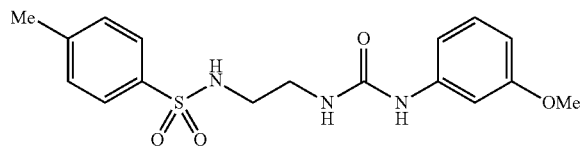 [SMILES: COc1cccc(NC(=O)NCCNS(=O)(=O)c2ccc(C)cc2)c1]

N-{2-[3-(3-Methoxy-phenyl)-ureido]-ethyl}-4-methyl-benzenesulfonamide

Yield: 97%

$^1$H-NMR (400 MHz, CDCl$_3$): δ 2.38 (3H, s), 3.04 (2H, t, J=5.1 Hz), 3.33 (2H, t, J=5.1 Hz), 3.74 (3H, s), 6.58 (1H, d, J=7.8 Hz), 6.78 (1H, d, J=7.8 Hz), 6.99 (1H, s), 7.05 (1H, br), 7.13 (1H, t, J=7.8 Hz), 7.20-7.30 (2H, m), 7.72 (2H, d, J=8.3 Hz)

$^{13}$C-NMR (125 MHz, DMSO-d$_6$): δ 20.92, 38.83, 42.82, 54.82, 103.47, 106.47, 110.04, 126.56, 129.37, 129.65, 137.32, 141.66, 142.66, 155.10, 159.65

IR (KBr): 1163, 1329, 1560, 1655, 3350 cm$^{-1}$

MS (EI): m/z 363 (M$^+$)

Melting point: 136 to 137° C.

N-[2-[3-(2-Ethoxyphenyl)ureido]ethyl]-4-methyl-benzenesulfonamide

ED-8

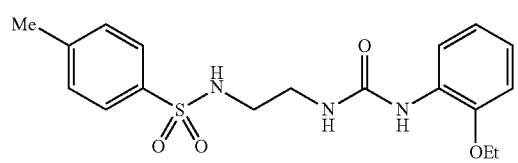

N-{2-[3-(2-Ethoxy-phenyl)-ureido]ethyl}-4-methyl-benzenesulfonamide

Yield: 40%

$^1$H-NMR (400 MHz, CDCl$_3$): δ 1.45 (3H, t, J=7.1 Hz), 2.39 (3H, s), 3.11 (2H, t, J=5.4 Hz), 3.38 (2H, t, J=5.4 Hz), 4.09 (2H, q, J=7.1 Hz), 6.88 (1H, d, J=7.1 Hz), 6.93 (1H, t, J=7.1 Hz), 7.00 (1H, t, J=7.1 Hz), 7.26-7.31 (2H, m), 7.51 (1H, br), 7.74 (2H, d, J=8.1 Hz), 7.88 (1H, d, J=7.1 Hz)

$^{13}$C-NMR (125 MHz, DMSO-d$_6$): δ 14.68, 20.92, 38.86, 42.89, 63.81, 111.56, 118.04, 120.36, 121.00, 126.56, 129.55, 129.63, 137.30, 142.64, 146.39, 155.12

MS (EI): m/z 377 (M$^+$)

Melting point: 129 to 130° C.

116

N-[2-[3-(2,4-Dichlorophenyl)ureido]ethyl]-4-methylbenzenesulfonamide

ED-10

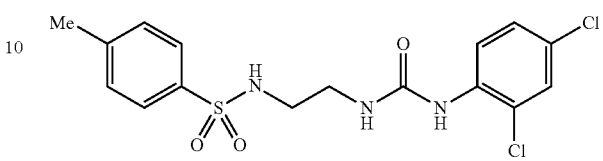

N-{2-[3-(2,4-Dichloro-phenyl)-ureido]-ethyl}-4-methyl-benzenesulfonamide

Yield: 90%

$^1$H-NMR (400 MHz, CDCl$_3$): δ 2.39 (3H, s), 3.11 (2H, t, J=4.8 Hz), 3.37 (2H, t, J=4.8 Hz), 5.11 (1H, br), 5.33 (1H, br), 6.73 (1H, br), 7.18-7.32 (4H, m), 7.72 (2H, d, J=7.8 Hz), 8.08 (1H, d, J=8.8 Hz)

$^{13}$C-NMR (125 MHz, DMSO-d$_6$): δ 20.91, 38.92, 42.62, 121.55, 121.78, 125.17, 126.56, 127.44, 128.36, 129.61, 135.89, 137.28, 142.63, 154.61

MS (EI): m/z 401 (M$^+$)

Melting point: 161 to 162° C. (recrystallization solvent: toluene)

4-Methyl-N-[2-(3-m-tolylureido)ethyl]benzene-sulfonamide

ED-11

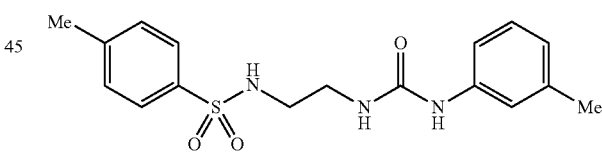

4-Methyl-N-[2-(3-m-tolyl-ureido)-ethyl]-benzene-sulfonamide

Yield: 53%

$^1$H-NMR (400 MHz, CDCl$_3$): δ 2.26 (3H, s), 2.37 (3H, s), 3.03 (2H, t, J=5.0 Hz), 3.32 (2H, t, J=5.0 Hz), 6.84 (1H, d, J=7.6 Hz), 7.02 (1H, d, J=7.6 Hz), 7.07 (1H, br), 7.12 (1H, t, J=7.6 Hz), 7.24-7.30 (5H, m), 7.71 (2H, d, J=8.1 Hz)

$^{13}$C-NMR (125 MHz, DMSO-d$_6$): δ 20.96, 21.26, 38.81, 42.86, 114.89, 118.25, 121.84, 126.57, 128.47, 129.62, 137.33, 137.71, 140.30, 142.67, 155.18

Melting point: 114 to 115° C. (recrystallization solvent: toluene)

4-Methyl-N-[2-(3-o-tolyl-thioureido)ethyl]benzene-sulfonamide

ED-12

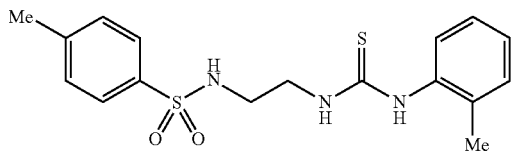 [SMILES: Cc1ccc(S(=O)(=O)NCCNC(=S)Nc2ccccc2C)cc1]

4-Methyl-N-[2-(3-o-tolyl-thioureido)-ethyl]benzene-sulfonamide

Yield: 80%

$^1$H-NMR (400 MHz, CDCl$_3$): δ 2.26 (3H, s), 2.40 (3H, s), 3.14 (2H, t, J=4.8 Hz), 3.73 (2H, t, J=4.8 Hz), 4.14 (1H, br), 6.16 (1H, br), 7.13-7.26 (5H, m), 7.27 (2H, d, J=7.8 Hz), 7.68 (2H, d, J=7.8 Hz)

$^{13}$C-NMR (125 MHz, DMSO-d$_6$): δ 17.68, 21.03, 40.03, 41.71, 126.34, 126.49, 127.71, 129.67, 129.69, 130.69, 134.73, 136.72, 137.33, 142.67, 181.13

Melting point: 131 to 132° C.

N-[2-[3-(2-Methoxy-5-methylphenyl)thioureido]ethyl]-4-methylbenzenesulfonamide

ED-13

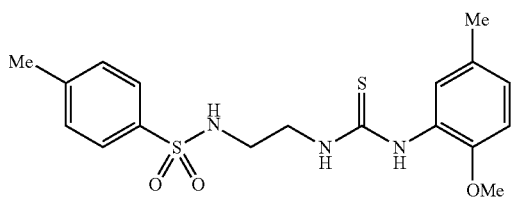 [SMILES: COc1ccc(C)cc1NC(=S)NCCNS(=O)(=O)c1ccc(C)cc1]

N-{2-[3-(2-Methoxy-5-methyl-phenyl)-thioureido]-ethyl}-4-methyl-benzenesulfonamide Yield: 83%

$^1$H-NMR (400 MHz, CDCl$_3$): δ 2.29 (3H, s), 2.39 (3H, s), 3.19 (2H, t, J=5.1 Hz), 3.75 (2H, t, J=5.1 Hz), 3.82 (3H, s), 6.86 (1H, d, J=7.3 Hz), 7.00-7.15 (2H, m), 7.20-7.26 (3H, m), 7.27 (2H, d, J=8.1 Hz), 7.70 (2H, d, J=8.1 Hz)

$^{13}$C-NMR (125 MHz, DMSO-d$_6$): δ 20.27, 20.96, 41.71, 43.32, 55.60, 111.53, 126.26, 126.41, 126.57, 126.80, 128.78, 129.69, 137.33, 142.67, 149.99, 180.59

Melting point: 130 to 131° C.

N-[2-[3-(2-Chlorophenyl)thioureido]ethyl]-4-methylbenzenesulfonamide

ED-15

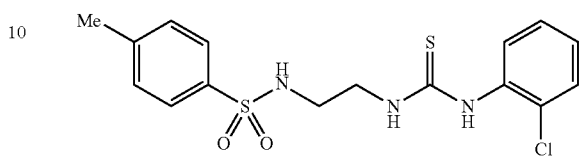

N-{2-[3-(2-Chloro-phenyl)-thioureido]-ethyl}-4-methyl-benzenesulfonamide

Yield: 99%

$^1$H-NMR (400 MHz, CDCl$_3$): δ 2.40 (3H, s), 3.18 (2H, t, J=5.1 Hz), 3.79 (2H, t, J=5.1 Hz), 6.63 (1H, br), 7.20-7.27 (3H, m), 7.28 (2H, d, J=7.6 Hz), 7.34 (1H, t, J=7.4 Hz), 7.40-7.52 (2H, m), 7.70 (2H, d, J=7.6 Hz)

$^{13}$C-NMR (125 MHz, CDCl$_3$): δ 21.45, 42.28, 44.65, 126.91, 127.59, 127.90, 128.05, 129.71, 129.73, 130.34, 133.54, 136.14, 143.69, 181.16

N-[2-[3-(3,4-Dichlorophenyl)ureido]ethyl]-4-methoxybenzenesulfonamide

ED-16

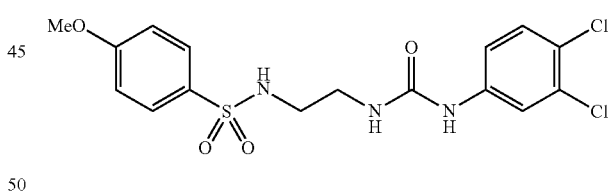

N-{2-[3-(3,4-Dichloro-phenyl)-ureido]-ethyl}-4-methoxy-benzenesulfonamide

Yield: 70%

$^1$H-NMR (400 MHz, CDCl$_3$): δ 3.07 (2H, t, J=5.1 Hz), 3.38 (2H, t, J=5.1 Hz), 3.84 (3H, s), 6.90 (3H, m), 7.12 (1H, dd, J=9.0, 1.2 Hz), 7.20-7.30 (2H, m), 7.37 (1H, br), 7.51 (1H, d, J=1.2 Hz), 7.77 (2H, d, J=8.3 Hz)

$^{13}$C-NMR (125 MHz, DMSO-d$_6$): δ 38.89, 42.55, 55.60, 114.36, 117.71, 118.63, 122.22, 128.70, 130.38, 130.92, 131.83, 140.68, 154.80, 162.13

Melting point: 150 to 151° C.

4-Bromo-N-[2-[3-(3,4-dichlorophenyl)ureido]ethyl]benzenesulfonamide

ED-17

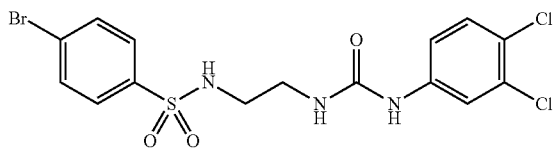

4-Bromo-N-{2-[3-(3,4-dichloro-phenyl)-ureido]ethyl}-benzenesulfonamide

Yield: 45%

$^1$H-NMR (400 MHz, CDCl$_3$): δ 3.12 (2H, t, J=5.6 Hz), 3.40 (2H, t, J=5.6 Hz), 7.00 (1H, br), 7.14 (1H, dd, J=8.8, 2.6 Hz), 7.31 (1H, d, J=8.8 Hz), 7.35 (1H, br), 7.42 (1H, br), 7.53 (1H, d, J=2.6 Hz), 7.65 (2H, d, J=8.7 Hz), 7.72 (2H, d, J=8.7 Hz)

$^{13}$C-NMR (100 MHz, DMSO-d$_6$): δ 42.51, 54.90, 117.69, 118.66, 122.24, 126.21, 128.53, 130.41, 130.90, 132.29, 139.53, 140.62, 154.75

MS (EI): m/z 465 (M+)

Melting point: 129 to 130° C.

4-Chloro-N-[2-[3-(3,4-dichlorophenyl)ureido]ethyl]-4-benzenesulfonamide

ED-18

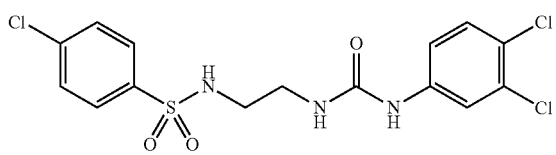

4-Chloro-N-{2-[3-(3,4-dichloro-phenyl)-ureido]-ethyl}-benzenesulfonamide

Yield: 14%

$^1$H-NMR (400 MHz, CDCl$_3$): δ 3.08 (2H, t, J=5.1 Hz), 3.37 (2H, t, J=5.1 Hz), 5.43 (1H, br), 5.73 (1H, br), 6.94 (1H, br), 7.10 (1H, dd, J=8.4, 2.3 Hz), 7.21-7.27 (1H, m), 7.46 (2H, d, J=8.5 Hz), 7.49 (1H, d, J=2.3 Hz), 7.77 (2H, d, J=8.5 Hz)

$^{13}$C-NMR (125 MHz, Acetone-d$_6$): δ 40.25, 44.30, 118.62, 120.07, 129.90, 129.53, 130.07, 131.14, 132.43, 138.77, 140.52, 141.51, 155.94

Melting point: 139 to 140° C.

N-[2-[3-(3,4-Dichlorophenyl)ureido]ethyl]-4-fluorobenzenesulfonamide

ED-19

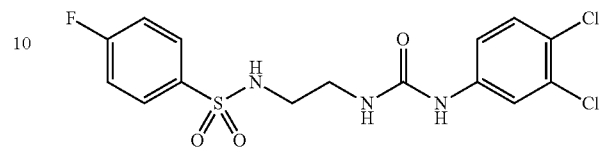

N-{2-[3-(3,4-Dichloro-phenyl)-ureido]-ethyl}-4-fluoro-benzenesulfonamide

Yield: 67%

$^1$H-NMR (400 MHz, CDCl$_3$): δ 3.11 (2H, t, J=5.3 Hz), 3.19 (2H, t, J=5.3 Hz), 6.67 (1H, br), 6.98 (1H, br), 7.13 (1H, dd, J=8.6, 2.2 Hz), 7.18 (2H, t, J=8.7 Hz), 7.30 (1H, d, J=8.6 Hz), 7.40 (1H, br), 7.52 (1H, d, J=2.2 Hz), 7.86 (2H, dd, J=8.7, 5.0 Hz)

$^{13}$C-NMR (125 MHz, DMSO-d$_6$): δ 38.97, 42.55, 116.34 (d, J=19.2 Hz), 117.71, 118.71, 122.29, 129.50 (d, J=9.6 Hz), 130.38, 130.92, 136.60 (d, J=3.6 Hz), 140.61, 154.80, 164.11 (d, J=249.5 Hz)

Melting point: 153 to 154° C.

N-[2-[3-(4-Bromo-2-chlorophenyl)ureido]ethyl]-4-methylbenzenesulfonamide

ED-20

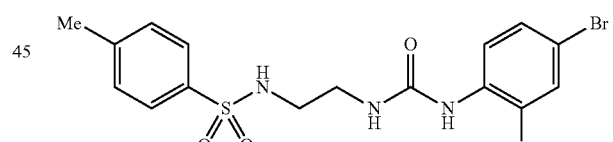

N-{2-[3-(4-Bromo-2-chloro-phenyl)-ureido]-ethyl}-4-methyl-benzenesulfonamide

Yield: 76%

$^1$H-NMR (400 MHz, CDCl$_3$): δ 2.41 (3H, s), 3.12 (2H, t, J=5.3 Hz), 3.41 (2H, t, J=5.3 Hz), 6.79 (1H, br), 7.00 (1H, br), 7.23 (1H, br), 7.29 (2H, d, J=8.1 Hz), 7.33 (1H, dd, J=8.8, 2.3 Hz), 7.46 (1H, d, J=2.3 Hz), 7.74 (2H, d, J=8.1 Hz), 8.02 (1H, d, J=8.8 Hz)

$^{13}$C-NMR (125 MHz, DMSO-d$_6$): δ 21.11, 38.89, 42.78, 112.75, 122.06, 126.71, 126.72, 129.77, 130.46, 131.14, 136.41, 137.48, 142.82, 154.72

Melting point: 164 to 165° C.

121

N-[3-[3-(3,4-Dichlorophenyl)ureido]propyl]-4-methylbenzenesulfonamide

ED-21

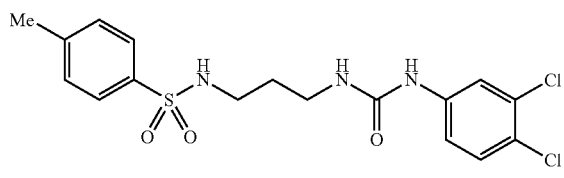 [SMILES: Cc1ccc(S(=O)(=O)NCCCNC(=O)Nc2ccc(Cl)c(Cl)c2)cc1]

N-{3-[3-(3,4-Dichloro-phenyl)-ureido]-propyl}-4-methyl-benzenesulfonamide

Yield: 86%

$^1$H-NMR (500 MHz, CDCl$_3$): δ 1.68 (2H, quint, J=5.4 Hz), 2.40 (3H, s), 2.99 (2H, t, J=5.4 Hz), 3.36 (2H, t, J=5.4 Hz), 5.30 (1H, br), 5.42 (1H, br), 6.91 (1H, br), 7.15 (1H, dd, J=8.7, 2.5 Hz), 7.24-7.28 (2H, m), 7.30 (1H, d, J=8.7 Hz), 7.55 (1H, d, J=2.5 Hz), 7.72 (2H, d, J=8.6 Hz)

$^{13}$C-NMR (125 MHz, DMSO-d$_6$): δ 20.96, 29.73, 38.97, 40.34, 117.64, 118.71, 122.14, 126.49, 129.54, 130.31, 130.92, 137.48, 140.76, 142.59, 154.88

Melting point: 157 to 158° C.

4-Bromo-N-[3-[3-(3,4-dichlorophenyl)ureido]propyl]benzenesulfonamide

ED-22

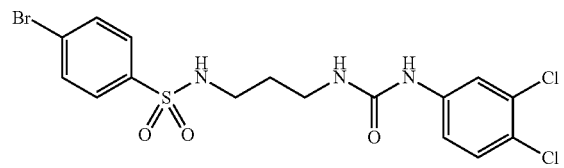 [SMILES: O=C(NCCCNS(=O)(=O)c1ccc(Br)cc1)Nc1ccc(Cl)c(Cl)c1]

4-Bromo-N-{3-[3-(3,4-dichloro-phenyl)-ureido]-propyl}-benzenesulfonamide

Yield: 80%

$^1$H-NMR (500 MHz, CDCl$_3$): δ 1.70 (2H, quint, J=6.0 Hz), 3.00 (2H, t, J=6.0 Hz), 3.39 (2H, t, J=6.0 Hz), 4.95 (1H, br), 5.55 (1H, br), 6.40 (1H, br), 7.13 (1H, dd, J=9.0, 2.5 Hz), 7.35 (1H, d, J=9.0 Hz), 7.54 (1H, d, J=2.5 Hz), 7.60 (2H, d, J=8.6 Hz), 7.71 (2H, d, J=8.6 Hz)

$^{13}$C-NMR (125 MHz, DMSO-d$_6$): δ 29.73, 36.52, 40.34, 117.64, 118.71, 122.22, 126.18, 128.55, 130.38, 130.92, 132.29, 139.69, 140.76, 154.88

Melting point: 163 to 164° C.

122

N-[3-[3-(3,4-Dichlorophenyl)ureido]propyl]-4-fluorobenzenesulfonamide

ED-23

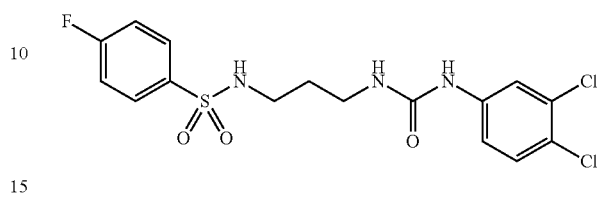

N-{3-[3-(3,4-Dichloro-phenyl)-ureido]-propyl}-4-fluoro-benzenesulfonamide

Yield: 82%

$^1$H-NMR (500 MHz, CDCl$_3$): δ 1.70 (2H, quint, J=6.0 Hz), 2.99 (2H, t, J=6.0 Hz), 3.37 (2H, t, J=6.0 Hz), 6.80 (1H, br), 6.92 (1H, br), 7.13 (1H, dd, J=8.6, 2.9 Hz), 7.15 (2H, t, J=8.5 Hz), 7.24-7.30 (1H, m), 7.33 (1H, d, J=8.6 Hz), 7.53 (1H, d, J=2.9 Hz), 7.85 (2H, dd, J=8.5, 4.8 Hz)

$^{13}$C-NMR (125 MHz, DMSO-d$_6$): δ 29.73, 36.60, 40.34, 116.34 (d, J=19.2 Hz), 117.71, 118.63, 122.14, 129.43 (d, J=9.6 Hz), 130.38, 130.92, 136.79 (d, J=2.8 Hz), 140.76, 154.88, 164.03 (d, J=249.5 Hz)

Melting point: 120 to 121° C.

N-[3-[3-(3,4-Dichlorophenyl)ureido]propyl]-4-methoxybenzenesulfonamide

ED-24

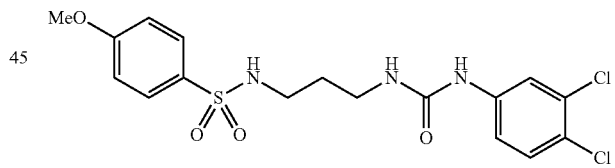

N-{3-[3-(3,4-Dichloro-phenyl)-ureido]-propyl}-4-methoxy-benzenesulfonamide

Yield: 64%

$^1$H-NMR (500 MHz, CDCl$_3$): δ 1.70 (2H, quint, J=6.0 Hz), 2.98 (2H, t, J=6.0 Hz), 3.38 (2H, t, J=6.0 Hz), 3.84 (3H, s), 6.80 (1H, br), 6.90 (1H, br), 6.91 (2H, d, J=8.6 Hz), 7.16 (1H, dd, J=8.6, 2.3 Hz), 7.32 (1H, d, J=8.6 Hz), 7.42 (1H, br), 7.56 (1H, d, J=2.3 Hz), 7.76 (2H, d, J=8.6 Hz)

$^{13}$C-NMR (125 MHz, DMSO-d$_6$): δ 29.21, 36.08, 39.74, 55.00, 113.76, 117.12, 118.11, 121.62, 128.10, 129.86, 130.39, 131.46, 140.24, 154.35, 161.53

Melting point: 124 to 125° C.

Example 16

The following compound was obtained in the same manner as in Example 14, except that a specific compound (1-isothiocyanato-3-methoxypropane) was used instead of phenyl isocyanate.

N-[2-[3-(3-Methoxypropyl)thioureido]ethyl]-4-methylbenzenesulfonamide

ED-14

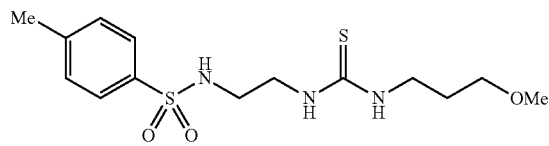 [SMILES: COCCCNC(=S)NCCNS(=O)(=O)c1ccc(C)cc1]

N-{2-[3-(3-Methoxy-propyl)-thioureido]-ethyl}-4-methyl-benzene sulfonamide

Yield: 99%
$^1$H-NMR (400 MHz, CDCl$_3$): δ 1.85 (2H, quint, J=5.2 Hz), 2.40 (3H, s), 3.15 (2H, t, J=4.5 Hz), 3.33 (3H, s), 3.45-3.55 (4H, m), 3.69 (2H, t, J=4.5 Hz), 7.29 (2H, d, J=8.2 Hz), 7.72 (2H, d, J=8.2 Hz)
$^{13}$C-NMR (125 MHz, CDCl$_3$): δ 21.45, 28.55, 42.66, 43.96, 53.73, 58.61, 70.59, 126.91, 129.73, 136.21, 143.54, 181.69

Example 17

The following compounds were obtained in the same manner as in Example 14, except that toluenesulfonyl isocyanate was used instead of phenyl isocyanate.

4-Methyl-N-[[2-(4-methylphenylsulfonamide)ethyl]carbamoyl]benzenesulfonamide

ED-2

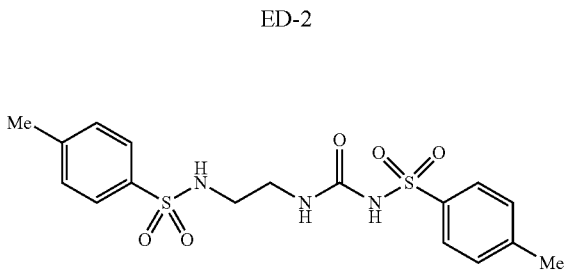

4-methyl-N-((2-(4-methylphenylsulfonamido)ethyl)carbamoyl)benzenesulfonamide

Yield: 80%
$^1$H-NMR (400 MHz, CDCl$_3$): δ 2.43 (3H, s), 2.44 (3H, s), 3.04 (2H, t, J=5.7 Hz), 3.33 (2H, t, J=5.7 Hz), 5.08 (1H, br), 6.70 (1H, br), 7.30 (2H, d, J=8.3 Hz), 7.35 (2H, d, J=8.5 Hz), 7.71 (2H, d, J=8.3 Hz), 7.82 (2H, d, J=8.5 Hz), 7.94 (1H, br)
$^{13}$C-NMR (125 MHz, DMSO-d$_6$): δ 20.96, 21.02, 38.91, 42.08, 126.51, 127.21, 129.43, 129.67, 137.22, 137.35, 142.71, 143.61, 151.41
IR (KBr): 1155, 1327, 1522, 1692, 3328 cm$^{-1}$
Melting point: 163 to 164° C.

2-Methyl-N-[[2-(4-methylphenylsulfonamide)ethyl]carbamoyl]benzenesulfonamide

ED-9

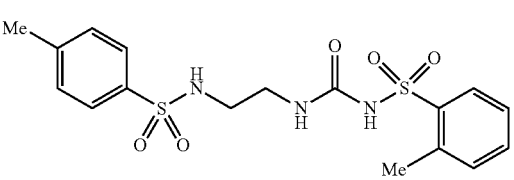 [SMILES: Cc1ccc(S(=O)(=O)NCCNC(=O)NS(=O)(=O)c2ccccc2C)cc1]

2-methyl-N-((2-(4-methylphenylsulfonamido)ethyl)carbamoyl)benzenesulfonamide

Yield: 14%
$^1$H-NMR (400 MHz, CDCl$_3$): δ 2.41 (3H, s), 2.62 (3H, s), 3.00 (2H, t, J=5.8 Hz), 3.31 (2H, t, J=5.8 Hz), 5.30 (1H, br), 6.62 (1H, br), 7.28 (2H, d, J=8.1 Hz), 7.32 (1H, d, J=7.6 Hz), 7.36 (1H, t, J=7.6 Hz), 7.51 (1H, t, J=7.6 Hz), 7.69 (2H, d, J=8.1 Hz), 8.01 (1H, d, J=7.6 Hz), 8.60 (1H, br)
$^{13}$C-NMR (125 MHz, CDCl$_3$): δ 14.11, 21.51, 39.84, 42.81, 126.44, 127.01, 129.72, 129.83, 132.73, 133.67, 136.38, 137.38, 137.44, 143.64, 152.44
Melting point: 134 to 135° C.

Example 18

The following compounds were obtained in the same manner as in Example 14, except that an aminophenyl compound was used instead of the alkylamino compound.

N-[2-[3-(3,4-Dichlorophenyl)ureido]phenyl]-4-methylbenzenesulfonamide

ED-25

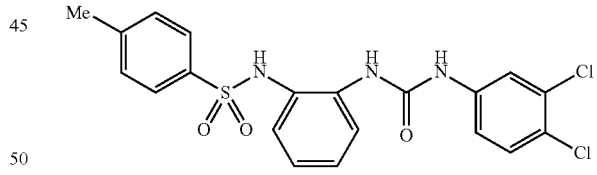

N-{2-[3-(3,4-Dichloro-phenyl)-ureido]-phenyl}-4-methyl-benzenesulfonamide

Yield: 75%
$^1$H-NMR (500 MHz, CDCl$_3$): δ 2.40 (3H, s), 6.68 (1H, dd, J=7.8, 1.2 Hz), 6.92 (1H, td, J=7.8, 1.2 Hz), 7.06 (1H, br), 7.10 (1H, br), 7.18 (1H, dd, J=9.0, 2.5 Hz), 7.20-7.27 (3H, m), 7.30 (1H, d, J=9.0 Hz), 7.57 (1H, br), 7.58 (1H, d, J=2.5 Hz), 7.64 (2H, d, J=8.6 Hz), 7.79 (1H, dd, J=7.8, 1.2 Hz)
$^{13}$C-NMR (100 MHz, DMSO-d$_6$): δ 21.00, 118.14, 119.16, 121.27, 122.41, 123.10, 125.35, 127.20, 127.32, 127.61, 129.52, 130.63, 131.11, 136.26, 136.46, 140.08, 143.30, 152.18
Melting point: 204 to 205° C.

125

N-[2-[3-(4-Fluorophenyl)ureido]phenyl]-4-methyl-benzenesulfonamide

ED-26

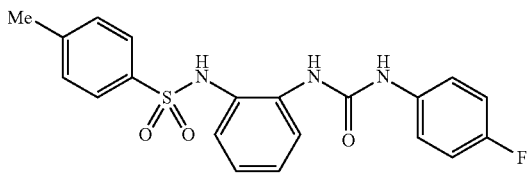 [SMILES: Cc1ccc(S(=O)(=O)Nc2ccccc2NC(=O)Nc2ccc(F)cc2)cc1]

N-{2-[3-(4-Fluoro-phenyl)-ureido]-phenyl}-4-methyl-benzenesulfonamide

Yield: 99%

¹H-NMR (500 MHz, CDCl₃): δ 2.41 (3H, s), 6.38 (1H, br), 6.80 (1H, br), 6.92-7.16 (3H, m), 7.19 (1H, td, J=7.8, 1.3 Hz), 7.23-7.35 (4H, m), 7.48 (1H, td, J=7.8, 1.3 Hz), 7.76 (2H, d, J=8.0 Hz), 7.87 (1H, dd, J=7.8, 1.3 Hz), 8.30 (1H, br)

¹³C-NMR (125 MHz, DMSO-d₆): δ 20.96, 115.04, 115.27 (d, J=19.2 Hz), 121.00, 121.99, 123.36, 125.12, 127.21 (d, J=9.6 Hz), 127.56, 129.54, 136.03, 136.41, 136.91 (d, J=3.0 Hz), 143.28, 152.74, 157.36 (d, J=239.9 Hz)

Melting point: 180 to 181° C.

4-Bromo-N-[2-[3-(3,4-dichlorophenyl)ureido]phenyl]benzenesulfonamide

ED-27

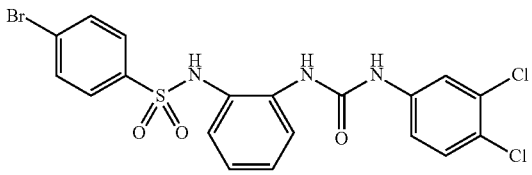 [SMILES: O=C(Nc1ccc(Cl)c(Cl)c1)Nc1ccccc1NS(=O)(=O)c1ccc(Cl)cc1]

4-Bromo-N-{2-[3-(3,4-dichloro-phenyl)-ureido]-phenyl}-benzenesulfonamide

Yield: 97%

¹H-NMR (400 MHz, CDCl₃): δ 6.69 (1H, dd, J=8.1, 1.5 Hz), 6.96 (1H, td, J=8.1, 1.5 Hz), 7.06 (1H, br), 7.10 (1H, br), 7.20 (1H, dd, J=8.7, 2.4 Hz), 7.21-7.25 (1H, m), 7.32 (1H, d, J=8.7 Hz), 7.42 (1H, br), 7.55-7.58 (4H, m), 7.59 (1H, d, J=2.4 Hz), 7.72 (1H, dd, J=8.1, 1.5 Hz)

¹³C-NMR (125 MHz, DMSO-d₆): δ 118.17, 119.21, 121.48, 122.61, 123.15, 124.98, 126.93, 127.47, 127.89, 129.14, 130.61, 131.12, 132.20, 136.49, 138.36, 139.98, 152.13

Melting point: 211 to 212° C.

126

4-Chloro-N-[2-[3-(3,4-dichlorophenyl)ureido]phenyl]benzenesulfonamide

ED-28

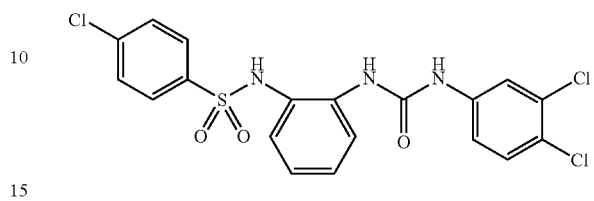

4-Chloro-N-{2-[3-(3,4-dichloro-phenyl)-ureido]-phenyl}-benzenesulfonamide

Yield: 83%

¹H-NMR (400 MHz, CDCl₃): δ 6.68 (1H, dd, J=7.6, 1.5 Hz), 6.94 (1H, td, J=7.6, 1.5 Hz), 7.15 (1H, dd, J=8.8, 2.4 Hz), 7.20 (1H, td, J=7.6, 1.5 Hz), 7.22-7.27 (2H, m), 7.29 (1H, d, J=8.8 Hz), 7.41 (2H, d, J=8.8 Hz), 7.48 (1H, br), 7.55 (1H, d, J=2.4 Hz), 7.65-7.69 (3H, m)

¹³C-NMR (125 MHz, DMSO-d₆): δ 118.17, 119.21, 121.48, 122.60, 123.15, 125.00, 127.48, 127.89, 129.07, 129.27, 130.60, 131.12, 136.50, 137.93, 139.98, 140.06, 152.15

Melting point: 199 to 200° C.

N-[2-[3-(3,4-Dichlorophenyl)ureido]phenyl]-4-fluorobenzenesulfonamide

ED-29

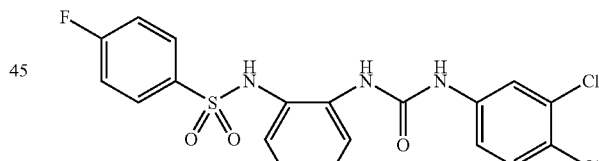

N-{2-[3-(3,4-Dichloro-phenyl)-ureido]-phenyl}-4-fluoro-benzenesulfonamide

Yield: 96%

¹H-NMR (400 MHz, CDCl₃): δ 6.61 (1H, dd, J=8.1, 1.5 Hz), 6.92 (1H, td, J=8.1, 1.5 Hz), 7.00 (1H, br), 7.13 (2H, t, J=8.5 Hz), 7.18-7.25 (3H, m), 7.31 (1H, d, J=8.5 Hz), 7.52 (1H, br), 7.60 (1H, d, J=2.4 Hz), 7.74 (2H, dd, J=8.5, 7.0 Hz), 7.78 (1H, dd, J=8.1, 1.5 Hz)

¹³C-NMR (125 MHz, DMSO-d₆): δ 116.31 (d, J=22.8 Hz), 118.16, 119.20, 121.35, 122.51, 123.16, 125.08, 127.46, 127.85, 130.25 (d, J=9.6 Hz), 130.62, 131.12, 135.36, 136.57, 140.01, 152.18, 164.43 (d, J=251.9 Hz)

Melting point: 203 to 204° C.

127

4-Methyl-N-[2-(3-phenyl-ureido)-phenyl]-benzene-sulfonamide

ED-30

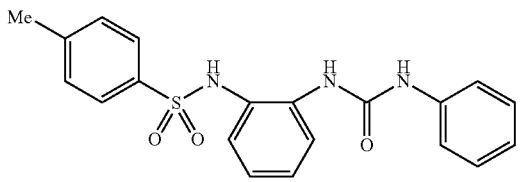 [SMILES: Cc1ccc(S(=O)(=O)Nc2ccccc2NC(=O)Nc2ccccc2)cc1]

4-Methyl-N-[2-(3-phenyl-ureido)-phenyl]-benzene-sulfonamide

Yield: 85%

$^1$H-NMR (400 MHz, CDCl$_3$): δ 2.34 (3H, s), 6.70 (1H, br), 6.83 (1H, dd, J=8.1, 1.5 Hz), 6.95 (1H, td, J=8.1, 1.5 Hz), 7.12-7.22 (5H, m), 7.25-7.34 (5H, m), 7.58 (2H, d, J=8.3 Hz), 7.66 (1H, dd, J=8.1, 1.5 Hz)

$^{13}$C-NMR (125 MHz, DMSO-d$_6$): δ 20.99, 115.89, 117.90, 118.15, 120.94, 121.84, 121.91, 125.07, 127.18, 128.81, 129.51, 136.43, 139.82, 140.87, 143.27, 152.46

Melting point: 83 to 84° C.

N-[2-[3-(3,4-Dichlorophenyl)ureido]phenyl]-4-methoxybenzenesulfonamide

ED-31

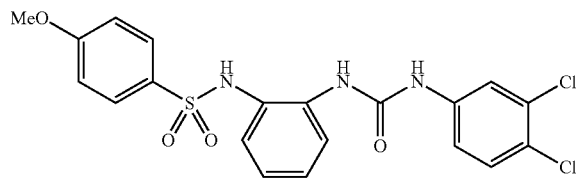 [SMILES: COc1ccc(S(=O)(=O)Nc2ccccc2NC(=O)Nc2ccc(Cl)c(Cl)c2)cc1]

N-{2-[3-(3,4-Dichloro-phenyl)-ureido]-phenyl}-4-methoxy-benzenesulfonamide

Yield: 93%

$^1$H-NMR (400 MHz, CDCl$_3$): δ 3.80 (3H, s), 6.66 (1H, dd, J=8.1, 1.5 Hz), 6.86 (2H, d, J=8.9 Hz), 6.88 (1H, td, J=8.1, 1.5 Hz), 7.13 (1H, dd, J=8.5, 2.4 Hz), 7.18 (1H, td, J=8.1, 1.5 Hz), 7.23-7.25 (2H, m), 7.29 (1H, br), 7.54 (1H, d, J=2.4 Hz), 7.61 (1H, br), 7.66 (2H, d, J=8.9 Hz), 7.76 (1H, dd, J=8.1, 1.5 Hz)

$^{13}$C-NMR (125 MHz, DMSO-d$_6$): δ 55.57, 114.18, 118.15, 119.16, 121.14, 122.38, 123.09, 125.48, 127.38, 127.54, 129.37, 130.62, 130.64, 131.09, 136.46, 140.06, 152.18, 162.51

Melting point: 129 to 130° C.

128

N-{2-[3-(3-Methoxy-phenyl)ureido]-phenyl}-4-methylbenzenesulfonamide

ED-32

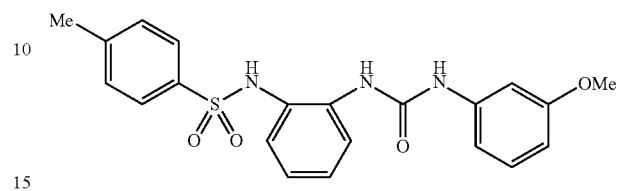

N-{2-[3-(3-Methoxy-phenyl)-ureido]-phenyl}-4-methyl-benzenesulfonamide

Yield: 59%

$^1$H-NMR (400 MHz, CDCl$_3$): δ 2.33 (3H, s), 3.77 (3H, s), 6.63 (1H, dd, J=8.1, 1.5 Hz), 6.77-6.82 (3H, m), 6.84 (1H, dd, J=8.2, 1.9 Hz), 6.94 (1H, td, J=8.1, 1.5 Hz), 7.02 (1H, t, J=1.9 Hz), 7.11-7.20 (4H, m), 7.33 (1H, br), 7.58 (2H, d, J=8.5 Hz), 7.72 (1H, dd, J=8.1, 1.5 Hz)

$^{13}$C-NMR (125 MHz, DMSO-d$_6$): δ 21.00, 54.88, 103.87, 107.32, 110.46, 115.89, 116.80, 121.94, 125.10, 127.20, 127.55, 129.51, 129.58, 136.43, 136.92, 141.08, 143.28, 152.40, 159.70

Melting point: 84 to 85° C.

N-[2-[3-(2-methoxyphenyl)ureido]phenyl]-4-methyl-benzenesulfonamide

ED-33

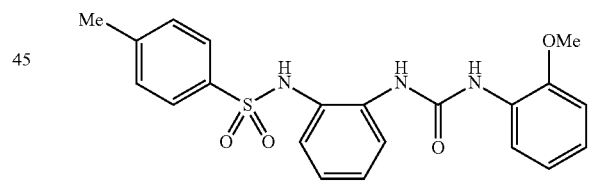

N-{2-[3-(2-Methoxy-phenyl)-ureido]-phenyl}-4-methyl-benzenesulfonamide

Yield: 68%

$^1$H-NMR (400 MHz, CDCl$_3$): δ 2.29 (3H, s), 3.83 (3H, s), 6.86 (1H, dd, J=8.1, 1.5 Hz), 6.93-7.00 (5H, m), 7.13-7.23 (5H, m), 7.56 (1H, dd, J=8.1, 1.5 Hz), 7.57 (2H, d, J=8.3 Hz), 7.99 (1H, dd, J=8.1, 1.7 Hz)

$^{13}$C-NMR (125 MHz, DMSO-d$_6$): δ 20.96, 55.73, 110.81, 119.21, 120.46, 121.84, 122.11, 122.39, 126.13, 126.64, 126.95, 127.03, 128.53, 129.47, 135.86, 136.85, 143.13, 148.18, 152.77

Melting point: 105 to 106° C.

4-Bromo-N-[2-[3-(2,4-dichlorophenyl)ureido]phenyl]benzenesulfonamide

ED-34

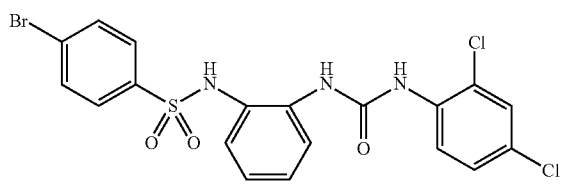

4-Bromo-N-{2-[3-(2,4-dichloro-phenyl)-ureido]-phenyl}-benzenesulfonamide

Yield: 96%

$^1$H-NMR (400 MHz, CDCl$_3$): δ 6.90 (1H, br), 7.01 (1H, dd, J=8.1, 1.5 Hz), 7.08 (1H, td, J=8.1, 1.5 Hz), 7.19 (1H, br), 7.20-7.26 (3H, m), 7.35 (1H, d, J=2.4 Hz), 7.51 (2H, d, J=8.8 Hz), 7.55 (2H, d, J=8.8 Hz), 7.57 (1H, dd, J=8.1, 1.5 Hz), 8.06 (1H, d, J=9.0 Hz)

$^{13}$C-NMR (125 MHz, DMSO-d$_6$): δ 122.14, 122.92, 123.28, 123.40, 125.78, 126.45, 126.81, 127.19, 127.52, 127.60, 128.62, 129.01, 132.17, 135.20, 135.98, 138.74, 152.34

Melting point: 209 to 210° C.

N-[2-[3-(2,4-Dichlorophenyl)ureido]phenyl]-4-fluorobenzenesulfonamide

ED-35

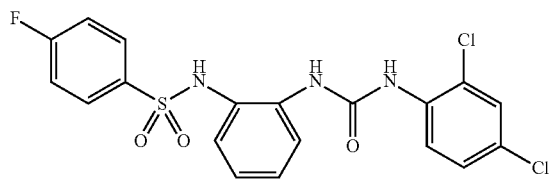 [SMILES: O=C(Nc1ccc(Cl)cc1Cl)Nc1ccccc1NS(=O)(=O)c1ccc(F)cc1]

N-{2-[3-(2,4-Dichloro-phenyl)-ureido]-phenyl}-4-fluoro-benzenesulfonamide

Yield: 95%

$^1$H-NMR (400 MHz, CDCl$_3$): δ 6.92 (1H, dd, J=8.1, 1.5 Hz), 6.93 (1H, br), 7.02-7.08 (3H, m), 7.14 (1H, br), 7.21-7.25 (2H, m), 7.32 (1H, br), 7.34 (1H, d, J=2.2 Hz), 7.63 (1H, dd, J=8.1, 1.5 Hz), 7.72 (2H, dd, J=8.8, 4.9 Hz), 8.07 (1H, d, J=9.0 Hz)

$^{13}$C-NMR (125 MHz, DMSO-d$_6$): δ 116.27 (d, J=22.8 Hz), 122.07, 122.85, 123.31, 123.46, 125.91, 126.51, 127.21, 127.52, 127.56, 128.64, 130.12 (d, J=9.6 Hz), 135.23, 135.77 (d, J=2.4 Hz), 136.07, 152.42, 164.39 (d, J=250.7 Hz)

Melting point: 201 to 202° C.

4-Chloro-N-[2-[3-(2,4-dichlorophenyl)ureido]phenyl]benzenesulfonamide

ED-36

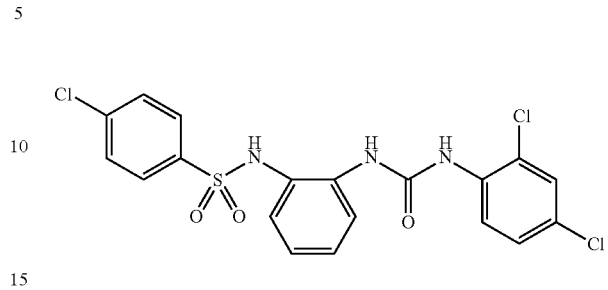

4-Chloro-N-{2-[3-(2,4-dichloro-phenyl)-ureido]-phenyl}-benzenesulfonamide

Yield: 75%

$^1$H-NMR (400 MHz, CDCl$_3$): δ 6.94 (1H, br), 6.99 (1H, dd, J=8.1, 1.5 Hz), 7.07 (1H, td, J=8.1, 1.5 Hz), 7.20-7.30 (4H, m), 7.34 (1H, d, J=2.4 Hz), 7.35 (2H, d, J=8.8 Hz), 7.58 (1H, dd, J=8.1, 1.5 Hz), 7.63 (2H, d, J=8.8 Hz), 8.06 (1H, d, J=9.0 Hz)

$^{13}$C-NMR (125 MHz, DMSO-d$_6$): δ 122.17, 122.92, 123.27, 123.41, 125.83, 126.47, 127.21, 127.50, 127.58, 128.60, 128.93, 129.22, 135.20, 135.96, 137.82, 138.33, 152.36

Melting point: 201 to 202° C.

2-p-Tolylethanesulfonyl acid[2-[3-(3,4-dichlorophenyl)ureido]phenyl]amide

ED-37

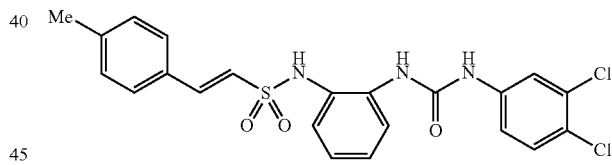

2-p-Tolyl-ethenesulfonic acid {2-[3-(3,4-dichloro-phenyl)-ureido]phenyl}-amide

Yield: 74%

$^1$H-NMR (400 MHz, CDCl$_3$): δ 2.34 (3H, s), 3.49 (1H, br), 6.79 (1H, d, J=15.9 Hz), 7.03 (1H, td, J=8.1, 1.5 Hz), 7.10-7.30 (8H, m), 7.36 (1H, d, J=15.9 Hz), 7.43 (1H, br), 7.53 (1H, d, J=2.4 Hz), 7.60 (1H, br), 7.72 (1H, dd, J=8.1, 1.5 Hz)

$^{13}$C-NMR (125 MHz, DMSO-d$_6$): δ 20.98, 118.13, 119.18, 121.42, 122.76, 123.08, 124.75, 125.57, 127.67, 128.43, 128.88, 129.45, 129.65, 130.51, 131.02, 136.29, 139.98, 140.64, 140.99, 152.20

Melting point: 182 to 183° C.

INDUSTRIAL APPLICABILITY

The non-peptidic amide derivatives according to the invention have serine racemase inhibitory activity, and may be used as a drug for preventing/treating pathological conditions due to excessive activation of NMDAR or neurodegenerative diseases. The non-peptidic amide derivatives may also be used as a reagent for analyzing the functions of serine racemase in the nervous system.

The invention claimed is:

1. An N-[(acyl)hydrazinocarbothioyl]acetamide derivative represented by a general formula [LW_1d], a salt thereof, a hydrate thereof, or a solvate thereof,

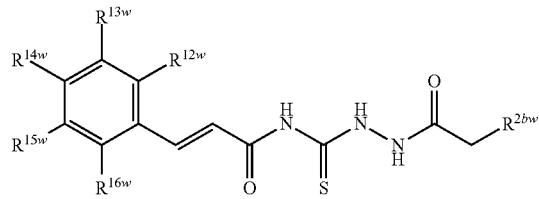

[LW_1d]

wherein $R^{13w}$ is a halogen atom, $R^{12w}$, $R^{14w}$, $R^{15w}$, and $R^{16w}$ are independently atoms selected from a hydrogen atom and a halogen atom, and $R^{2bw}$ is a substituted or unsubstituted phenyl group, or a substituted or unsubstituted thienyl group.

2. An N-[(acyl)hydrazinocarbothioyl]acetamide derivative represented by a general formula [LW_1g], a salt thereof, a hydrate thereof, or a solvate thereof,

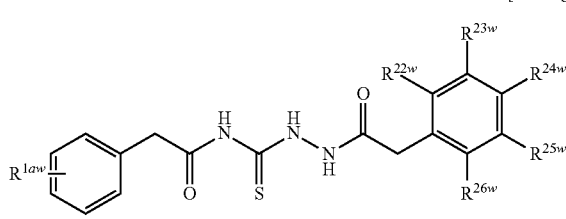

[LW_1g]

wherein $R^{1aw}$ is atoms or substituents selected from a halogen atom, an alkyl group, an alkoxy group, a nitro group, and a hydroxyl group that is optionally protected, and (1) $R^{24w}$ is a halogen atom, and $R^{22w}$, $R^{23w}$, $R^{25w}$, and $R^{26w}$ are a hydrogen atom, or (2) $R^{22w}$ and $R^{26w}$ are a halogen atom, and $R^{23w}$, $R^{24w}$, and $R^{25w}$ are a hydrogen atom, or (3) $R^{23w}$ and $R^{25w}$ are a halogen atom, and $R^{22w}$, $R^{24w}$, and $R^{26w}$ are a hydrogen atom.

3. An N-[(acyl)hydrazinocarbothioyl]acetamide derivative represented by a general formula [LW_1c], a salt thereof, a hydrate thereof, or a solvate thereof,

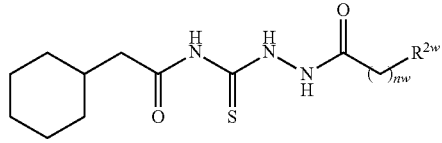

[LW_1c]

wherein $R^{2w}$ is a substituted or unsubstituted aryl group, or a substituted or unsubstituted heterocyclic group that comprises an oxygen atom or a sulfur as a ring atom, and nw is 0, 1, or 2.

4. The N-[(acyl)hydrazinocarbothioyl]acetamide derivative represented by a general formula [LW_1d], a salt thereof, a hydrate thereof, or a solvate thereof, of claim 1,

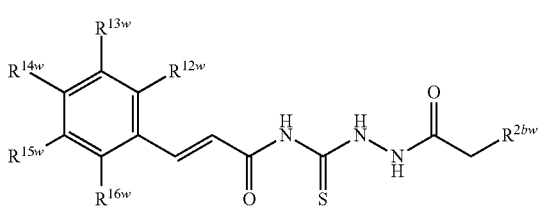

[LW_1d]

wherein $R^{13w}$ and $R^{15w}$ are a halogen atom, $R^{12w}$, $R^{14w}$, and $R^{16w}$ are a hydrogen atom, and $R^{2bw}$ is phenyl group.

5. A pharmaceutical composition for treating neurodegenerative diseases or hyperexcitable brain conditions, comprising an N-[(acyl)hydrazinocarbothioyl]acetamide derivative, a salt thereof, a hydrate thereof, or a solvate thereof, of claim 1.

6. A pharmaceutical composition for treating neurodegenerative diseases or hyperexcitable brain conditions, comprising an N-[(acyl)hydrazinocarbothioyl]acetamide derivative, a salt thereof, a hydrate thereof, or a solvate thereof, of claim 2.

7. A pharmaceutical composition for treating neurodegenerative diseases or hyperexcitable brain conditions, comprising an N-[(acyl)hydrazinocarbothioyl]acetamide derivative, a salt thereof, a hydrate thereof, or a solvate thereof, of claim 3.

* * * * *